United States Patent
Kaehr et al.

(10) Patent No.: US 9,989,447 B1
(45) Date of Patent: Jun. 5, 2018

(54) SHAPE-PRESERVING TRANSFORMATIONS OF ORGANIC MATTER AND COMPOSITIONS THEREOF

(71) Applicants: Sandia Corporation, Albuquerque, NM (US); STC.UNM, Albuquerque, NM (US)

(72) Inventors: Bryan J. Kaehr, Albuquerque, NM (US); Kristin Meyer, Tijeras, NM (US); Jason L. Townson, Seattle, WA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days. days.

(21) Appl. No.: 14/795,366

(22) Filed: Jul. 9, 2015

Related U.S. Application Data

(63) Continuation of application No. 13/869,799, filed on Apr. 24, 2013, now Pat. No. 9,273,305.

(60) Provisional application No. 61/638,315, filed on Apr. 25, 2012.

(51) Int. Cl.
*C12N 11/14* (2006.01)
*G01N 1/28* (2006.01)

(52) U.S. Cl.
CPC ......... *G01N 1/2806* (2013.01); *G01N 1/2853* (2013.01)

(58) Field of Classification Search
None
See application file for complete search history.

(56) References Cited

U.S. PATENT DOCUMENTS

| | | |
|---|---|---|
| 5,078,919 A | 1/1992 | Ashley et al. |
| 5,122,305 A | 6/1992 | Ashley et al. |
| 5,137,659 A | 8/1992 | Ashley et al. |
| 5,151,110 A | 9/1992 | Bein et al. |
| 5,224,972 A | 7/1993 | Frye et al. |
| 5,240,647 A | 8/1993 | Ashley et al. |
| 5,306,445 A | 4/1994 | Reed et al. |
| 5,313,485 A | 5/1994 | Hamil et al. |
| 5,565,142 A | 10/1996 | Deshpande et al. |
| 5,589,396 A | 12/1996 | Frye et al. |

(Continued)

FOREIGN PATENT DOCUMENTS

| | | |
|---|---|---|
| WO | WO 03/016040 A1 | 2/2003 |
| WO | WO 2008/060883 A2 | 5/2008 |

(Continued)

OTHER PUBLICATIONS

Campbell, Neil A; et al; Biology, 5th Ed., 136-139, 1999.*

(Continued)

*Primary Examiner* — David W Berke-Schlessel
(74) *Attorney, Agent, or Firm* — Helen S. Baca

(57) ABSTRACT

The present invention relates to methods of transforming organic matter into organic-inorganic composites, inorganic replicas, or conductive replicas. Organic matter, such as biological cells and tissue and organs, can be converted into such composites and replicas using the methods described herein. In particular, such methods transform organic matter (into inorganic, organic-inorganic, or conductive constructs), while simultaneously preserving microscopic and/or macroscopic structural detail.

23 Claims, 29 Drawing Sheets

(56) References Cited

U.S. PATENT DOCUMENTS

| | | | |
|---|---|---|---|
| 5,770,275 | A | 6/1998 | Raman et al. |
| 5,772,735 | A | 6/1998 | Sehgal et al. |
| 5,858,457 | A | 1/1999 | Brinker et al. |
| 5,935,646 | A | 8/1999 | Raman et al. |
| 5,948,482 | A | 9/1999 | Brinker et al. |
| 5,949,071 | A | 9/1999 | Ruffner et al. |
| 6,057,377 | A | 5/2000 | Sasaki et al. |
| 6,258,305 | B1 | 7/2001 | Brinker et al. |
| 6,264,741 | B1 | 7/2001 | Brinker et al. |
| 6,270,846 | B1 | 8/2001 | Brinker et al. |
| 6,387,453 | B1 | 5/2002 | Brinker et al. |
| 6,471,761 | B2 | 10/2002 | Fan et al. |
| 6,495,352 | B1 | 12/2002 | Brinker et al. |
| 6,536,604 | B1 | 3/2003 | Brinker et al. |
| 6,808,867 | B2 | 10/2004 | Doshi et al. |
| 6,913,832 | B2 | 7/2005 | Fan et al. |
| 6,983,093 | B2 | 1/2006 | Fraval et al. |
| 7,332,264 | B2 | 2/2008 | Doshi et al. |
| 7,485,343 | B1 | 2/2009 | Branson et al. |
| 7,744,673 | B2 | 6/2010 | Jiang et al. |
| RE41,612 | E | 8/2010 | Brinker et al. |
| 7,947,579 | B2 | 5/2011 | Jiang et al. |
| 8,092,595 | B1 | 1/2012 | Fan et al. |
| 8,187,678 | B2 | 5/2012 | Jiang et al. |
| 8,246,933 | B2 | 8/2012 | Jiang et al. |
| 8,318,127 | B1 | 11/2012 | Jiang et al. |
| 8,501,057 | B1 | 8/2013 | Jiang et al. |
| 8,663,742 | B2 | 3/2014 | Kissel et al. |
| 9,273,305 | B1 | 3/2016 | Kaehr et al. |
| 2011/0186971 | A1 | 8/2011 | Jiang et al. |
| 2011/0268791 | A1 | 11/2011 | Liu et al. |
| 2012/0040577 | A1 | 2/2012 | Kissel et al. |

FOREIGN PATENT DOCUMENTS

| | | | | |
|---|---|---|---|---|
| WO | WO 2011011468 | A2 * | 1/2011 | ............. C12N 11/14 |
| WO | WO 2012/149376 | A2 | 11/2012 | |
| WO | WO 2013/056132 | A2 | 4/2013 | |
| WO | WO 2013/103614 | A1 | 7/2013 | |

OTHER PUBLICATIONS

U.S. Appl. No. 12/903,577, filed Oct. 13, 2010, Brinker et al.
U.S. Appl. No. 12/909,572, filed Oct. 21, 2010, Brinker et al.
U.S. Appl. No. 13/253,964, filed Oct. 6, 2011, Brinker et al.
U.S. Appl. No. 13/484,139, filed May 30, 2012, Brinker et al.
U.S. Appl. No. 13/869,799, filed Apr. 24, 2013, Kaehr et al.
Alemán J et al., "Definitions of terms relating to the structure and processing of sols, gels, networks, and inorganic-organic hybrid materials (IUPAC Recommendations 2007)," *Pure Appl. Chem.* 2007;79(10):1801-9.
Antonelli DM et al., "Synthesis of hexagonally packed mesoporous $TiO_2$ by a modified sol-gel method," *Angew. Chem. Int. Ed. Engl.* 1995;34:2014-7.
Ashley CE et al., "Cell-specific delivery of diverse cargos by bacteriophage MS2 virus-like particles," *ACS Nano* Jul. 26, 2011;5(7):5729-45.
Ashley CE et al., "The targeted delivery of multicomponent cargos to cancer cells by nanoporous particle-supported lipid bilayers," *Nat. Mater.* May 2011;10(5):389-97.
Avnir D et al., "Recent bio-applications of sol-gel materials," *J. Mater. Chem.* 2006;16:1013-30.
Baca HK et al., "Cell-directed-assembly: Directing the formation of nano/bio interfaces and architectures with living cells," *Biochim. Biophys. Acta* Mar. 2011;1810(3):259-67.
Baca HK et al., "Cell-directed assembly of bio/nano interfaces—A new scheme for cell immobilization," *Acc. Chem. Res.* Sep. 2007;40(9):836-45.
Baca HK et al., "Cell-directed assembly of lipid-silica nanostructures providing extended cell viability," *Science* Jul. 21, 2006;313(5785):337-41.
Bao Z et al., "Chemical reduction of three-dimensional silica micro-assemblies into microporous silicon replicas," *Nature* Mar. 2007;446:172-5.
Bassindale et al., "Simple and mild preparation of silica-enzyme composites from silicic acid solution," *J. Mater. Chem.* 2009;19:7606-9.
Beck JS et al., "A new family of mesoporous molecular sieves prepared with liquid crystal templates," *J. Am. Chem. Soc.* 1992;114(27):10834-43.
Betancor L et al., "Bioinspired enzyme encapsulation for biocatalysis," *Trends Biotechnol.* Aug. 2008;26(10):566-72.
Boissiere C et al., "Aerosol route to functional nanostructured inorganic and hybrid porous materials," *Adv. Mater.* 2011;23:599-623.
Braet F et al., "Drying cells for SEM, AFM and TEM by hexamethyldisilazane: A study on hepatic endothelial cells," *J. Microsc.* Apr. 1997;186(1):84-7.
Bray DF et al., "Comparison of hexamethyldisilazane (HMDS), Peldri II and critical-point drying methods for scanning electron microscopy of biological specimens," *Microsc. Res. Tech.* 1993;26:489-95.
Brinker CJ et al., "Evaporation-induced self-assembly: Nanostructures made easy," *Adv. Mater.* May 1999;11(7):579-85.
Brott LL et al., "Ultrafast holographic nanopatterning of biocatalytically formed silica," *Nature* Sep. 2001;413(6853):291-3.
Browning N et al., "Recent developments in dynamic transmission electron microscopy," *Curr. Opin. Solid State Mater. Sci.* Feb. 2012;16(1):23-30.
Brunner E et al., "Chitin-based organic networks: An integral part of cell wall biosilica in the diatom Thalassiosira pseudonana," *Angew. Chem. Int. Ed. Engl.* 2009;48:9724-7.
Brunon A et al., "Mechanical characterization of liver capsule through uniaxial quasi-static tensile tests until failure," *J. Biomech.* 2010;43:2221-7.
Bushby AJ et al., "Imaging three-dimensional tissue architectures by focused ion beam scanning electron microscopy," *Nat. Protoc.* Jun. 2011;6(6):845-58 (abstract only).
Carroll NJ et al., "Microparticles with bimodal nanoporosity derived by microemulsion templating," *Langmuir* 2009;25(23):13540-4.
Cha JN et al., "Silicatein filaments and subunits from a marine sponge direct the polymerization of silica and silicones in vitro," *Proc. Nat'l Acad. Sci. USA* Jan. 1999;96:361-5.
Chen CL et al., "Peptide-based methods for the preparation of nanostructured inorganic materials," *Angew. Chem. Int. Ed. Engl.* Mar. 8, 2010;49(11):1924-42.
Chen Z et al., "DNA translocation through an array of kinked nanopores," *Nat. Mater.* Aug. 2010;9(8):667-75.
Chung K et al., "Structural and molecular interrogation of intact biological systems," *Nature* May 2013;497(7449):332-7.
Coradin T et al., "Interactions of bovine serum albumin and lysozyme with sodium silicate solutions," *Colloids Surf. B* 2003;29:189-96.
Dahmen U et al., "Background, status and future of the transmission electron aberration-corrected microscope project," *Phil. Trans. R. Soc. A* 2009;367:3795-808.
De Jonge N et al., "Electron microscopy of specimens in liquid," *Nat. Nanotechnol.* 2011;6:695-704.
Dendukuri D et al., "Continuous-flow lithography for high-throughput microparticle synthesis," *Nat. Mater.* May 2006;5(5):365-9.
Dengler EC et al., "Mesoporous silica-supported lipid bilayers (protocells) for DNA cargo delivery to the spinal cord," *J. Control. Release* Jun. 10, 2013;168(2):209-24.
Denk W et al., "Serial block-face scanning electron microscopy to reconstruct three-dimensional tissue nanostructure," *PLoS Biol.* Nov. 2004;2(11):1900-9.
Dickerson MB et al., "Protein- and peptide-directed syntheses of inorganic materials," *Chem. Rev.* 2008;108:4935-78.
Doshi N et al., "Red blood cell-mimicking synthetic biomaterial particles," *Proc. Natl. Acad. Sci. USA* Dec. 2009;106(51):21495-9.
Fratzl P et al., "Bio-inspired materials—Mining the old literature for new ideas," *Adv. Mater.* 2010;22:4547-50.

(56) References Cited

OTHER PUBLICATIONS

Frens G, "Controlled nucleation for the regulation of the particle size in monodisperse gold suspensions," *Nature* 1973;241:20-2.

Gautier C et al., "Biomimetic dual templating of silica by polysaccharide/protein assemblies," *Colloids Surf. B* 2008;65:140-5.

Geng Y et al., "Chloroquine-induced autophagic vacuole accumulation and cell death in glioma cells is p53 independent," *Neuro Oncol.* May 2010;12(5):473-81.

Gilbert TW et al., "Decellularization of tissues and organs," *Biomaterials* Jul. 2006;27(19):3675-83.

Glotzer SC et al., "Anisotropy of building blocks and their assembly into complex structures," *Nat. Mater.* Aug. 2007;6(8):557-62.

Goodwin WB et al., "Conversion of pollen particles into three-dimensional ceramic replicas tailored for multimodal adhesion," *Chem. Mater.* 2013;25(22):4529-36.

Haghgooie R et al., "Squishy non-spherical hydrogel microparticles," *Macromol. Rapid Commun.* Jan. 2010;31(2):128-34.

Hall A, "Rho GTPases and the actin cytoskeleton," *Science* Jan. 1998;279(5350):509-14.

Hanefeld U et al., "Understanding enzyme immobilisation," *Chem. Soc. Rev.* Feb. 2009;38(2):453-68.

Harper JC et al., "Biocompatible microfabrication of 3D isolation chambers for targeted confinement of individual cells and their progeny," *Anal. Chem.* Oct. 2012;84(21):8985-9.

Harper JC et al., "Cell-directed integration into three-dimensional lipid—Silica nanostructured matrices," *ACS Nano* Oct. 26, 2010;4(10):5539-50.

Harper JC et al., "Encapsulation of S. cerevisiae in poly(glycerol) silicate derived matrices: Effect of matrix additives and cell metabolic phase on long-term viability and rate of gene expression," *Chem. Mater.* Apr. 2011;23(10):2555-64.

Harper JC et al., "Orthogonal cell-based biosensing: Fluorescent, electrochemical, and colorimetric detection with silica-immobilized cellular communities integrated with an ITO-glass/plastic laminate cartridge," *Small* Sep. 10, 2012;8(17):2743-51.

Hatton B et al., "Assembly of large-area, highly ordered, crack-free inverse opal films," *Proc. Nat'l Acad. Sci. USA* 2010;107:10354-9.

Helgeson ME et al., "Hydrogel microparticles from lithographic processes: novel materials for fundamental and applied colloid science," *Curr. Opin. Colloid Interface Sci.* Apr. 1, 2011;16(2):106-17.

Hildebrand M et al., "Application of AFM in understanding biomineral formation in diatoms," *Pflügers Arch.* 2008;456:127-37.

Hildebrand M, "Diatoms, biomineralization processes, and genomics," *Chem. Rev.* 2008;108:4855-74.

Hildebrand M, "Prospects of manipulating diatom silica nanostructure," *J. Nanosci. Nanotechnol.* 2005;5:146-57.

Holland BT et al., "Synthesis of macroporous minerals with highly ordered three-dimensional arrays of spheroidal voids," *Science* Jul. 1998;281:538-40.

Holzapfel GA et al., "Biomechanics of soft tissue," *Biomech Preprint Series*, paper No. 7, Graz University of Technology, Austria, Nov. 2000 (15 pp.).

Hu CMJ et al., "Erythrocyte membrane-camouflaged polymeric nanoparticles as a biomimetic delivery platform," *Proc. Natl. Acad. Sci. USA* Jul. 5, 2011;108(27):10980-5.

Hu CMJ et al., "Erythrocyte-inspired delivery systems," *Adv. Healthcare Mater.* Sep. 2012;1(5):537-47.

Hudson S et al., "Proteins in mesoporous silicates," *Angew. Chem. Int. Ed. Engl.* 2008;47:8582-94.

Huo Q et al., "Generalized synthesis of periodic surfactant/inorganic composite materials," *Nature* 1994;368:317-21.

Jiang X et al., "Aerosol-assisted synthesis of monodisperse single-crystalline α-cristobalite nanospheres," *Chem. Commun. (Camb.)* Jan. 30, 2012;48(9):1293-5.

Jiang X et al., "Aerosol fabrication of hollow mesoporous silica nanoparticles and encapsulation of L-methionine as a candidate drug cargo," *Chem. Commun. (Camb.)* May 7, 2010;46(17):3019-21.

Jiang X et al., "Hydrothermal synthesis of monodisperse single-crystalline alpha-quartz nanospheres," *Chem. Commun. (Camb.)* Jul. 14, 2011;47(26):7524-6.

Jiang X et al., "Photoresponsive release from azobenzene-modified single cubic crystal NaCl/silica particles," *J. Nanomater.* 2011; Art. No. 439756 (6 pages).

Johnson P et al., "Nano-engineered, ultra stable, live cell vaccines against tuberculosis," 2011, 1 page (available from http://posterhall.org/system/igert/igert2011/posters/146/presentations/2011_IGERT_final_-_PJohnson.pdf?1302924782, last accessed Apr. 20, 2014).

Kaehr B et al., "Cellular complexity captured in durable silica biocomposites," *Proc. Nat'l Acad. Sci. USA* Oct. 23, 2012;109(43):17336-41.

Kaehr B et al., Supporting information for "Cellular complexity captured in durable silica biocomposites," *Proc. Nat'l Acad. Sci. USA* Oct. 23, 2012;109(43):17336-41, available at http://www.pnas.org/content/109/43/17336.long?tab=ds (last accessed May 1, 2014) (6 pages).

Kemmenoe BH et al., "Structure-analysis of sputter-coated and ion-beam sputter-coated films: A comparative-study," *J. Microsc.* Nov. 1983;132(Pt 2):153-63 (abstract only).

Khripin CY et al., "Protein-directed assembly of arbitrary three-dimensional nanoporous silica architectures," *ACS Nano* 2011;5(2):1401-9.

Khripin CY et al., Supporting information for "Protein-directed assembly of arbitrary three-dimensional nanoporous silica architectures," *ACS Nano* 2011;5(2):1401-9, available at http://pubs.acs.org/doi/supp1/10.1021/nn1031774 (last accessed May 1, 2014) (7 pages).

Kirk SE et al., "Application of environmental scanning electron microscopy to determine biological surface structure," *J. Microsc.* Feb. 2009;233(2):205-24.

Kresge CT et al., "Ordered mesoporous molecular sieves synthesized by a liquid-crystal template mechanism," *Nature* Oct. 1992;359:710-2.

Kröger N, "Prescribing diatom morphology: Toward genetic engineering of biological nanomaterials," *Curr. Opin. Chem. Biol.* 2007;11:662-9.

Kröger N et al., "Polycationic peptides from diatom biosilica that direct silica nanosphere formation," *Science* 1999;286:1129-32.

Kröger N et al., "Self-assembly of highly phosphorylated silaffins and their function in biosilica morphogenesis," *Science* 2002;298:584-6.

Kröger N et al., "Species-specific polyamines from diatoms control silica morphology," *Proc. Nat'l Acad. Sci. USA* 2000;97(26):14133-8.

Kumar A et al., "Origins of the anomalous stress behavior in charged colloidal suspensions under shear," *Phys. Rev. E* Nov. 2010;82(5 Pt 1):051401 (7 pp.).

Le Douarin NM, "The avian embryo as a model to study the development of the neural crest: A long and still ongoing story," *Mech. Dev.* Sep. 2004;121(9):1089-102.

Lee KJ et al., "Recent advances with anisotropic particles," *Curr. Opin. Colloid Interface Sci.* Jun. 2011;16(3):195-202.

Leong HS et al., "Intravital imaging of embryonic and tumor neovasculature using viral nanoparticles," *Nat. Protoc.* Aug. 2010;5(8):1406-17.

Li D et al., "Morphology-controlled synthesis of silica nanotubes through pH- and sequence-responsive morphological change of bacterial flagellar biotemplates," *J. Mater. Chem.* 2012;22:15702-9.

Lim HWG et al., "Stomatocyte-discocyte-echinocyte sequence of the human red blood cell: evidence for the bilayer-couple hypothesis from membrane mechanics," *Proc. Natl. Acad. Sci. USA* Dec. 2002;99(26):16766-9.

Lipka J et al., "Biodistribution of PEG-modified gold nanoparticles following intratracheal instillation and intravenous injection," *Biomaterials* Sep. 2010;31(25):6574-81.

Liu J et al., "Electrostatically mediated liposome fusion and lipid exchange with a nanoparticle-supported bilayer for control of surface charge, drug containment, and delivery," *J. Am. Chem. Soc.* Jun. 10, 2009;131(22):7567-9.

(56) References Cited

OTHER PUBLICATIONS

Liu J et al., "Porous nanoparticle supported lipid bilayers (protocells) as delivery vehicles," *J. Am. Chem. Soc.* Feb. 4, 2009;131(4):1354-5.

Losic D et al., "Diatomaceous lessons in nanotechnology and advanced materials," *Adv. Mater.* 2009;21:2947-58.

Lu Y et al., "Aerosol-assisted self-assembly of mesostructured spherical nanoparticles," *Nature* Mar. 1999;398:223-6.

Lu Y et al., "Evaporation-induced self-assembly of hybrid bridged silsesquioxane film and particulate mesophases with integral organic functionality," *J. Am. Chem. Soc.* 2000;122(22):5258-61.

Mann S et al., "Synthesis of inorganic materials with complex form," *Nature* Jul. 1996;382:313-8.

McIntosh R et al., "New views of cells in 3D: An introduction to electron tomography," *Trends Cell Biol.* Jan. 2005;15(1):43-51.

Merkel TJ et al., "Scalable, shape-specific, top-down fabrication methods for the synthesis of engineered colloidal particles," *Langmuir* Aug. 20010;26(16):13086-96.

Merkel TJ et al., "Using mechanobiological mimicry of red blood cells to extend circulation times of hydrogel microparticles," *Proc. Natl. Acad. Sci. USA* Jan. 2011;108(2):586-91.

Meunier CF et al., "Encapsulation of cells within silica matrixes: Towards a new advance in the conception of living hybrid materials," *J. Colloid Interface Sci.* 2010;342:211-24.

Meyer KC et al., "Mechanically encoded cellular shapes for synthesis of anisotropic mesoporous particles," *J. Am. Chem. Soc.* 2014;136:13138-41.

Meyer KC et al., Supporting information for "Mechanically encoded cellular shapes for synthesis of anisotropic mesoporous particles," *J. Am. Chem. Soc.* 2014;136:13138-41 (10 pp.).

Miyako E et al., "Self-assembled carbon nanotube honeycomb networks using a butterfly wing template as a multifunctional nanobiohybrid," *ACS Nano* 2013;7:8736-42.

Moghaddam S et al., "An inorganic-organic proton exchange membrane for fuel cells with a controlled nanoscale pore structure," *Nat. Nanotechnol.* Mar. 2010;5(3):230-6.

Mohandas N et al., "Red cell membrane: past, present, and future," *Blood* Nov. 2008;112(10):3939-48.

Niu L et al., "Infiltration of silica inside fibrillar collagen," *Angew. Chem. Int. Ed. Engl.* 2011;50:11688-91.

Oberdörster G et al., "Toxicology of nanoparticles: A historical perspective," *Nanotoxicology* 2007;1(1):2-25.

Ohta K et al., "Beam deceleration for block-face scanning electron microscopy of embedded biological tissue," *Micron* Apr. 2012;43(5):612-20.

Pal S, "Mechanical properties of biological materials," in *Design of Artificial Human Joints & Organs*, Springer Science + Business Media, New York, NY, 2014, pp. 23-40.

Paris O et al., "Biomimetics and biotemplating of natural materials," *MRS Bull.* 2010;35:219-25.

Patwardhan SV et al., "On the role(s) of additives in bioinspired silicification," *Chem. Commun.* 2005;9:1113-21.

Perutz MF, "Submicroscopic structure of the red cell," *Nature* Feb. 1948;161(4084): 204-5.

Pluk H et al., "Advantages of indium-tin oxide-coated glass slides in correlative scanning electron microscopy applications of uncoated cultured cells," *J. Microsc.* Mar. 2009;233(3):353-63.

Pouget E et al., "Hierarchical architectures by synergy between dynamical template self-assembly and biomineralization," *Nat. Mater.* 2007;6:434-9.

Rempe S et al., "Biomimetic membranes for water purification," *Sandia Report No. SAND2011-2061P*, 2011 (28 pages).

Roh KH et al., "Biphasic Janus particles with nanoscale anisotropy," *Nat. Mater.* Oct. 2005;4(10):759-63.

Rong J et al., "Tobacco mosaic virus templated synthesis of one dimensional inorganic-polymer hybrid fibres," *J. Mater. Chem.* 2009;19:2841-5.

Sandhage KH, "Materials 'alchemy': Shape-preserving chemical transformation of micro-to-macroscopic 3-D structures," *JOM (Journal of the Minerals, Metals & Materials Society (TMS))* Jun. 2010;62(6):32-43.

Scheffel A et al., "Nanopatterned protein microrings from a diatom that direct silica morphogenesis," *Proc. Nat'l Acad. Sci. USA* 2011;108:3175-80.

Schnepp Z et al., "Biotemplating of metal carbide microstructures: the magnetic leaf," *Angew. Chem. Int. Ed. Engl.* Sep. 3, 2010;49(37):6564-6.

Severs NJ, "Freeze-fracture electron microscopy," *Nat. Protoc.* 2007;2(3):547-76 (abstract only).

Sheetz MP et al., "Biological membranes as bilayer couples: A molecular mechanism of drug-erythrocyte interactions," *Proc. Natl. Acad. Sci. USA* Nov. 1974;71(11):4457-61.

Shenton W et al., "Inorganic-organic nanotube composites from templated mineralization of tobacco mosaic virus," *Adv. Mater.* 1999;11(3):253-6.

Shopsowitz KE et al., "Free-standing mesoporous silica films with tunable chiral nematic structures," *Nature* 2010;468:422-5.

Shum HC et al., "Droplet microfluidics for fabrication of non-spherical particles," *Macromol. Rapid Commun.* Jan. 2010;31(12):108-18.

Sing KSW et al., "Reporting physisorption date for gas/solid systems with special reference to the determination of surface area and porosity (Recommendations 1984)," *J. Pure Appl. Chem.* 1985;57(4):603-19.

Stein A et al., "Morphological control in colloidal crystal templating of inverse opals, hierarchical structures, and shaped particles," *Chem. Mater.* 2008;20:649-66.

Stepankova V et al., "Strategies for stabilization of enzymes in organic solvents," *ACS Catal.* 2013;3(12):2823-36.

Sun T et al., "Synthesis of microporous transition-metal-oxide molecular sieves by a supramolecular templating mechanism," *Nature* 1997;389:704-6.

Taney PT et al, "A neutral templating route to mesoporous molecular sieves," *Science* 1995;267:865-7.

Tesson B et al., "Extensive and intimate association of the cytoskeleton with forming silica in diatoms: Control over patterning on the meso- and micro-scale," *PloS One* 2010;5:e14300 (13 pages).

Torquato S et al., "Jammed hard-particle packings: From Kepler to Bernal and beyond," *Rev. Mod. Phys.* Sep. 2010;82(3):2633-72.

Townley HE et al., "Modification of the physical and optical properties of the frustule of the diatom *Coscinodiscus wailesii* by nickel sulfate," *Nanotechnology* 2007;18:295101-6.

Townson JL et al., "Synthetic fossilization of soft biological tissues and their shape-preserving transformation into silica or electron-conductive replicas," *Nat. Commun.* Dec. 2014;5:5665 (8 pp.).

Townson JL et al., Supporting information for "Synthetic fossilization of soft biological tissues and their shape-preserving transformation into silica or electron-conductive replicas," *Nat. Commun.* Dec. 2014;5:5665 (8 pp.).

Ushiki T et al., "Low-voltage backscattered electron imaging of non-coated biological samples in a low-vacuum environment using a variable-pressure scanning electron microscope with a YAG-detector," *J. Electron Microsc. (Tokyo)* 1998;47(4):351-4 (abstract only).

Van Bommel KJC et al., "Organic templates for the generation of inorganic materials," *Angew. Chem. Int. Ed. Engl.* 2003;42(9):980-99.

Van Opdenbosch D et al., "Silica replication of the hierarchical structure of wood with nanometer precision," *J. Mater. Res.* May 2011;26(10):1193-202.

Walker DA et al., "Geometric curvature controls the chemical patchiness and self-assembly of nanoparticles," *Nat. Nanotechnol.* Sep. 2013;8(9):676-81.

Walther A et al., "Janus particles: synthesis, self-assembly, physical properties, and applications," *Chem. Rev.* Jul. 10, 2013;113(7):5194-261.

Warnock JN et al., "Bioreactor systems for the production of biopharmaceuticals from animal cells," *Biotechnol. Appl. Biochem.* 2006;45:1-12.

(56) References Cited

OTHER PUBLICATIONS

Wei Y et al., "A novel method for enzyme immobilization: direct encapsulation of acid phosphatase in nanoporous silica host materials," *J. Nanosci. Nanotechnol.* Mar. 2001;1(1):83-93.

Wei Y et al., "Preparation and physisorption characterization of D-glucose-templated mesoporous silica sol-gel materials," *Chem. Mater.* 1999;11:2023-9.

Wilson BS, et al., "Calcium-dependent clustering of inositol 1,4,5-trisphosphate receptors," *Mol. Biol. Cell* Jun. 1998;9:1465-78.

Wong P, "A basis of echinocytosis and stomatocytosis in the disc-sphere transformations of the erythrocyte," *J. Theor. Biol.* Feb. 7, 1999;196(3):343-61.

Xing Z et al., "Scale-up analysis for a CHO cell culture process in large-scale bioreactors," *Biotechnol. Bioeng.* Jul. 2009;103(4):733-46.

Yan J et al., "Linking synchronization to self-assembly using magnetic Janus colloids," *Nature* Nov. 2012;491(7425):578-81.

Yin Y et al., "Template-assisted self-assembly: a practical route to complex aggregates of monodispersed colloids with well-defined sizes, shapes, and structures," *J. Am. Chem. Soc.* Sep. 2001;123(36):8718-29.

Zeming KK et al., "Rotational separation of non-spherical bioparticles using I-shaped pillar arrays in a microfluidic device," *Nat. Commun.* 2013;4:1625 (8 pp.).

Zhang L et al., "Nanoparticles in medicine: Therapeutic applications and developments," *Clin. Pharmacol. Ther.* May 2008;83(5):761-9.

Zhao D et al., "Triblock copolymer syntheses of mesoporous silica with periodic 50 to 300 angstrom pores," *Science* 1998;279(5350):548-52.

Zimmerman AB et al., "Titania and silica materials derived from chemically dehydrated porous botanical templates," *Chem. Mater.* 2012;24(22):4301-10.

\* cited by examiner

Attorney Reference No. SD13102.0/S135020

SHAPE-PRESERVING TRANSFORMATIONS OF ORGANIC MATTER AND COMPOSITIONS THEREOF

CROSS-REFERENCE TO RELATED APPLICATION

This application is a continuation-in-part of prior U.S. application Ser. No. 13/869,799, filed Apr. 24, 2013, which in turn claims the benefit of U.S. Provisional Application No. 61/638,315, filed Apr. 25, 2012, each of which is hereby incorporated by reference in its entirety.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to methods of transforming organic matter into organic-inorganic composites, inorganic or carbon replicas, as well as conductive replicas. Organic matter, such as biological tissue and organs, can be converted into such composites and replicas using the methods described herein. In particular, such methods transform organic matter (into inorganic, organic-inorganic, or conductive constructs), while simultaneously preserving microscopic and/or macroscopic structural detail.

BACKGROUND OF THE INVENTION

Structural studies of biological tissues can provide important information regarding dynamic organismal processes. For instance, such studies can be employed to understand how and where therapeutic agents co-localize in a tissue or an organ for a subject. In particular, methods for visualizing biological structures, on a micrometer- or even nanometer-scale, should preserve the three-dimensional context of the entire tissue or organ.

Yet, probing such structures can be difficult due to the fragility of some biological structures. Further, internal organismal structures are generally inaccessible, and access may require damage to external structures that support internal organs and tissues. Thus, any technique to elucidate such structures should not only maintain the spatial location of internal and external organismal structures but also stabilize biological structures for further experimental analysis (e.g., by scanning electron microscopy).

Many biological structures exhibit great spatial (e.g., two-dimensional and three-dimensional) diversity. Yet capturing these diverse, structural details can be challenging. Presently, a generalized method to capture such structures is lacking. Such a generalized method would be beneficial in order to develop, synthesize, and design a new class of complex and biologically-templated materials and constructs.

SUMMARY OF THE INVENTION

Accordingly, we present a method for specimen preparation that stabilizes biological structures. In particular, the methods herein provide a nanoscale, conformal layer of an inorganic material (e.g., silica) on the biological sample. This conformal layer accurately replicates the structural details of the underlying sample (e.g., a biological specimen, such as a cell sample or a tissue sample). In addition, the conformal layer generally includes an inorganic (silica) material, which forms a durable layer on and within the sample. This conformal layer not only exists on external surfaces of the sample but also on internal surfaces and can even provide nanometer-scale resolved features (e.g., protein fibrils). Sample surfaces (e.g., internal and/or external surfaces) are subjected to a solution-phase, sol-gel replicative process and subsequently dried without loss of structural details arising from stresses imposed by drying or other sample preparation procedures. Thus, this process of silica bioreplication (SBR) transforms delicate structures into durable specimens (e.g., silica composites and other processed replicas) without structural changes.

We also describe methods for further processing silica composites after SBR (e.g., thereby forming a silica replica). Exemplary processing conditions include high temperature treatment, such as pyrolysis. Due to the mechanical stability of the silica network, nano- to macro-scale shape is preserved under high-temperature processing. In certain embodiments, all specimen planes are rendered conductive allowing infinite and arbitrary sectioning of the specimen using, for instance, mechanical sectioning and focused ion beams.

The processes herein can be employed to provide any useful construct (e.g., composite or replica). For instance, silica composites (composed of silica and the underlying organic matter of the specimen) can be transformed into conductive structures or purely inorganic structures. In one instance, the silica composite can be carbonized to transform the organic matter to conductive carbon, thereby providing a conductive, carbonized replica. In another instance, the silica present in the carbonized replica can be etched, thereby providing a conductive, purely carbon replica. In yet another instance, the silica composite can be calcined to remove organic matter, thereby providing a purely inorganic replica (e.g., a silica replica). In further instances, the composite can be converted or functionalized to include any useful particle, surface chemistry, and/or material (e.g., a metal or metalloid) to provide a converted and/or functionalized construct. Accordingly, the properties of resultant constructs are enabling for materials analysis, preservation, and ready transformation into other technologically-relevant or engineered materials (e.g., semiconductor, magnetic, high-index, and photonic materials).

In particular, conductive replicas can be useful for further experimental analyses that rely on a conductive surface for measurements, such as electron-based imaging including scanning electron microscopy (SEM) and focused ion beam (FIB). For instance, following SBR, tissues can undergo shape-preserving carbonization reactions that result in intrinsically conductive samples, allowing for chemical identification of nano-scale objects (e.g., metal nanoparticles) in the three-dimensional context of a specimen (e.g., using high-current electron beams to generate elemental (Z) contrast).

In addition, conductive replicas can be subjected to high current electron beams and analyzed using detection of back-scattered electrons. This enables elemental imaging of specimens containing both high and low Z elements, and further enables resolution of sub-surface structures due to the deeper penetration depth of backscatter electrons. Unlike the current state of the art, this technology does not require freeze-drying, vitrification, or polymer-embedding. Further, the methods herein render the specimen resistant to chemical perturbation and to electron/photon radiation, and can be broadly employed across sub-cellular, tissue, and organism scales. Additional details follow.

Definitions

As used herein, the term "about" means +/−10% of any recited value. As used herein, this term modifies any recited value, range of values, or endpoints of one or more ranges.

By "cell" is meant a biological unit including, at least, a cell membrane and one or more biomolecules (e.g., proteins, peptides, nucleic acids, and/or polysaccharides). Exemplary cells include a red blood cell, a eukaryotic cell, or a prokaryotic cell. Additional cells are described herein.

By "composite" is meant a structure including a sample, or a portion thereof, and one or more inorganic nanolayers (e.g., silica nanolayers). Exemplary samples include biological samples, such as a cell, a tissue sample, a population of cells, an organ, an embryo, etc.

By "replica" is meant a structure derived from a composite, as defined herein, but lacking the organic matter from the sample in its native form. In one instance, the replica is a silicon replica including one or more inorganic silica nanolayers. In another instance, the replica is a carbonized replica including one or more inorganic silica nanolayers and a carbonized form of the sample. In yet another instance, the replica is a conductive carbon replica (or a carbon replica) including the carbonized form of the sample but lacking a silica nanolayer. Other replicas and composites are described herein.

By "silicic acid" is meant a family of chemical compounds containing the element silicon attached to oxide and/or hydroxyl groups that are capable of condensing and forming oligomeric and/or polymeric silicon dioxide or silica coatings pursuant to the present invention. In one instance, silicic acid is a chemical compound having the structure $Si(OR)_4$, wherein each R is, independently, H or an optionally substituted alkyl, as defined herein (e.g., an optionally substituted $C_{1-6}$ alkyl). In another instance, a silicic acid is selected from the group of orthosilicic acid (generally referred to as silicic acid), metasilicic acid, disilic acid and pyrosilicic acid, among others. In yet another instance, a silicic acid (including a silicic acid derivative) includes tetramethoxysilane (TMOS), tetraethoxysilane (TEOS), as well as mixtures thereof.

By "micro" is meant having at least one dimension that is less than 1 mm. For instance, a microstructure (e.g., any structure described herein) can have a length, width, height, cross-sectional dimension, circumference, radius (e.g., external or internal radius), or diameter that is less than 1 mm.

By "nano" is meant having at least one dimension that is less than 1 μm. For instance, a nanostructure (e.g., any structure described herein) can have a length, width, height, cross-sectional dimension, circumference, radius (e.g., external or internal radius), or diameter that is less than 1 μm. In some embodiments, a nanolayer is a layer having a thickness (e.g., measured in a dimension that is orthogonal to an external or internal surface) that is of from about 0.01 nm to about 1,000 nm (e.g., of from about 0.01 nm to about 100 nm, such as of from about 0.01 nm to 5 nm, 0.01 nm to 10 nm, 0.01 nm to 20 nm, 0.01 nm to 50 nm, 0.1 nm to 5 nm, 0.1 nm to 10 nm, 0.1 nm to 20 nm, 0.1 nm to 50 nm, 0.1 nm to 100 nm, 1 nm to 5 nm, 1 nm to 10 nm, 1 nm to 20 nm, 1 nm to 50 nm, 1 nm to 100 nm, 2 nm to 5 nm, 2 nm to 10 nm, 2 nm to 20 nm, 2 nm to 50 nm, 2 nm to 100 nm, 4 nm to 5 nm, 4 nm to 10 nm, 4 nm to 20 nm, 4 nm to 50 nm, 4 nm to 100 nm, 10 nm to 20 nm, 10 nm to 50 nm, or 10 nm to 100 nm).

As used herein, the terms "top," "bottom," "upper," "lower," "above," and "below" are used to provide a relative relationship between structures. The use of these terms does not indicate or require that a particular structure must be located at a particular location in the apparatus.

The term "acyl," or "alkanoyl," as used interchangeably herein, represent an alkyl group, as defined herein, or hydrogen attached to the parent molecular group through a carbonyl group, as defined herein. This group is exemplified by formyl, acetyl, propionyl, butanoyl, and the like. The alkanoyl group can be substituted or unsubstituted. For example, the alkanoyl group can be substituted with one or more substitution groups, as described herein for alkyl. In some embodiments, the unsubstituted acyl group is a $C_{2-7}$ acyl or alkanoyl group.

By "alkaryl" is meant an aryl group, as defined herein, attached to the parent molecular group through an alkylene group, as defined herein. Similarly, by the term "alkheteroaryl" is meant a heteroaryl group, as defined herein, attached to the parent molecular group through an alkylene group. Other groups preceded by the prefix "alk-" are defined in the same manner. The alkaryl group can be substituted or unsubstituted. For example, the alkaryl group can be substituted with one or more substitution groups, as described herein for alkyl and/or aryl. Exemplary unsubstituted alkaryl groups are of from 7 to 16 carbons ($C_{7-16}$ alkaryl), as well as those having an alkylene group with 1 to 6 carbons and an aryl group with 4 to 18 carbons (i.e., $C_{1-6}$ alk-$C_{4-18}$ aryl).

By "alkcycloalkyl" is meant a cycloalkyl group, as defined herein, attached to the parent molecular group through an alkylene group, as defined herein. Exemplary unsubstituted alkcycloalkyl groups are of from 4 to 14 carbons ($C_{4-14}$ alkaryl), as well as those having an alkylene group with 1 to 6 carbons and a cycloalkyl group with 3 to 8 carbons (i.e., $C_{1-6}$ alk-$C_{3-8}$ aryl).

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{2-8}$ alkenyl; (2) $C_{2-8}$ alkynyl; (3) $C_{1-6}$ alkoxy (e.g., —$OR^Y$); (4) $C_{1-6}$ alkylsulfinyl (e.g., —$S(O)R^Y$); (5) $C_{1-6}$ alkylsulfonyl (e.g., —$SO_2R^Y$); (6) amino; (7) aryl (e.g., $C_{4-18}$ aryl); (8) arylalkoxy (e.g., —$OR^ZAr^Z$); (9) aryloyl (e.g., —$C(O)Ar^Z$); (10) azido (—$N_3$); (11) carboxyaldehyde (—C(O)H); (12) carboxyl (—C(O)OH); (13) $C_{3-8}$ cycloalkyl; (14) halo; (15) heterocyclyl (e.g., $C_{1-18}$ heterocyclyl including one or more heteroatoms, such as N, O, S, and P); (16) heterocyclyloxy (e.g., —$OHet^Z$); (17) heterocyclyloyl (e.g., —$C(O)Het^Z$); (18) hydroxyl; (19) N-protected amino; (20) nitro (—$NO_2$); (21) oxo (=O); (22) $C_{3-8}$ spirocyclyl; (23) $C_{1-6}$ thioalkoxy (e.g., —$SR^Y$); (24) thiol (—SH); (25) —$CO_2R^A$, where $R^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (26) —$C(O)NR^BR^C$, where each of $R^B$ and $R^C$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (27) —$SO_2R^D$, where $R^D$ is selected from the group consisting of (a) $C_{1-6}$ alkyl, (b) $C_{4-18}$ aryl, and (c) $C_{1-6}$ alk-$C_{4-18}$ aryl; (28) —$SO_2NR^ER^F$, where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; and (29) —$NR^GR^H$, where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, where in one embodiment no two groups are bound to the nitrogen atom through a carbonyl group or a sulfonyl group (e.g., where $R^Y$ is alkyl (e.g., $C_{1-6}$ alkyl), $R^Z$ is alkylene (e.g., $C_{1-6}$ alkylene), $Ar^Z$ is aryl (e.g., $C_{4-18}$ aryl), and $Het^Z$ is heterocyclyl (e.g., $C_{1-18}$ heterocyclyl including one or more heteroatoms, such as N, O, S, and P), as defined herein). The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "alkenyl" is meant an optionally substituted $C_{2-24}$ alkyl group having one or more double bonds. The alkenyl group can be cyclic (e.g., $C_{3-24}$ cycloalkenyl) or acyclic. The alkenyl group can also be substituted or unsubstituted. For example, the alkenyl group can be substituted with one or more substitution groups, as described herein for alkyl. In some embodiments, the unsubstituted alkenyl group is a $C_{2-6}$, $C_{2-12}$, $C_{2-18}$, or $C_{2-24}$ alkenyl group.

By "alkoxy" is meant —OR, where R is an optionally substituted alkyl group, as described herein. Exemplary alkoxy groups include methoxy, ethoxy, butoxy, trihaloalkoxy, such as trifluoromethoxy, etc. The alkoxy group can be substituted or unsubstituted. For example, the alkoxy group can be substituted with one or more substitution groups, as described herein for alkyl (e.g., alkoxy that is optionally substituted with one or more substitution groups, such as alkyl, haloalkyl, halo, etc.). Exemplary unsubstituted alkoxy groups include $C_{1-3}$, $C_{1-6}$, $C_{1-12}$, $C_{1-16}$, $C_{1-18}$, $C_{1-20}$, or $C_{1-24}$ alkoxy groups.

By "alkoxyalkyl" is meant an alkoxy group, as defined herein, attached to the parent molecular group through an alkylene group, as defined herein. The alkoxyalkyl group can be substituted or unsubstituted. For example, the alkoxyalkyl group can be substituted with one or more substitution groups, as described herein for alkyl. Exemplary unsubstituted alkoxyalkyl groups are of from 2 to 12 carbons ($C_{2-12}$ alkoxyalkyl), as well as those having an alkylene group with 1 to 6 carbons and an alkoxy group with 1 to 6 carbons (i.e., $C_{1-6}$ alkoxy-$C_{1-6}$ alkyl).

By "alkylene" is meant a bivalent form of an alkyl group, as described herein. Exemplary alkylene groups include methylene, ethylene, propylene, butylene, etc. In some embodiments, the alkylene group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted. For example, the alkylene group can be substituted with one or more substitution groups, as described herein for alkyl.

By "alkyleneoxy" is meant an alkylene group, as defined herein, attached to the parent molecular group through an oxygen atom.

By "alkynyl" is meant an optionally substituted $C_{2-24}$ alkyl group having one or more triple bonds. The alkynyl group can be cyclic or acyclic and is exemplified by ethynyl, 1-propynyl, and the like. The alkynyl group can also be substituted or unsubstituted. For example, the alkynyl group can be substituted with one or more substitution groups, as described herein for alkyl. In some embodiments, the unsubstituted alkynyl group is a $C_{2-6}$, $C_{2-12}$, $C_{2-18}$, or $C_{2-24}$ alkynyl group.

By "amido" is meant —$NR^{N1}(C(O)R^{N3})$, where $R^{N1}$ is H or optionally substituted alkyl and $R^{N3}$ is H, optionally substituted alkyl, or haloalkyl.

By "amino" is meant —$NR^{N1}R^{N2}$, where each of $R^{N1}$ and $R^{N2}$ is, independently, H or optionally substituted alkyl, or $R^{N1}$ and $R^{N2}$, taken together with the nitrogen atom to which each are attached, form a heterocyclyl group, as defined herein.

By "aminoalkyl" is meant an alkyl group, as defined herein, substituted by one to three amino groups, with the proviso that no more than one amino group may be attached to a single carbon atom of the alkyl group and is exemplified by aminomethyl, diaminopropyl, and the like.

By "aryl" is meant a group that contains any carbon-based aromatic group including, but not limited to, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) $C_{1-6}$ alkanoyl (e.g., —$C(O)R^Y$ or —$C(O)H$); (2) $C_{1-6}$ alkyl; (3) $C_{1-6}$ alkoxy; (4) $C_{1-6}$ alkoxy-$C_{1-6}$ alkyl (e.g., —$R^ZOR^Y$); (5) $C_{1-6}$ alkylsulfinyl (e.g., —$S(O)R^Y$); (6) $C_{1-6}$ alkylsulfinyl-$C_{1-6}$ alkyl (e.g., —$R^ZS(O)R^Y$); (7) $C_{1-6}$ alkylsulfonyl (e.g., —$SO_2R^Y$); (8) $C_{1-6}$ alkylsulfonyl-$C_{1-6}$ alkyl (e.g., —$R^ZSO_2R^Y$); (9) $C_{2-8}$ alkenyl; (10) $C_{2-8}$ alkynyl; (11) aryl (e.g., $C_{4-18}$ aryl); (12) amino; (13) $C_{1-6}$ aminoalkyl (e.g., —$R^ZNR^{N1}R^{N2}$, as defined herein for amino); (14) heteroaryl (e.g., $C_{1-18}$ heteroaryl including one or more heteroatoms, such as N, O, S, and P); (15) $C_{1-6}$ alk-$C_{4-18}$ aryl (e.g., —$R^ZAr^Z$); (16) aryloyl (e.g., —$C(O)Ar^Z$); (17) azido (—$N_3$); (18) $C_{1-6}$ azidoalkyl (e.g., —$R^ZN_3$); (19) carboxyaldehyde (—$C(O)H$); (20) carboxyaldehyde-$C_{1-6}$ alkyl (e.g., —$R^ZC(O)H$); (21) $C_{3-8}$ cycloalkyl; (22) $C_{1-6}$ alk-$C_{3-8}$ cycloalkyl (e.g., —$R^ZR^{CY}$); (23) halo; (24) $C_{1-6}$haloalkyl; (25) heterocyclyl (e.g., $C_{1-18}$ heterocyclyl including one or more heteroatoms, such as N, O, S, and P); (26) heterocyclyloxy (e.g., —$OHet^Z$); (27) heterocyclyloyl (e.g., —$C(O)Het^Z$); (28) hydroxyl; (29) $C_{1-6}$hydroxyalkyl (e.g., —$R^Z(OH)_{1-3}$); (30) nitro (—$NO_2$); (31) $C_{1-6}$nitroalkyl (e.g., —$R^Z(NO_2)_{1-3}$); (32) N-protected amino; (33) N-protected amino-$C_{1-6}$ alkyl; (34) oxo (=O); (35) $C_{1-6}$thioalkoxy (e.g., —$SR^Y$); (36) thio-$C_{1-6}$ alkoxy-$C_{1-6}$ alkyl (e.g., —$R^ZSR^Y$); (37) —$(CH_2)_rCO_2R^A$, where r is an integer of from zero to four, and $R^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (38) —$(CH_2)_rCONR^BR^C$, where r is an integer of from zero to four and where each $R^B$ and $R^C$ is independently selected from the group consisting of (a) hydrogen, (b) $C_{1-6}$ alkyl, (c) $C_{4-18}$ aryl, and (d) $C_{1-6}$ alk-$C_{4-18}$ aryl; (39) —$(CH_2)_rSO_2R^D$, where r is an integer of from zero to four and where $R^D$ is selected from the group consisting of (a) $C_{1-6}$ alkyl, (b) $C_{4-18}$ aryl, and (c) $C_{1-6}$ alk-$C_{4-18}$ aryl; (40) —$(CH_2)_rSO_2NR^ER^F$, where r is an integer of from zero to four and where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (41) —$(CH_2)_r NR^G R^H$, where r is an integer of from zero to four and where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, where in one embodiment no two groups are bound to the nitrogen atom through a carbonyl group or a sulfonyl group; (42) thiol (—SH); (43) perfluoroalkyl; (44) perfluoroalkoxy (e.g., —$OR^F$); (45) aryloxy (e.g., —$OAr^Z$); (46) cycloalkoxy (e.g., —$OR^{Cy}$); (47) cycloalkylalkoxy (e.g., —$OR^Z R^{Cy}$); and (48) arylalkoxy (e.g., —$OR^Z Ar^Z$)) (e.g., where $R^Y$ is alkyl (e.g., $C_{1-6}$ alkyl), $R^Z$ is alkylene (e.g., $C_{1-6}$ alkylene), $Ar^Z$ is aryl (e.g., $C_{4-18}$ aryl), $Het^Z$ is heterocyclyl (e.g., $C_{1-18}$ heterocyclyl including one or more heteroatoms, such as N, O, S, and P), $R^{Cy}$ is cycloalkyl (e.g., $C_{3-8}$ cycloalkyl), and $R^F$ is perfluoroalkyl (e.g., $C_{1-6}$ perfluoroalkyl), as defined herein). In particular embodiments, an unsubstituted aryl group is a $C_{4-18}$, $C_{4-14}$, $C_{4-12}$, $C_{4-10}$, $C_{6-18}$, $C_{6-14}$, $C_{6-12}$, or $C_{6-10}$ aryl group.

By "arylene" is meant a bivalent form of an aryl group, as described herein. Exemplary arylene groups include phenylene, naphthylene, biphenylene, triphenylene, diphenyl ether, acenaphthenylene, anthrylene, or phenanthrylene. In some embodiments, the arylene group is a $C_{4-18}$, $C_{4-14}$, $C_{4-12}$, $C_{4-10}$, $C_{6-18}$, $C_{6-14}$, $C_{6-12}$, or $C_{6-10}$ arylene group. The arylene group can be branched or unbranched. The arylene group can also be substituted or unsubstituted. For example, the arylene group can be substituted with one or more substitution groups, as described herein for aryl.

By "carbonyl" and the suffix "oyl" is meant —C(O)—.

By "cycloalkyl" is meant a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1]heptyl and the like. The cycloalkyl group can also be substituted or unsubstituted. For example, the cycloalkyl group can be substituted with one or more groups including those described herein for alkyl.

By "halo" is meant F, Cl, Br, or I.

By "haloalkyl" is meant an alkyl group, as defined herein, substituted with one or more halo. Exemplary haloalkyl groups include $C_{1-3}$, $C_{1-6}$, $C_{1-12}$, $C_{1-16}$, $C_{1-18}$, $C_{1-20}$, or $C_{1-24}$ haloalkyl groups.

By "heteroalkylene" is meant an alkylene group, as defined herein, containing one, two, three, or four non-carbon heteroatoms (e.g., independently selected from the group consisting of nitrogen, oxygen, phosphorous, sulfur, or halo).

By "heteroalkyleneoxy" is meant a heteroalkylene group, as defined herein, attached to the parent molecular group through an oxygen atom. Exemplary heteroalkyleneoxy groups include a divalent amido group (e.g., —$N(R^{N})C(O)$ or —$N=C(R^{N1})O$—, where $R^{N1}$ is H, optionally substituted alkyl, or optionally substituted haloalkyl).

By "heteroaryl" is meant a subset of heterocyclyl groups, as defined herein, which are aromatic, i.e., they contain 4n+2 pi electrons within the mono- or multicyclic ring system.

By "heterocyclyl" is meant a 5-, 6- or 7-membered ring, unless otherwise specified, containing one, two, three, or four non-carbon heteroatoms (e.g., independently selected from the group consisting of nitrogen, oxygen, phosphorous, sulfur, silicon, or halo). The 5-membered ring has zero to two double bonds and the 6- and 7-membered rings have zero to three double bonds. The term "heterocyclyl" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring, and another monocyclic heterocyclic ring, such as indolyl, quinolyl, isoquinolyl, tetrahydroquinolyl, benzofuryl, benzothienyl and the like. Heterocyclics include thiiranyl, thietanyl, tetrahydrothienyl, thianyl, thiepanyl, aziridinyl, azetidinyl, pyrrolidinyl, piperidinyl, azepanyl, pyrrolyl, pyrrolinyl, pyrazolyl, pyrazolinyl, pyrazolidinyl, imidazolyl, imidazolinyl, imidazolidinyl, pyridyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, and the like. Exemplary unsubstituted heterocyclyl groups include $C_{1-12}$, $C_{1-14}$, $C_{1-18}$, $C_{1-24}$, $C_{2-12}$, $C_{2-14}$, $C_{2-18}$, $C_{2-24}$, $C_{3-12}$, $C_{3-14}$, $C_{3-18}$, or $C_{3-24}$ heterocyclyl including one or more heteroatoms, such as N, O, S, Si, P, and halo.

By "hydroxyl" is meant —OH.

By "hydroxyalkyl" is meant an alkyl group, as defined herein, substituted by one to three hydroxyl groups, with the proviso that no more than one hydroxyl group may be attached to a single carbon atom of the alkyl group and is exemplified by hydroxymethyl, dihydroxypropyl, and the like. Exemplary hydroxyalkyl groups include (hydroxyl)$_{1-3}$-$C_{1-3}$, $C_{1-6}$, $C_{1-12}$, $C_{1-16}$, $C_{1-18}$, $C_{1-20}$, or $C_{1-24}$ hydroxyalkyl groups.

By "perfluoroalkyl" is meant an alkyl group, as defined herein, having each hydrogen atom substituted with a fluorine atom. Exemplary perfluoroalkyl groups include trifluoromethyl, pentafluoroethyl, etc. Exemplary perfluoroalkyl groups include $(CF_2)_n CF_3$ groups, where of is an integer from 0 to 24.

By "salt" is meant an ionic form of a compound or structure (e.g., any formulas, compounds, or compositions described herein), which includes a cation or anion compound to form an electrically neutral compound or structure. Salts, including pharmaceutically acceptable salts, are well known in the art. For example, non-toxic salts are described in Berge S M et al., "Pharmaceutical salts," *J. Pharm. Sci.* 1977 January; 66(1):1-19; and in "Handbook of Pharmaceutical Salts: Properties, Selection, and Use," Wiley-VCH, April 2011 (2nd rev. ed., eds. P. H. Stahl and C. G. Wermuth. The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

By "sulfonate" is meant $-OSO_2-R^{S1}$, where RS1 is an organic moiety (e.g., optionally substituted alkyl, haloalkyl, aryl, alkaryl, Other features and advantages of the invention will be apparent from the following description and the claims.

where ε controls the strength of the inter-particle attraction, r is the inter-particle separation, $r_0$ is the particle radius, and σ is set to $0.25r_0$.

Figure 29:
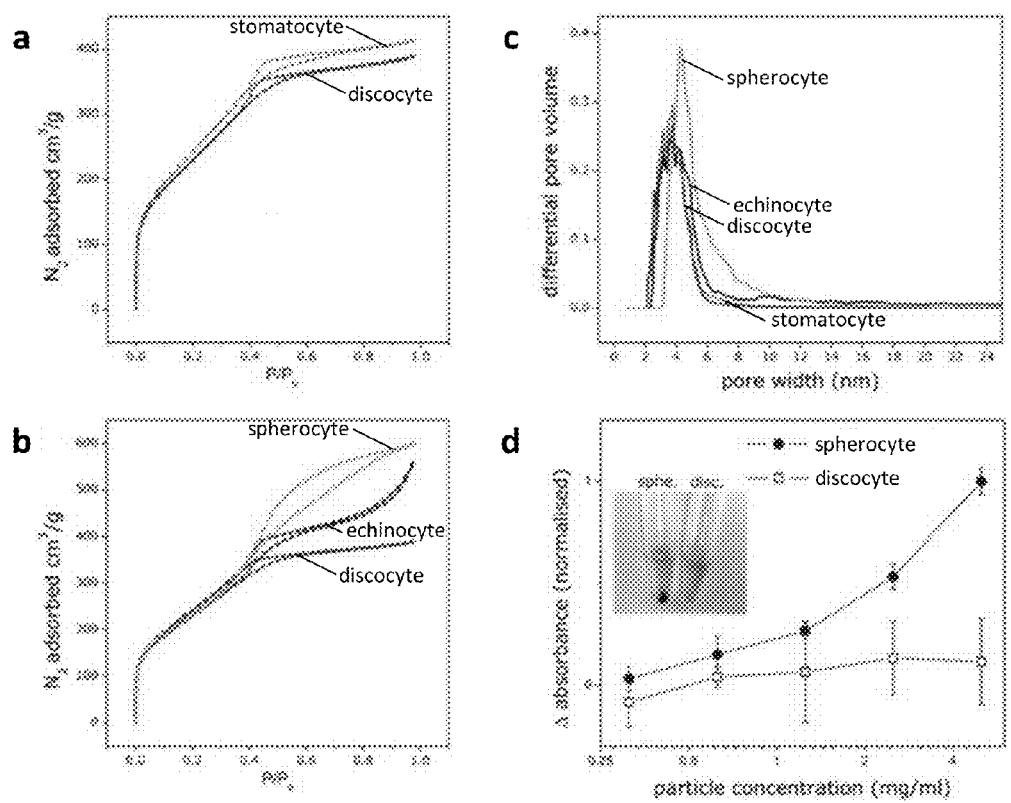

FIG. 29 shows characterization studies of calcined Si—RBC replicas using $N_2$ physisorption and absorption at 409 nm. Provided are (a) $N_2$ sorption isotherms of calcined Si—RBC replicas that are stomatocytes or discocytes; (b) $N_2$ sorption isotherms of calcined Si—RBC replicas that are spherocytes or echinocytes, where data for discocytes are provided for comparison with FIG. 29a; (c) DFT pore size distribution calculated from the isotherms; and (d) a graph showing differential loading of myoglobin into spherocytes versus discocytes, as shown by normalized absorbance difference of the supernatant (error bars indicate the standard deviation from triplicate measurements). Normalized absorbance is provided as Δabsorbance=$[(A_0-A_{30\ min})/A_0]$, where $A_0$ was the baseline absorbance and $A_{30\ min}$ was the measured absorbance recorded 30 minutes after loading. The inset in (d) shows pelleted particles in myoglobin solution, where loading is visible for spherocyte particles but not for discocyte particles.

Figure 30:
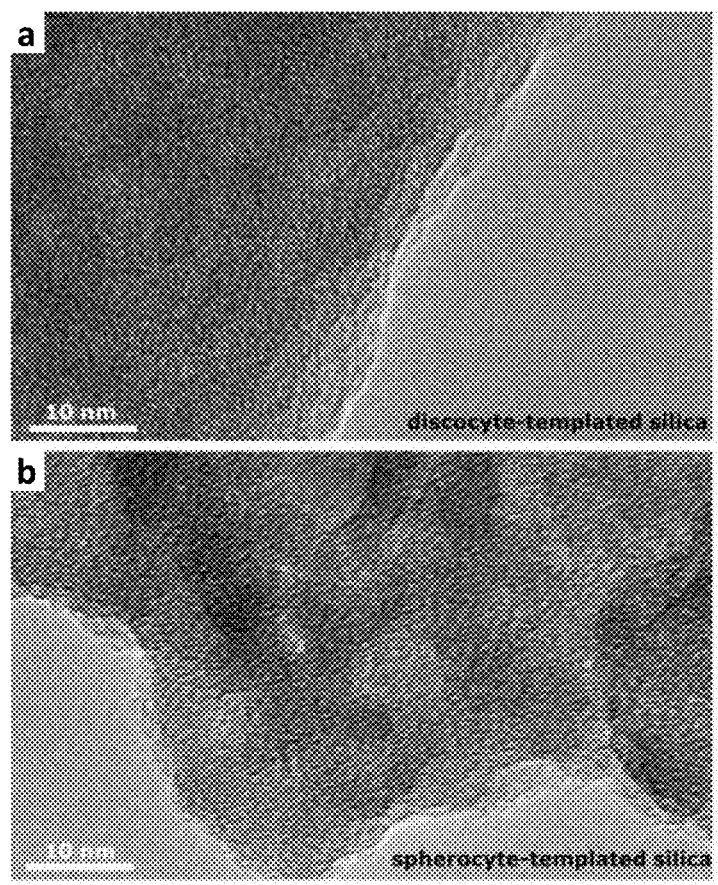

FIG. 30 shows transmission electron microscopy (TEM) images of crushed calcined Si—RBC replica particles. Provided are images of (a) discocyte-templated particles and (b) spherocyte-templated particles, which possess amorphous silica structure with relatively uniform granularity.

Figure 31:
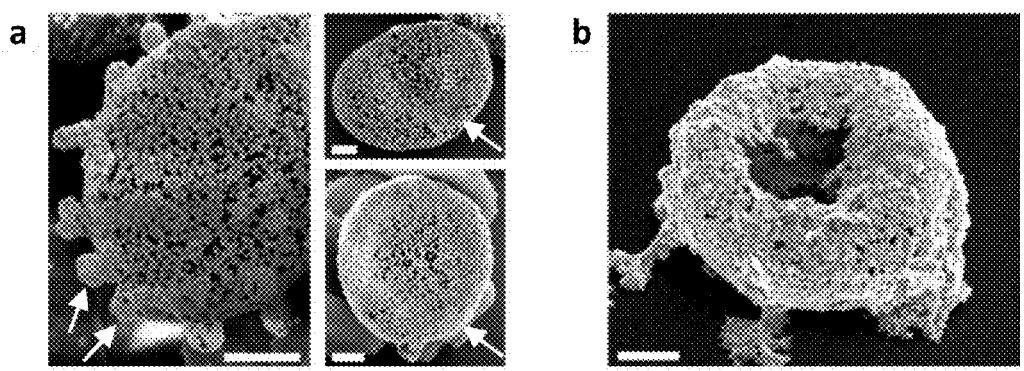

FIG. 31 shows Si—RBC composites and replicas having platinum nanoparticles (PtNPs). Provided are (a) SEM images of PtNP growth on Si—RBCs, which indicated high PtNP density on regions of positive curvature (white arrows) compared to regions of negative curvature, such as the center of the discocyte; and (b) an SEM image of a Si—RBC replica, in which PtNP-covered Si—RBC composites were treated with acid (buffered HF) to dissolve the silica template, which created a void in regions of less PtNP density. Scale bars are 1 μm.

Figure 32:
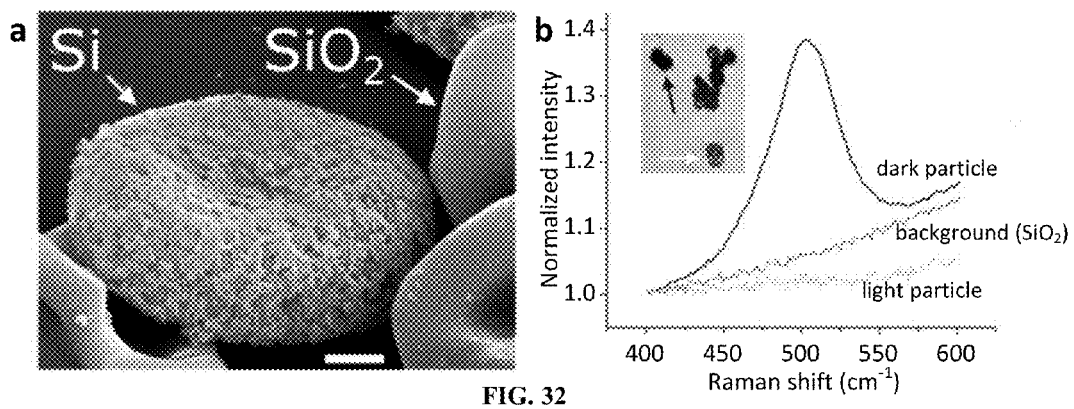

FIG. 32 shows a silicon replica formed from a Si—RBC reduced to silicon using magnesiothermic reduction. Provided are (a) an SEM image of the silicon replica, where the granular morphology indicates dissolution of the magnesium oxide phase that is a product of the reaction (scale bar, 1 μm); and (b) a graph showing Raman spectra (532 nm excitation) of silicon particles, in which verification of silicon reduction was indicated by the peak centered at ~500 $cm^{-1}$ acquired from the dark particle.

Figure 33:
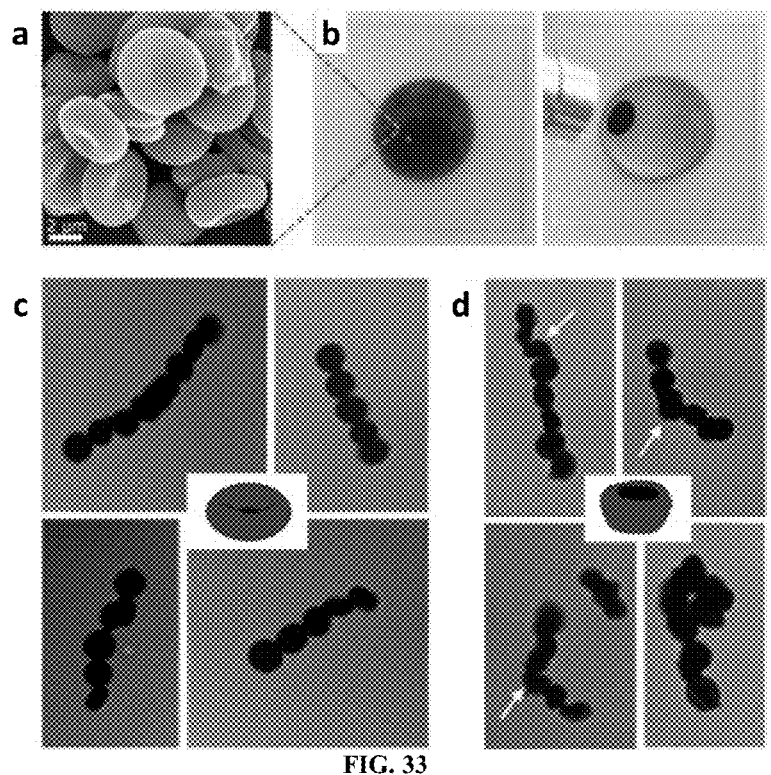

FIG. 33 shows magnetic Si—RBC particles. Provided are (a) an SEM image of magnetic silica composite discocyte particles following iron infiltration and pyrolysis; (b) a photograph of a droplet of water containing magnetic particles, which renders the resultant solution as being opaque; and (c) a photograph of the droplet in (b) during exposure to a magnetic field, which results in aggregation of the magnetic particles. Also shown are photographs of particles in the absence of an external magnetic field, which displayed the effect of particle geometry on magnetic dipole-dipole interactions between the particles. As seen in (c), magnetic discocyte particles self-assembled into linear chains and (d) magnetic stomatocytes particles self-assembled into kinked chains (white arrows indicate kinking loci).

Figure 34:
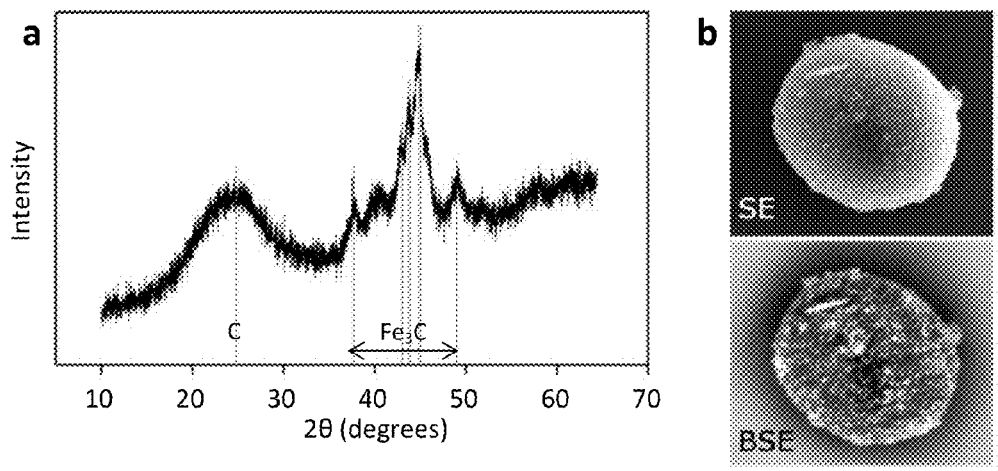

FIG. 34 shows properties of magnetic Si—RBC particles. Provided are (a) an XRD spectrum of mag-RBCs indicating the presence of iron carbide ($Fe_3C$), in which peaks for $Fe_3C$ and the peak for graphite with a mixed carbide phase (e.g., iron and silicon carbide) are labeled in the graph; and (b) secondary image (SE) and back-scattered electron (BSE) SEM images of magnetic Si—RBCs showed metallic phase separation (indicated by the light speckles in the BSE image), which are regions higher in iron content (~60% atomic percentage as measured using EDS; indicating elemental iron or iron carbide) versus the dark regions.

Figure 35:
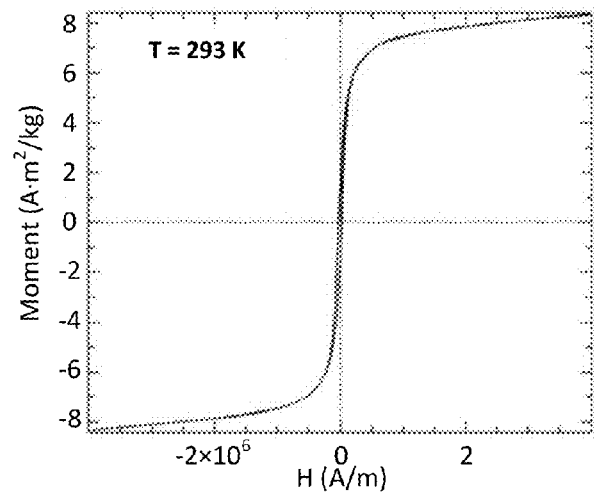

FIG. 35 shows the magnetic response of magnetic Si—RBCs with a magnetic saturation of $\sigma_{sat}$=8.34 ($A \cdot m^2/kg$), which indicated an $Fe_3C$ content of approximately 6% (assuming $Fe_3C$ is the dominant magnetic responsive component with a $\sigma_{sat}$~140 $A \cdot m^2/kg$). The slight hysteresis indicated a weakly ferromagnetic material.

Figure 36:
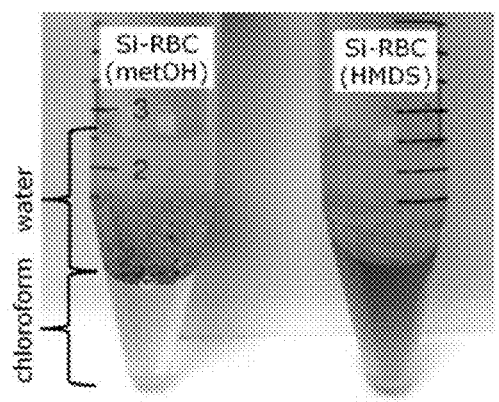

FIG. 36 shows the effect of silanization on Si—RBC particles. Provided is a photograph of phase separation in a water/chloroform solution of Si—RBCs dried from methanol (metOH, left) or hexamethyldisilazane (HMDS, right). Use of HMDS rendered the surface of the particles to be more hydrophobic, thereby providing particles that preferentially partitioned into the chloroform phase (lower, more dense phase). In contrast, non-functionalized particles (after drying from methanol) were more hydrophilic, as shown by preferential portioning into the aqueous phase (upper, less dense phase).

Figure 37:
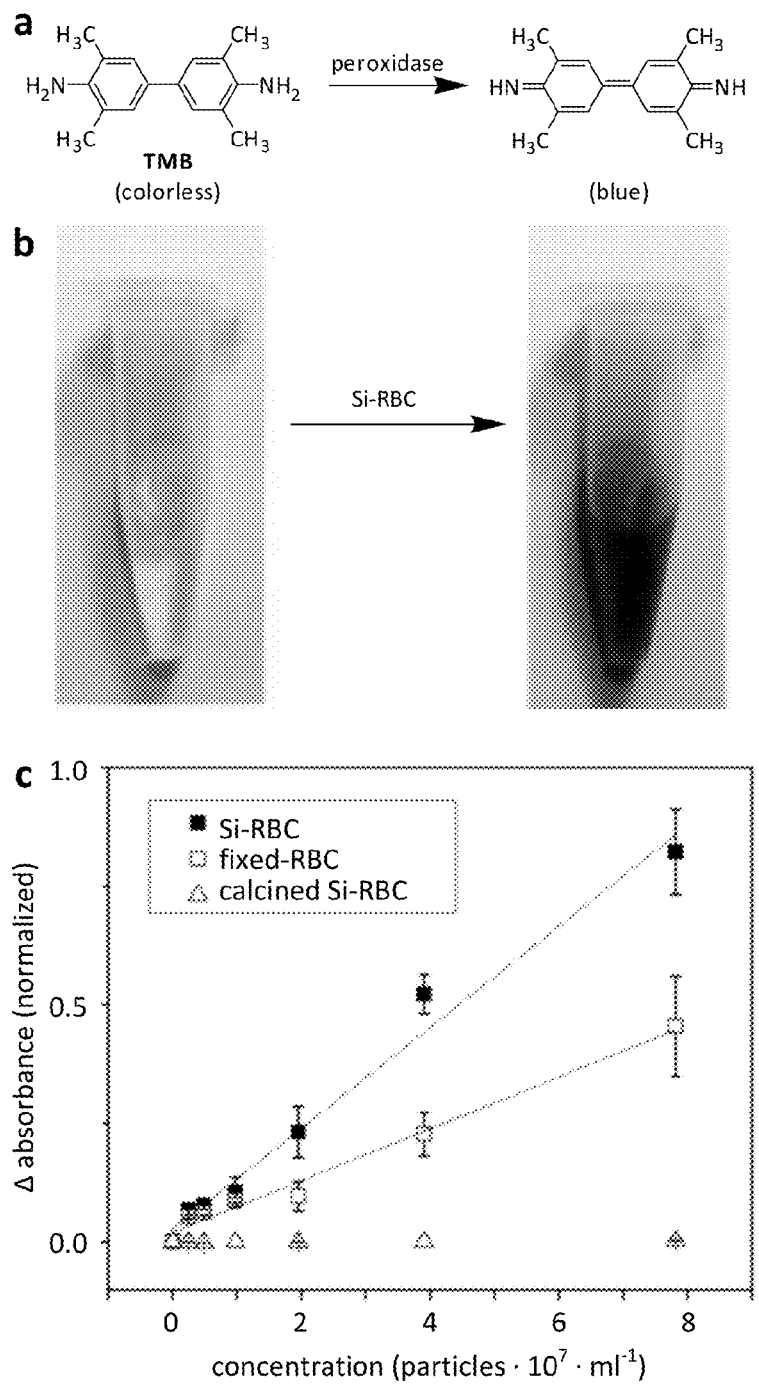

FIG. 37 shows the accessibility of proteins present within the Si—RBC composite particles. Provided are (a) a schematic of a chromogenic substrate 3,3',5,5'-tetramethylbenzidine (TMB) reacting with a peroxidase enzyme, where this reaction can be used to detect peroxidase activity of Si—RBCs by measuring the change in absorbance at 405 nm; (b) a photograph of a solution of TMB after adding Si—RBC particles, resulting in a blue color that can be quantified by an increased absorbance at 405 nm; and (c) a graph showing substrate conversion following 10 minutes of incubation, as measured by the increase in absorbance as a function of concentration. Absorbance is provided as Δabsorbance= $[(A_{10\ min.}-A_0)/A_0]$, where $A_0$ was the baseline absorbance and $A_{10\ min.}$ was the measured absorbance at 405 nm recorded 10 minutes after loading. As can be seen in (c), Si—RBCs displayed increased activity over fixed RBCs (in 4% formaldehyde) that were not subjected to silicification. Furthermore, calcined particles exhibited no peroxidase activity.

DETAILED DESCRIPTION OF THE INVENTION

The present invention relates to methods of forming silica composites and resultant replicas, as well as structural constructs obtained from such methods. In particular, the methods and constructs herein include the use of biological samples, which serve as a structurally-rich template having both internal and external surfaces capable of supporting a silica nanolayer. These surfaces are not disturbed by the silica precursors (e.g., silicic acid and related compounds) but preserved by the nanolayer(s). In some embodiments, the extensive and conformal nature of the deposited nanolayers allow the underlying biological sample to be removed or pyrolyzed without harming the structural details captured by the nanolayers. Additional details on the constructs and methods of the invention follow.

Constructs (Composites and Replicas) and the Silification Process

The present invention relates to a construct having one or more nanolayers formed on internal and/or external surfaces of a biological source (e.g., a cell, a tissue, an organ, etc.).

Figure 1A:
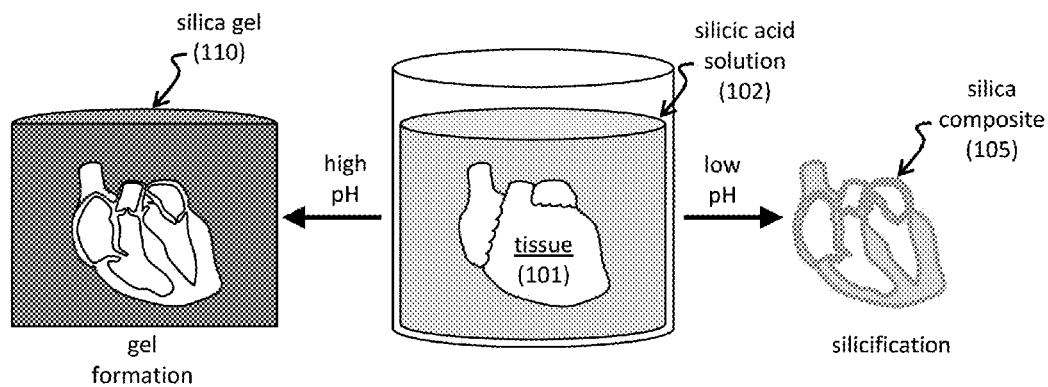
FIG. 1A-1C shows schematics of an exemplary silica bioreplication (SBR) process to provide silica composites. Provided are (A) the effect of pH on silification and the formation of the silica composite 105, (B) the result of silification in forming one or more silica nanolayers 1101, 1102 in the composite 1100 having an internal void (i), and (C) an exemplary chemical formula for a silicic acid in a silicic acid solution 1220.
Figure 1B:
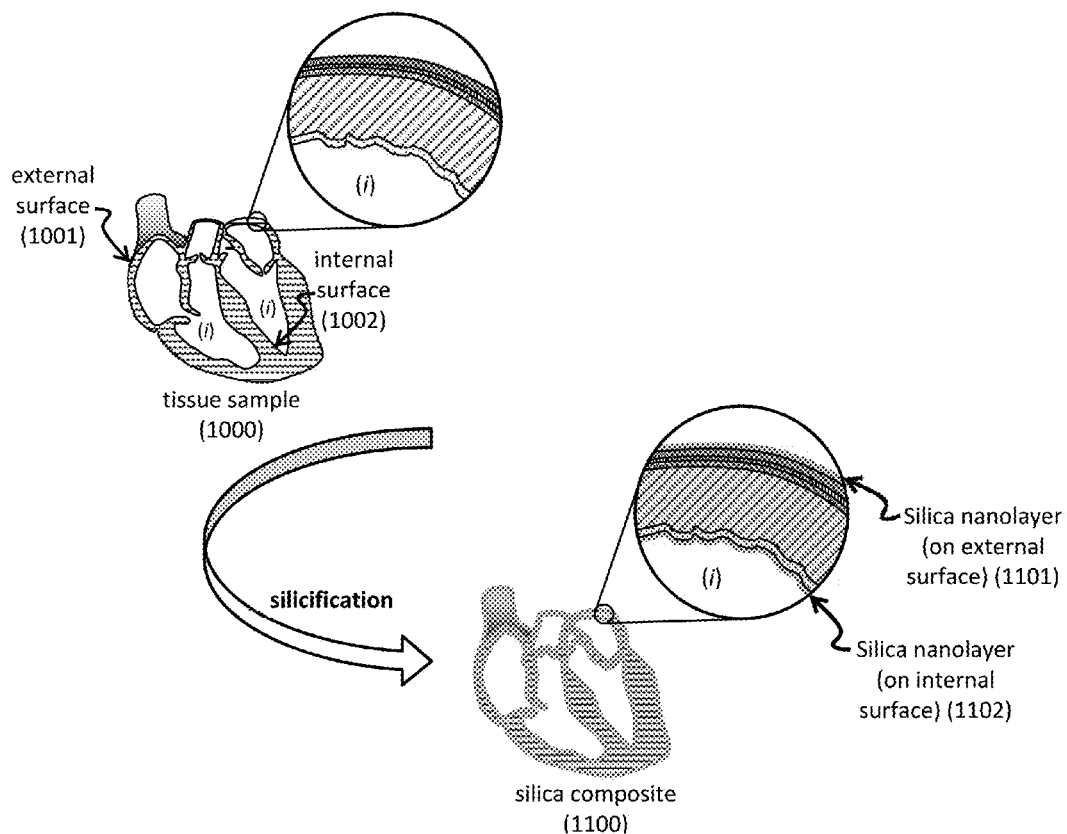

In one non-limiting embodiment, the construct is formed by placing a tissue source 101 in a silicic acid solution 102 under low pH conditions (FIG. 1A). This reaction condition provides a self-limiting condition in which the silicic acid chemical compound does not form a gel in solution but, instead, allows these silicic acid compounds to deposit on nanostructures and microstructures located on external surface(s) 1001, internal surface(s) 1002, or portions thereof, of the tissue source 1000 (FIG. 1B). When silicic acid compounds are in close proximity to cellular and protein surfaces, the resulting atomic-scale and/or nano-scale interactions provide silica nanolayers on the internal and/or external surfaces 1101,1102, or portions thereof. This process is termed silification or silica bioreplication (SBR) and provides a silica composite 105,1100.

The silification reaction is pH-dependent. For instance, under low pH (e.g., a pH less than about 7), the tissue undergoes silicification, thereby forming a silica composite 105 (FIG. 1A). However, under high pH conditions (e.g., a pH greater than about 7), the silicic acid compound forms a silica gel monolith 110 and does not form a silica composite.

There are at least two critical, structural differences between a silica composite and a silica gel monolith. First, a silica composite includes silica layers deposited within the tissue, whereas a silica monolith includes silica components surrounding only the external surface of the tissue. Second, the silica composite includes nanolayers of silica, whereas the silica monolith includes a gel of silica. Due to these structural and compositional differences, a silica composite captures detailed nanoscopic and microscopic cellular and protein structures of the underlying biological tissue, whereas the silica gel monolith possesses no such details. Thus, the constructs of the present invention are distinct from monoliths or encapsulated structures, in which a tissue is embedded or encapsulated in a silica gel.

In particular, such a monolith and/or an encapsulated structure is a shaped, fabricated, intractable article with a homogeneous microstructure which does not exhibit any structural components distinguishable by optical microscopy, as defined, e.g., in the International Union of Pure and Applied Chemistry (IUPAC) Compendium of Chemical Terminology, 2nd ed. (the "Gold Book") and in Alemán J et al., "Definitions of terms relating to the structure and processing of sols, gels, networks, and inorganic-organic hybrid materials (IUPAC Recommendations 2007)," *Pure Appl. Chem.* 2007; 79(10):1801-29, each of which is incorporated herein by reference in its entirety). Thus, in some embodiments, the construct of the invention is neither a monolith nor an encapsulated gel structure.

Figure 1C:
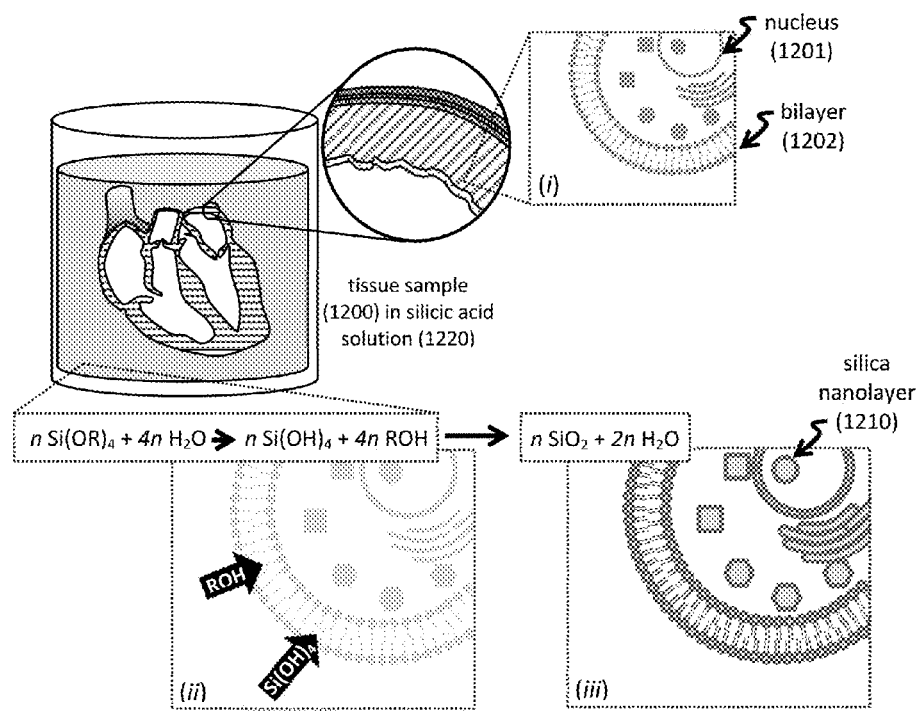

FIG. 1C provides further detail of an exemplary silification process. As can be seen, the biological sample is a tissue sample 1200 that is immersed in a silicic acid solution 1220. The tissue sample 1200 includes various cellular components, such as a nucleus 1201, a lipid bilayer 1202, as well as proteins and other cellular structures (gray geometric figures and curves) shown in the inset labeled (i) of FIG. 1C. The exemplary silicic acid solution 1220 includes a silicic acid compound (e.g., $Si(OR)_4$) and a solvent (e.g., $H_2O$), which undergoes a hydrolysis reaction to provide orthosilicic acid $Si(OH)_4$ (also a silicic acid compound) and an alcohol ROH (e.g., R is optionally substituted alkyl, or any described herein). Then, the hydrolyzed silicic acid compound (e.g., $Si(OH)_4$) condenses to form an exemplary silica nanolayer 1210 composed of $SiO_2$.

The chemical reactions of the silicic acid compounds occur on various biological interfaces and at various length scales. For instance, the hydrolysis reaction occurs generally in the bulk volume of the silicic acid solution, but the hydrolysis reaction products (e.g., $Si(OH)_4$ and ROH) enter the cells of the tissue sample (inset (ii) of FIG. 1C). In some embodiments, ROH acts as a cell permeabilizing agent, which facilitates entry of the silicic acid compounds through lipid layers and into various cellular compartments. Once within the cells, the silicic acid compounds interact with various biological interfaces, such as those present on cell structures, proteins, etc. Without wishing to be limited by mechanism, we believe that this interaction relies on hydrogen bonding with biological interfaces and amphoteric catalysis with proximal acidic/basic moieties at these biological interfaces, and that the molecularly crowded conditions present within the cell further promotes silica condensation. Thus, the resultant silica nanolayer 1210 is conformal and preserves shapes (e.g., microscale and nanoscale features) of the underlying tissue (inset (iii) of FIG. 1C).

The biological sample can be treated with one or more agents to alter the shape of the underlying biological sample. For instance, most biological samples are sensitive to external cues, such that exposing the sample to a biological or chemical agent can induce an intercellular or extracellular change that manifests as a structural change. As an example, exposure of a cell to hypertonic conditions (e.g., employing high salt concentrations) can result in osmotic stress, which manifests as shrinking to form a crenated cell. This shrunken, crenated shape can then be silicified, thereby providing a shape-encoded composite that can be further processed into a replica (e.g., any herein).

Figure 2:
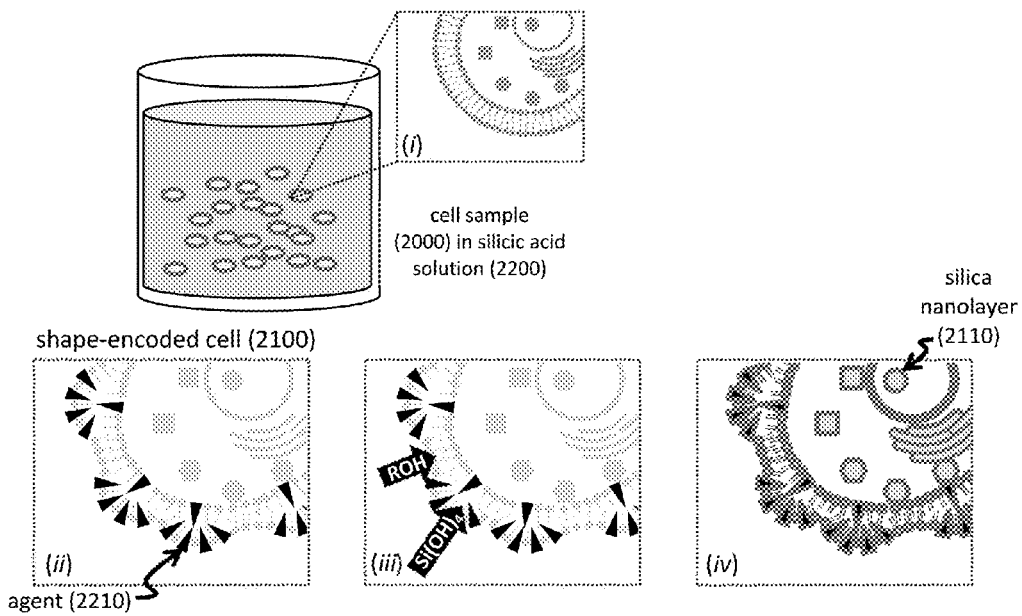
FIG. 2 shows schematics for a silification process to form silica composites from shape-encoded samples 2100.

Any useful sample (e.g., a biological sample, such as those including tissue, cells, etc.) can provide shape-encoded composites and replicas. Of course, the choice of the agent to provide the shape will depend on the type of tissue sample or cell sample, the desired alteration of either internal surfaces or external surfaces, and the desired geometry of the final shape. As seen in FIG. 2, the exemplary sample is a cell sample 2000 that is immersed in a silicic acid solution 2200. The sample 2000 includes various cellular components, such as a nucleus, a lipid bilayer, as well as proteins and other cellular structures (gray geometric figures and curves) shown in the inset labeled (i) of FIG. 2.

An agent 2210 can be employed to provide a shape-encoded cell 2100. As seen in inset (ii) of FIG. 2, the agent 2210 is selected to alter the lipid bilayer of the cell. The agent can be added either prior to or concurrent with immersing the sample in the silicic acid solution. In addition, one or more agents can be employed together in the same step or in different, subsequent steps. Next, the components of the silicic acid solution (e.g., the silicic acid compound and/or the alcohol) react with the various biological interfaces presented on and within the sample. For instance, silicic acid compound $Si(OH)_4$ and alcohol ROH react with various interfaces (FIG. 2, inset (iii)), thereby providing a silica composite having one or more silica nanolayers 2110 (FIG. 2, inset (iv)).

The silica nanolayer can have any useful dimension and composition. For instance, the silica nanolayer can be composed of predominantly $SiO_2$. In another instance, the silica nanolayer has a thickness (e.g., along an axis orthogonal to a surface, such as a plane along the external surface of the tissue) of from about 0.1 nm to about 500 nm (e.g., from 1 nm to 500 nm, 1 nm to 250 nm, 1 nm to 100 nm, 1 nm to 50 nm, 1 nm to 25 nm, 1 nm to 10 nm, from 2 nm to 500 nm, 2 nm to 250 nm, 2 nm to 100 nm, 2 nm to 50 nm, 2 nm to 25 nm, 2 nm to 10 nm, from 5 nm to 500 nm, 5 nm to 250 nm, 5 nm to 100 nm, 5 nm to 50 nm, 5 nm to 25 nm, 5 nm to 10 nm, from 10 nm to 500 nm, 10 nm to 250 nm, 10 nm to 100 nm, 10 nm to 50 nm, and 10 nm to 25 nm). In some instances, the nanolayer can be formed from another material, such as a metal, a ceramic, a semiconductor, etc., of any useful thickness (e.g., of from about 0.1 nm to about 500 nm, including any other range described herein).

The construct can have any other useful features. For instance, the construct can be mesoporous (i.e., having pores of a diameter of from about 1.5 nm to about 50 nm). In another instance, the construct is not a monolith. In yet another instance, the construct is not spherical (i.e., non-spherical). In other instances, the construct possesses stabilized enzymatic activity or stabilized protein structures, in which proteins or enzymes from the biological sample are retained in the construct.

Types of Constructs

Figure 3A:
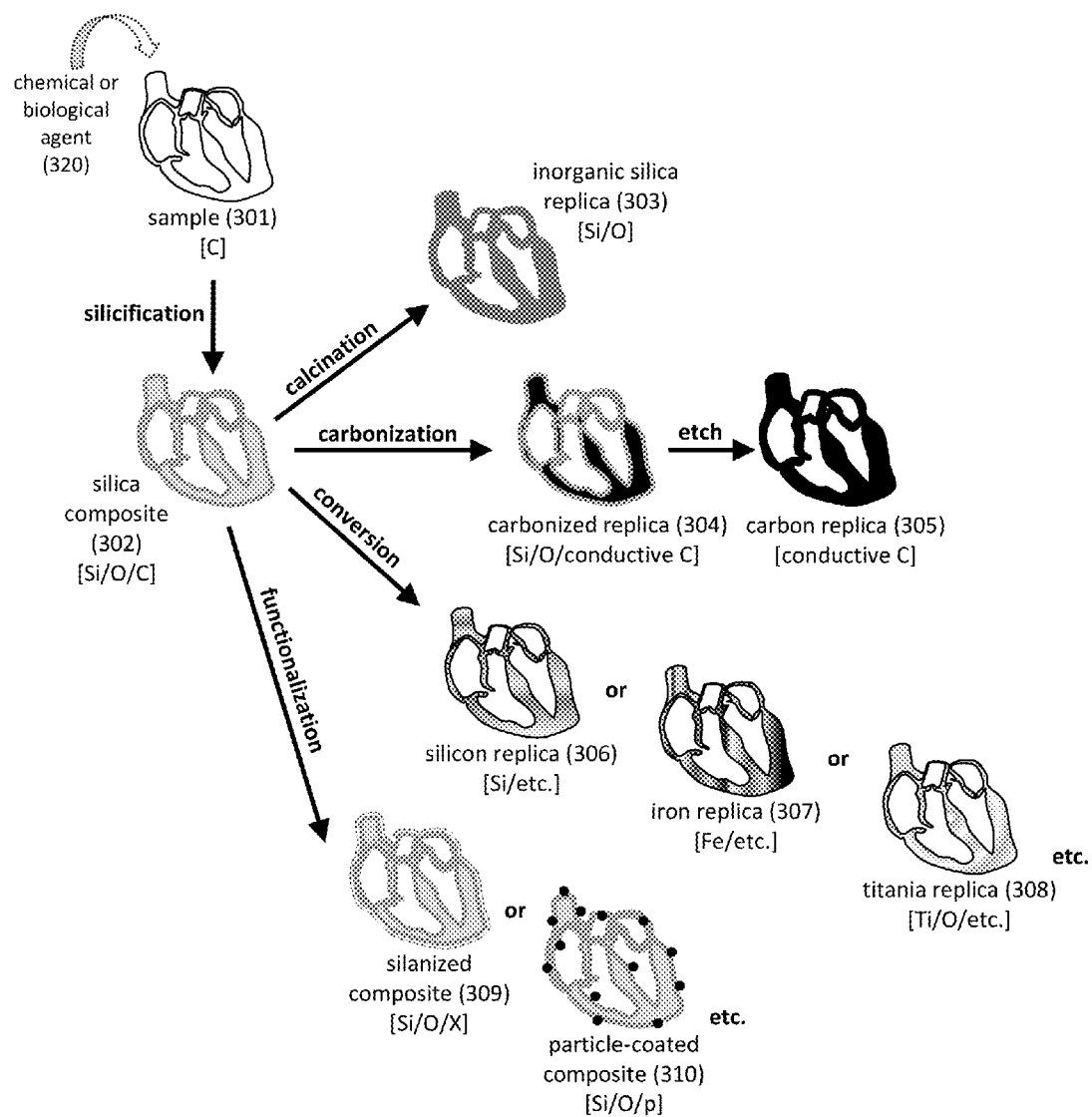
FIG. 3A-3B shows schematics of further exemplary processing conditions to provide replicas and composites. Provided are (A) processes to provide a silica composite 302, as well as various different types of other replicas and composites 303-310; and (B) a flow chart of an exemplary method 3000 of the invention.

The silification process can produce different types of constructs. Exemplary constructs include a silica composite, a functionalized composite (e.g., a silanized composite or a coated composite), or a replica (e.g., a silica replica, a carbonized replica, a carbon replica, a metal replica, a semiconductor replica, etc.). As seen in FIG. 3A, the sample 301 can be any useful biological sample and includes carbon-based or organic matter [C], such as cellular components, cells, etc.

The sample 301 undergoes silification to provide a silica composite 302 including silicon, oxygen, and carbon [Si/O/C]. As employed herein, a silica composite is a structure including both the underlying organic matter of the sample, as well as one or more silica nanolayers deposited on an external and/or internal surface, or a portion thereof, of the sample.

Prior to silification, the sample 301 can be optionally treated with an agent 320 (e.g., any herein, such as a chemical or biological agent). The agent can be used to bind particular targets within the sample, to treat one or more different cell subtypes present in the sample (e.g., such as in a tumor cells within the sample), to encode a desired shape of the sample, to form pores on the surface of the sample and/or within the sample, to label the sample, etc. When the sample is treated in this manner, the latter silification process then provides a way to store this treated state or to further analyze various structural or biochemical changes that are induced by this treatment.

The silica composite 302 can be further processed, as seen in FIG. 3A. For instance, the underlying organic matter can be removed. Alternatively, the underlying organic matter can be transformed into conductive carbon. In yet another alternative, the silica can be converted into another elemental composition, such as by any useful conversion process (e.g., by way of a displacement reaction) to provide the converted replica. Finally, the silica composite can be functionalized, such as by attaching one or more different functional groups, particles, or coating, thereby providing a functionalized replica. These alternative composites and replicas are described below.

The silica composite generally includes an underlying organic structure, and the organic matter from this structure can be removed in any useful manner to provide an inorganic silica replica. In one instance, for the removal of organic matter, the silica composite 302 can undergo calcination, i.e., exposure to high temperature conditions to decompose organic matter (e.g., conditions such as a temperature of from about 500° C. to about 600° C. in air or an oxidative atmosphere). After calcination, an inorganic silica replica 303 is formed, which is predominantly silicon [Si] and, optionally, oxygen [O].

In another instance, the underlying organic matter can be transformed into conductive carbon. For this transformation, the silica composite 302 can under carbonization or pyrolysis, where these terms are employed interchangeably, i.e., exposure to high temperature conditions that convert organic matter into carbon (e.g., conditions such as a temperature of from about 800° C. to about 1,000° C. in an inert or reducing atmosphere). After carbonization, a carbonized replica 304 is formed, which is composed of silica (silicon and oxygen) and conductive carbon [Si/O/conductive C]. Furthermore, the underlying silicon can be removed, thereby providing a carbon replica 305, which is predominantly conductive carbon [conductive C].

Complex structures formed from other materials can be useful. For instance, such other materials can include metals (e.g., noble metals, metal carbides, metal oxides, etc.), semiconductor materials (e.g., silicon), ceramics, and magnetic materials. To form converted replicas having such materials, the silica composite's material can be converted into other materials by any useful reaction (e.g., displacement reactions, such as gas/solid or liquid/solid displacement reactions or metathetic gas/solid displacement reactions, such as with halide gases; oxidation reactions, such as oxidation-reduction displacement reactions; magnesiothermic reduction reactions; carbothermal reduction reactions; hydrothermal reactions; reactive metal reactions, such as with molten metals, including amalgams, oxides, and mixtures thereof; etc.). Exemplary reactions are described in Sandhage K H, "Materials 'alchemy': Shape-preserving chemical transformation of micro-to-macroscopic 3-D structures," *JOM* (*Journal of The Minerals, Metals & Materials Society* (*TMS*)) 2010 June; 62(6):32-43, which is incorporated herein by reference in its entirety.

Any useful converted replica can be formed. In one instance, the silica composite 302 is reduced to a silicon replica 306 [Si/etc.] using magnesiothermic reduction, in which silica is exposed to magnesium vapor in order to conduct a net magnesiothermic displacement reaction. This reactions results in the formation of magnesia (MgO) and silicon (Si), in which the magnesia phase can be removed (e.g., with acid treatment) to retain the Si phase. Alternatively, the reduction reaction can be continued in excess magnesium vapor to form a magnesium-silicon alloy liquid, where this liquid then flow out of the reacted composites to yield magnesium oxide (MgO) replicas.

In another instance, the silica composite 302 is used as a carbon source for the formation of an iron or iron carbide replica 307 [Fe/etc.], in which iron (II) or (III) precursors (e.g., iron (II) acetate or iron (III) nitrate) undergo carbothermal reduction to form iron carbide- or iron-based replicas. In yet another instance, the silica composite 302 is exposed to a metal halide gas, thereby forming a metal oxide replica by way of halide displacement reactions. A titania (titanium oxide) replica 308 can be formed in such a manner.

Any of the composites or replicas herein can be further functionalized. In one instance, the composite or replica is functionalized by use of a silanizing agent (e.g., an agent having the structure of $(R^L)_3SiR^M$, where each $R^L$ is, independently, H, alkyl, hydroxyl, halo, or alkoxy, and $R^M$ is a functional moiety, as described herein). When a composite is employed, the silica surface of the composite 302 can be used as a handle to support silane chemistry, thereby providing a silanized composite 309. Optionally, the silica surface can first be oxidized (e.g., by plasma) prior to silanization. In another instance, the composite or replica is functionalize by use of one or more particles (e.g., a nanoparticle, such as any herein), thereby providing a particle-coated composite 310. In yet another instance, the composite or replica includes a coating (e.g., such as by electroless deposition or sputter-coating, e.g., of a noble metal, such as Au, Ag, Pd, etc.; or by spin-coating with a polymer) with optional subsequent dissolution of the silicon (e.g., in KOH or NaOH), thereby providing a coated composite.

Any of the post-silification steps herein can be combined to form a useful composite or replica. For instance, the functionalized composite (e.g., silanized, particle-coated, or coated composite) can be further treated (e.g., by calcination, carbonization, etching, and/or conversion) to provide a functionalized replica. In this way, the surface of a composite can be functionalized in any useful manner, and the underlying silica and/or organic matter can be transformed (e.g., into silicon, conductive carbon, a metal, a semiconductor, a ceramic, etc.) and/or removed (e.g., by etching silica or by calcinating organic matter). In a similar manner, any replica herein can be further functionalized (e.g., using a silane, a particle, a coating, etc.) to provide a functionalized replica. For instance, a silicon replica can be functionalized with a silane (e.g., to change the hydrophobicity of the replica) and then optionally coated with a particle (e.g., to impart binding and/or fingerprinting capabilities of the replica).

Figure 4:
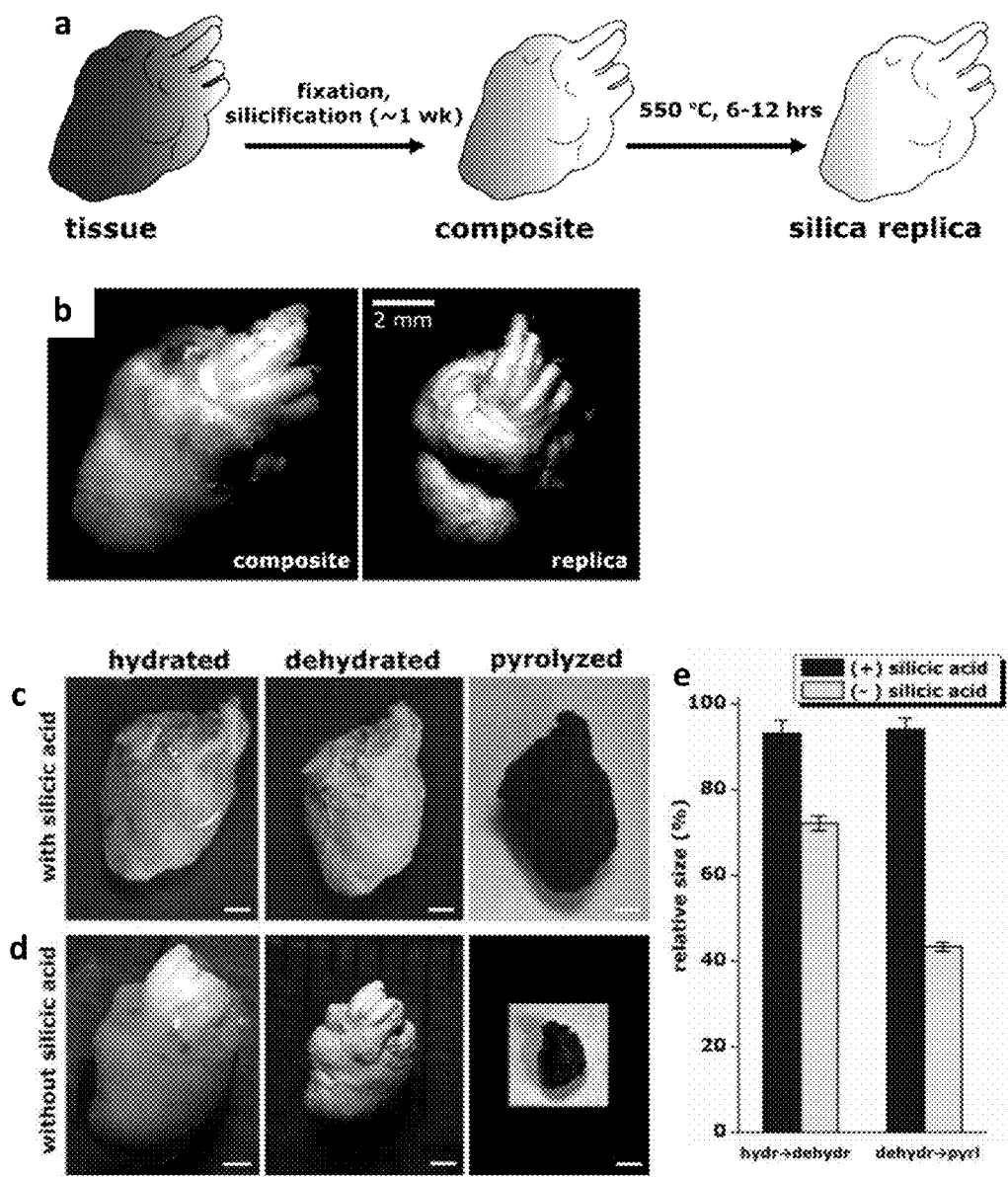
FIG. 4 shows the effect of the SBR process for an avian heart. Provided are (a) a schematic of the SBR process for a heart from a 17-day-old avian embryo and (b) the resultant SBR composite (left) and the calcined silica replica (right). The lower heart chamber shows partial collapse following calcination. Provided are images showing size comparisons of hydrated, dehydrated, and pyrolyzed specimens, in which the specimen is (c) a silicified heart or (d) a non-silicified heart. Also provided is (e) a graph showing the relative size changes following hydration to dehydration and dehydration to pyrolysis, based on comparison of multiple line measurements from these images. Scale bars include (b) 2 mm; and (c,d) 1 mm.

As seen in FIG. 4, the composites and replicas of the invention preserve the structural details of the underlying biological source. FIG. 4a shows an exemplary method including a first step of fixatating and then silicifying the tissue to provide the silica composite (FIG. 4b, left), followed by calcination at about 550° C. to provide the silica replica (FIG. 4b, right). Carbonized replicas not only displayed shape-preservation but also provided a conductive structure for further high-energy electron microscopy studies (see, FIGS. 9-12).

The silicified tissue maintained its size when provided as a hydrated silica composite, a dehydrated silica composite, and a pyrolyzed (carbonized) replica (FIG. 4c). In contrast, when the tissue is not silicified, dehydration and carbonization drastically changes the size of the underlying tissue. For instance, non-silicified tissues reduced in size when dehydrated, and then further reduced in size to when pyrolyzed (FIG. 4d). As can be seen, the silicified tissue maintained its size at about 90% (as compared to original heart size) even after pyrolysis, but the non-silicified tissue drastically shrank to about 40% (as compared to original) after pyrolysis (FIG. 4e). In addition, non-silicified tissue lost all underlying biological structures and features (see, FIG. 8).

Figure 5:
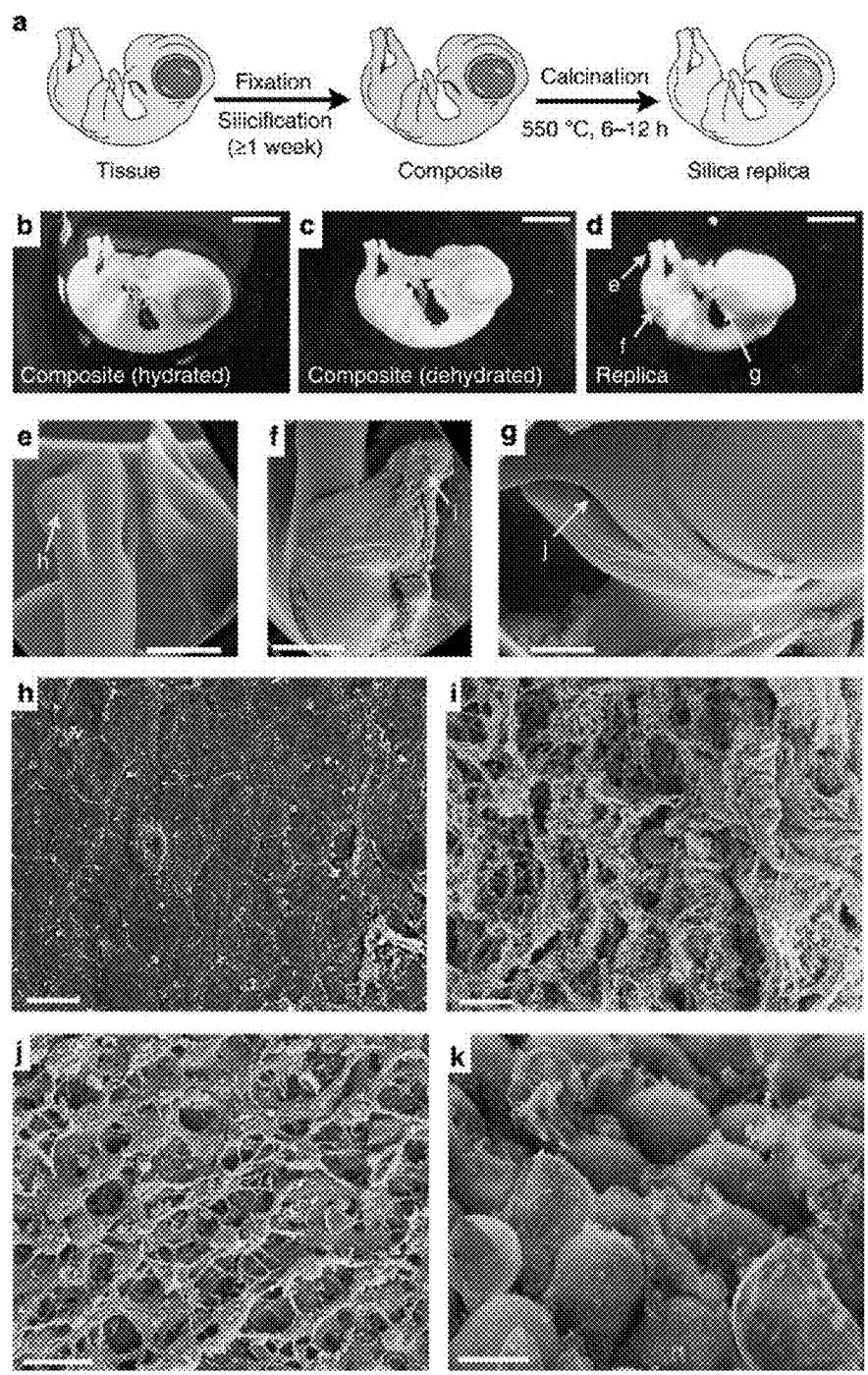
FIG. 5 shows SBR of a 9-day-old chicken embryo. Provided are (a) a schematic showing the SBR process on an intact chicken embryo, as well as photographs of the embryo composite either (b) before hydration or (c) after dehydration. Also shown is the composite after calcination at 500° C., thereby producing (d) a silica replica. As can be seen, the embryo showed minimal shrinkage or shape change following dehydration and calcination. Provided are (e-g) magnified images of the replica, including images of the (h) surface dermal tissue, (i) subsurface cellular connective tissue, (j) subsurface cells of the ocular membrane, and (k) surface cells of the developing tongue. Scanning electron microscopy (SEM) images were acquired following sputter coating of Au/Pd to a thickness of 10 nm. Arrows and letters indicate the location of the labeled magnified images. Scale bars include (b-d) 5 mm; (e-g) 1 mm; (h, j) 10 µm; (i) 20 µm; and (k) 5 µm.
Figure 7:
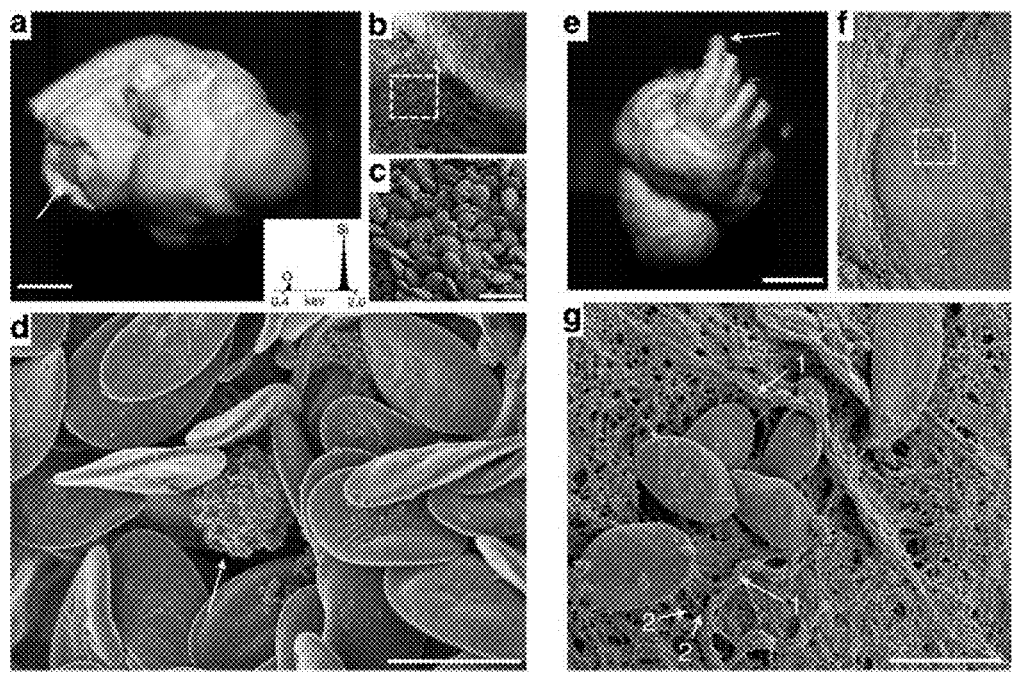
FIG. 7 shows structural preservation of deep tissue in silica replicas of chicken embryos. Provided are SEM images of (a) a silica replica of a 4-day-old chicken embryo fractured post silification and subsequently calcined, where the inset shows an energy-dispersive X-ray spectrum (EDS) of the silica replica. The arrow in (a) shows the exposed internal tissue magnified via SEM in (b) and further magnified in (c). Also provided are (d) a silica replica of a white blood cell (arrow) nestled among SBR red blood cells within a blood vessel in chicken embryo liver; (e) a silica replica of heart from a 17-day-old chicken embryo; (f) the surface of a blood vessel (denoted by arrow in panel (e)); and (g) a further magnified SEM image showing red blood cell replicas bound to presumable elastin and collagenous fibers with diameters spanning microns (indicated by "1") to tens of nanometers (indicated by "2," ~60 nm-80 nm fibers). SEM images were acquired following sputter coating of Au/Pd to a thickness of 10 nm. Scale bars include (a) 1 mm; (b,c) 20 µm; (d) 10 µm; and (e) 2 mm.

Constructs can be formed from organs (as in FIG. 4b) or even more complex structures, such as entire organisms. FIG. 5 shows silification of a chicken embryo to provide a silica composite and a silica replica. The replica, formed after calcination at about 550° C., provided structural detail of various types of tissue in the forming embryo, including dermal tissue, connective tissue, and ocular tissue. Deeply embedded biological structures were also preserved. For instance, red blood cells, elastin protein fibrils, and collagen protein fibrils within silicified embryos and hearts were preserved (FIG. 7).

Finally, the constructs can be useful for fingerprinting of agents in the interior of the constructs of the invention. As described herein, the silification process preserved the three-dimensional context of the underlying biological sample. When a test agent (e.g., a therapeutic agent or label, such as any herein) is introduced into the tissue, then the silification process can be used to provide the location of the test agent within the tissue (see, FIG. 14). Such contextual detection techniques would be useful to understand the diagnostic and therapeutic potential of the test agent.

Methods for Preparing Composites and Replicas

Figure 3B:
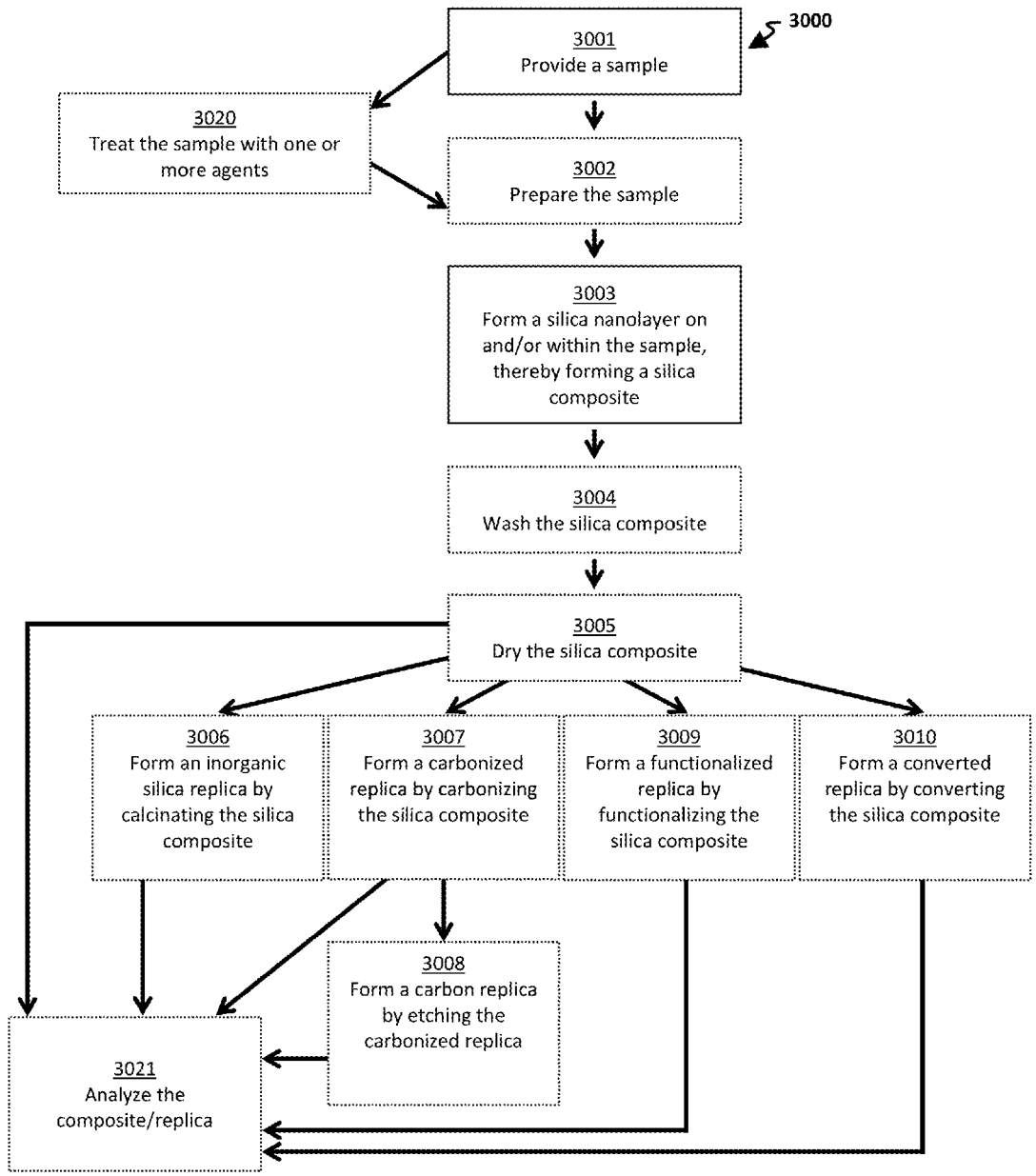
Figure 16A:
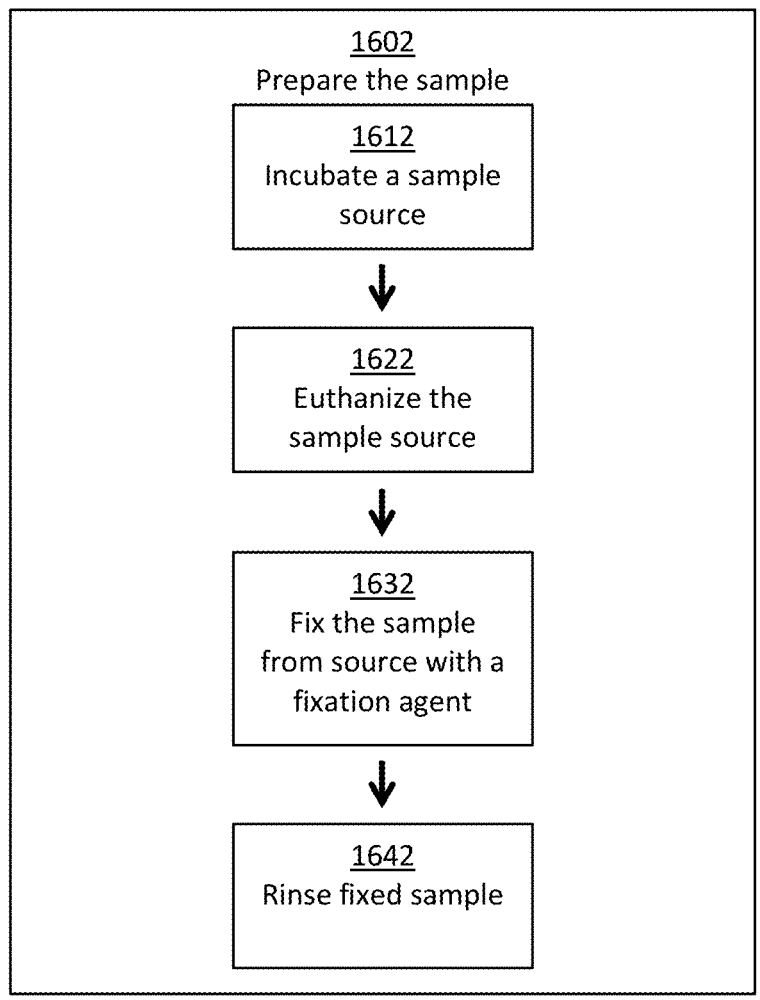
FIG. 16A-16E shows flow charts of exemplary steps in a method of the invention. Provided are (A) an exemplary step 1602 for preparing a sample, (B) an exemplary step 1603 for forming a silica nanolayer, (C) an exemplary step 1604 for washing a silica composite, (D) an exemplary step 1606 for forming an inorganic silica replica, and (E) an exemplary step 1607 for forming a carbonized replica.
Figure 16B:
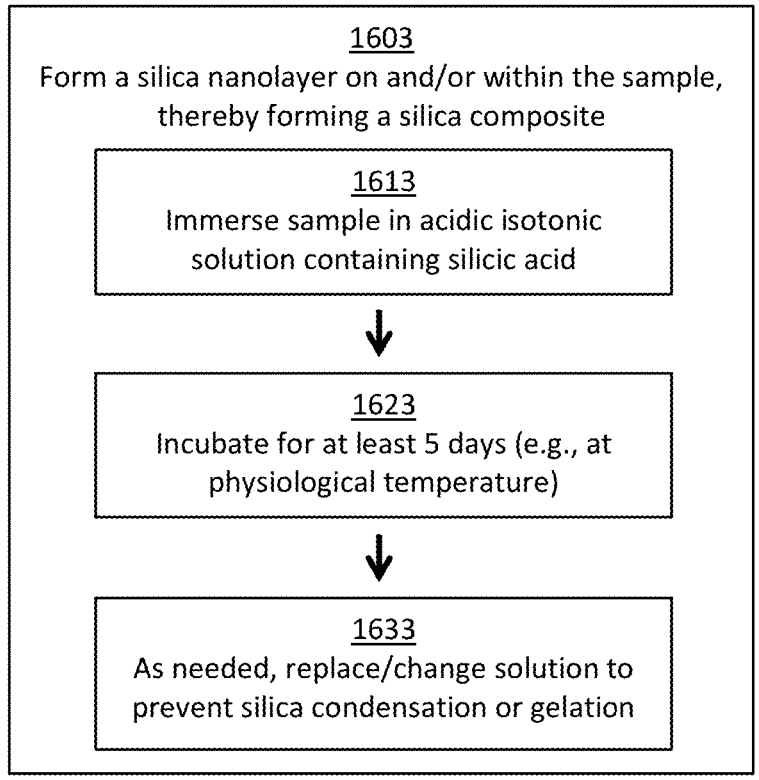

The constructs can be formed by employing any useful method that includes the silification process. FIG. 3B shows one exemplary method 3000. In general, the method 3000 includes the step 3001 of providing a biological sample and the silification step 3003 of forming one or more silica nanolayers on and/or within the sample, thereby forming a silica composite. The method can include additional optional steps, as described herein. As seen in FIG. 16B, the silification step 1603 can include an immersion step 1613 of immersing the sample in a silicic acid solution, such as any herein; an incubation step 1623 of incubating the sample for a time sufficient to provide penetration of the silicic acid compounds into the tissue and/or its cells (e.g., for about three or more days, such as of from about one week to three weeks) at any useful temperature (e.g., room temperature, physiological temperature, etc.); and an optional replacement step 1633 of replacing or changing the silicic acid solution, as needed, to prevent silica condensation or gelation within the silicic acid solution. Furthermore, the volume of the silicic acid solution can be in excess of the volume of the sample, such as a volume ratio of from about 1:10 to about 1:100 for tissue: solution (e.g., from 1:10 to 1:50, such as about 1:20).

One optional step includes a treatment step 3020 in which the sample is treated with one or more agents before, during, and/or after the preparing step 3002. The treatment step 3020 can be employed to understand how a particular agent (e.g., chemical or biological agent, such as any herein) affects the physical conformation or structure of the biological cell sample. For instance, if the tissue includes a cancerous growth, then the agent can be an anti-cancer agent; and the methods herein can be employed to form a silica composite or replica that accurately captures the location of the anti-cancer agent and, therefore, determines whether the anti-cancer agent effectively targets the cancerous cells. In another instance, the treatment step 3020 employs an agent that alters one or more physical characteristics of the silica nanolayer, such as thickness, porosity, continuity, etc. In yet another instance, the treatment step 3020 employs an agent that alters the shape of the sample, thereby providing a shape-encoded sample that can be silicified or processed (e.g., as described herein) to provide a composite or a replica. In one example, the shape-encoded sample includes a shape-encoded cell (e.g., a blood cell encoded by employing an amphipath). Additional details on treatment steps are described herein (e.g., see FIG. 21a,b)

Another optional step includes a sample preparation step 3002. In particular, this step can include one or more additional sub-steps that assist in stabilizing and/or preparing the tissue, such as treating the tissue with one or more fixative reagents, permeabilization reagents, etc. As seen in FIG. 16A, an exemplary sample preparation step 1602 includes an incubation step 1612 of incubating the biological sample source (e.g., an organism); a euthanization step 1622 of euthanizing the source; a fixation step 1632 of fixating the sample from the source with a fixative reagent, such as any herein; and a rinse step 1642 of rinsing the fixed sample with a solvent, e.g., any aqueous solvent herein.

Figure 16C:
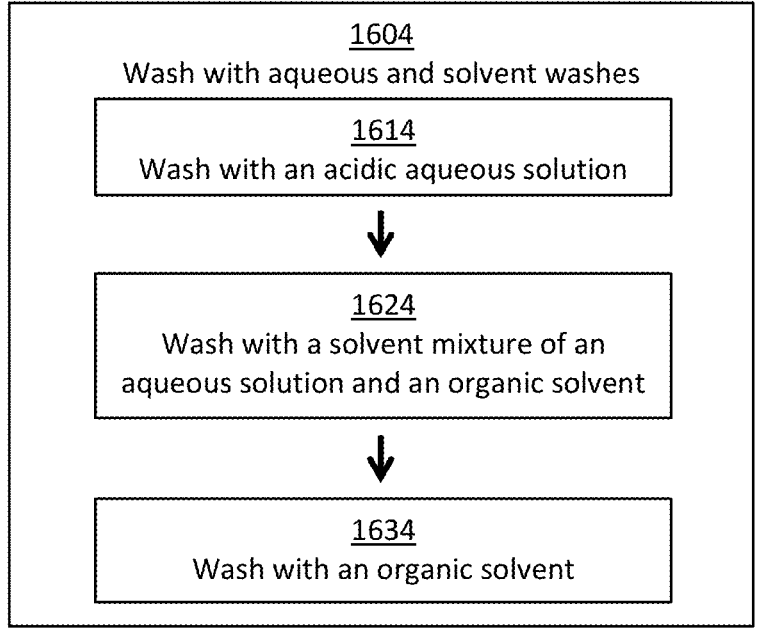

After forming the silica composite, one or more washing and/or drying steps 3004, 3005 can be conducted. In some embodiments, the washing step 3004 is conducted by employing successive wash conditions including an aqueous solvent, a mixture of an aqueous solvent with an organic solvent, and an organic solvent (e.g., an organic volatile solvent that assists in the drying step). Exemplary aqueous solvents include water (e.g., at any useful pH, such as of from about 1 to 4), a buffer (e.g., a phosphate buffered saline), an isotonic solution (e.g., about 300 mOsm/L), etc.; and exemplary organic solvents include an alcohol (e.g., ROH, such as methanol and ethanol), acetone, etc. FIG. 16C provides an exemplary washing step 1604 including a first wash step 1614 with an acidic aqueous solution (e.g., water at a pH of from about 0.5 to about 5, including any range described herein); a second wash step 1624 with a solvent mixture (e.g., of an acidic aqueous solution, such as that employed in the first wash step, and an organic solvent); and a third wash step 1634 with an organic solvent (e.g., any herein). The drying step 3005 can be conducted to dehydrate the silica composite, thereby forming a dry powder containing particles of silica composites.

Figure 17:
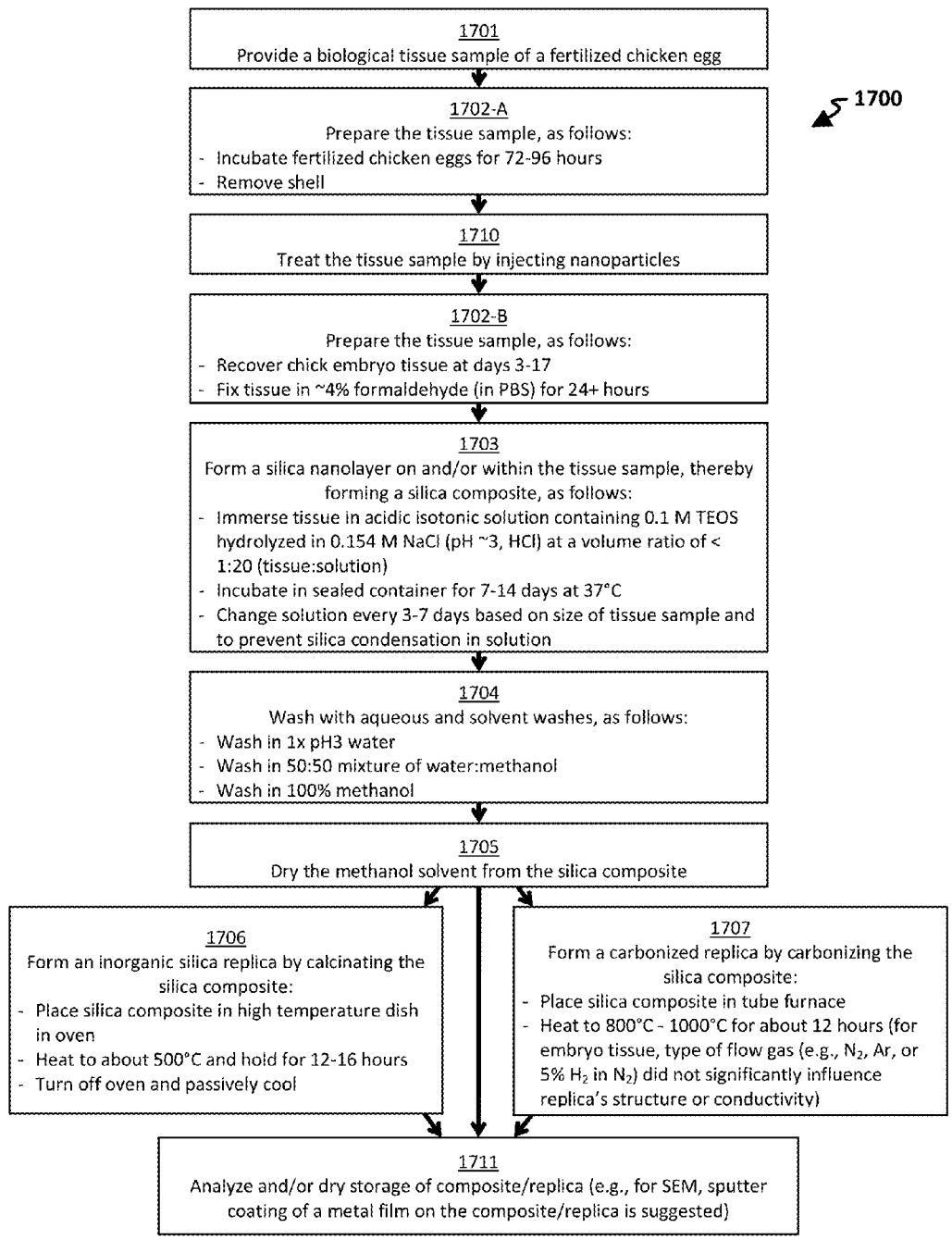
FIG. 17 is a flow chart of an exemplary method 1700 of the invention.

The methods of the invention can be adapted to include any useful step performed in any useful sequence. As shown in FIG. 5, one exemplary method 1500 includes a providing step 1501 and a sample preparation step 1502, in which the treatment step 1510 can be performed after the providing step 1501 or performed as a sub-step within the sample preparation step 1502. The method 1500 further includes a silification step 1503, a washing step 1504, and a drying step 1505. Various post-silification steps are optional, such as the calcination step 1506, the carbonization step 1507, the etch step 1508, and the analysis/storage step 1511. As shown in FIG. 17, another exemplary method 1700 includes a treatment step 1710 performed in between two preparation steps 1702-A,1702-B. Additional details for these steps are described herein.

Optional Post-Silification Steps

As described herein, the silica composite can be further processed in any useful manner. In one instance, the method 3000 optionally includes a calcination step 3006, a carbonization step 3007, an etch step 3008, a functionalization step 3009, and/or a conversion step 3010.

The calcination step 3006 includes forming an inorganic silica by calcinating the silica composite. Any useful conditions can be employed to calcine the composite by decomposing the organic matter present in the underlying biological sample. Exemplary conditions include a high temperature (e.g., of from about 400° C. to about 600° C., including from 500° C. to 600° C.) and/or an oxidative atmosphere (e.g., in air).

Figure 16D:
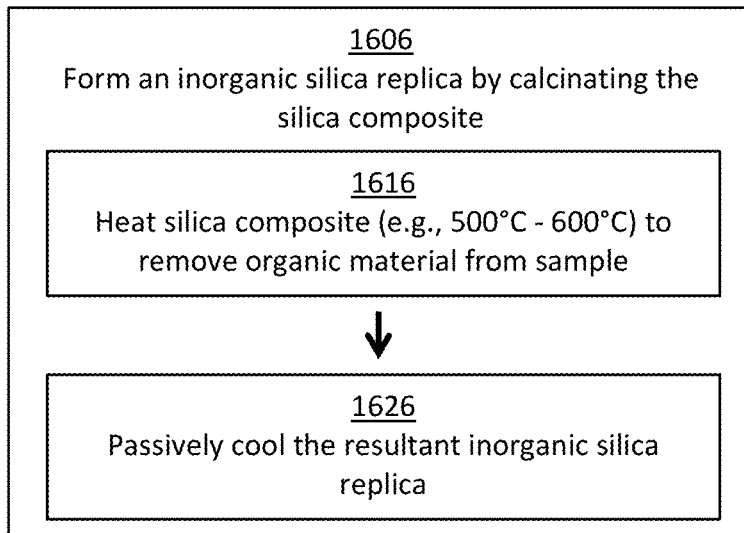

FIG. 16D shows an exemplary calcination step 1606 including a step 1616 of heating the silica composite to remove organic material, such as by heating at a temperature of from about 500° C. to 600° C.; and a step 1626 of cooling (e.g., passively cooling) the resultant inorganic silica replica.

The carbonization step 3007 includes forming a carbonized replica by carbonizing the silica composite. Any useful conditions can be employed to carbonize the composite by converting the organic matter present in the underlying biological sample into conductive carbon. Exemplary conditions include a high temperature (e.g., of from about 700° C. to about 1,100° C., including from 800° C. to 1,000° C. or about 900° C.) and/or a reductive or inert atmosphere.

Figure 16E:
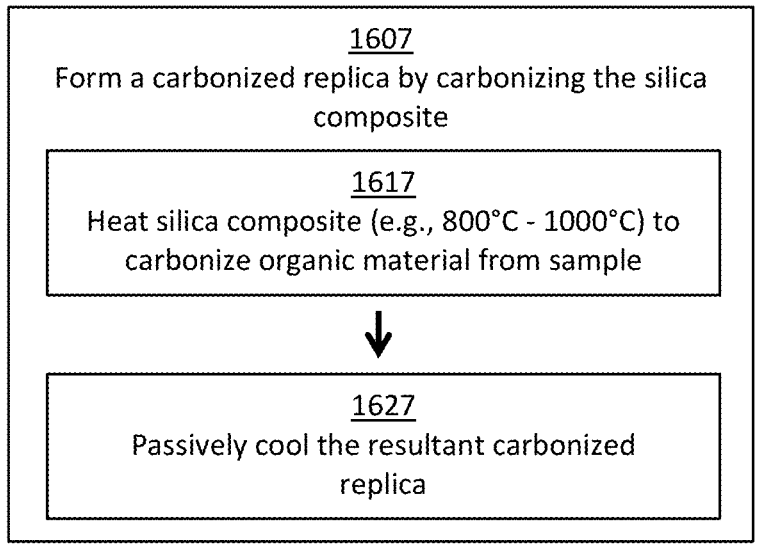

FIG. 16E shows an exemplary carbonization step 1607 including a step 1617 of heating the silica composite to carbonize organic material, such as by heating at a temperature of from about 800° C. to 1,000° C.; and a step 1627 of cooling (e.g., passively cooling) the resultant carbonized replica. This carbonization step can be followed by an optional etching step 2008 (e.g., such as with a wet etchant, including buffered hydrofluoric acid, potassium hydroxide, tetramethylammonium hydroxide, etc.), which includes immersing the carbonized replica in an etchant in order to form a carbon replica by etching any remnant silica present within the replica.

The constructs of the invention can be further processed in any useful manner. For instance, the construct (e.g., any herein, including any composite or replica) can be treated with a halide gas/solid displacement reaction to transform the silica component into another metal oxide (e.g., employing titanium halide as a vapor to convert silica into titania, magnesium to convert silica to magnesium oxide, molten aluminum to promote reactive metal penetration and convert silica to aluminum oxide, as well as other reactions described in Sandhage K H, "Materials 'alchemy': Shape-preserving chemical transformation of micro-to-macroscopic 3-D structures," *JOM* (*Journal of The Minerals, Metals & Materials Society* (*TMS*)) 2010 June; 62(6):32-43, which is incorporated herein by reference in its entirety). Thus, any of the methods herein can include an optional conversion step 3010, in which the base material of the composite is converted into another material by employing any useful reaction (e.g., any described herein).

In another instance, the construct can be further coated with one or more additional layers or particles, such as those formed from polymers, metals, conductive materials, semi-conductor materials, etc., by any useful process (e.g., dip coating, spinning, low-pressure chemical vapor deposition, sputter coating, etc.). Thus, the methods herein can include an optional functionalization step 3009, in which an inner or outer surface of a composite or replica is functionalized in any useful manner.

Analysis and Storage

As described herein, the constructs of the invention can be employed in any useful manner. In one instance, the method 3000 optionally includes an analysis step 3021. In another instance, the construct is stored for later use.

The constructs herein can be analyzed and/or stored in any useful manner. As described herein, the constructs provide a shape-preserved structure that is stable. Thus, the constructs themselves are useful biomimetic materials that can be stored and employed for any useful purpose (e.g., as a template for other biomaterials, a filter medium, a catalyst, etc.). In addition, the constructs can provide a sturdy composite or replica that can be analyzed by methodologies requiring harsh conditions that would otherwise be unsuitable for native, biological cells and tissues. Exemplary methodologies include high energy techniques, mechanical dissection techniques, and combinations thereof, such as scanning electron microscopy (SEM), transmission electron microscopy (TEM), energy-dispersive X-ray spectroscopy (EDS), back-scattered electron imaging (BSE), focused ion beam processes (FIB), and combinations thereof.

Silicic Acid Solutions

The methods and constructs herein employ a silicic acid solution, which provides one or more silicic acid compounds that form the silica nanolayer. In addition, the composition of the solution determines the kinetics of the silification process and, therefore, the structure of the silica nanolayer. Additional details follow.

The silicic acid solutions of the invention can include any useful silicic acid. Exemplary silicic acids include tetraalkoxysilanes (e.g., $Si(OR)_4$, wherein each R is, independently, an optionally substituted alkyl, alkoxy, or alkoxyalkyl, as defined herein), such as tetramethoxysilane ($Si(OCH_3)_4$ or TMOS), tetraethoxysilane ($Si(OC_2H_5)_4$ or TEOS), tetra-n-propoxysilane ($Si(n-OC_3H_7)_4$), tetra-n-butoxysilane ($Si(n-OC_4H_9)_4$), and tetrakis(2-methoxyethoxy) silane ($Si(OCH_2CH_2OCH_3)_4$); oxo-acids, such as orthosilicic acid ($Si(OH)_4$), metasilicic acid ($Si(O)(OH)_2$), disilicic acid ($H_2Si_2O_5$), and pyrosilicic acid ($H_6Si_2O_7$); or organoalkoxysilanes (e.g., $R'Si(OR)_3$, wherein each of R' and R is, independently, an optionally substituted alkyl, aryl, alkaryl, alkenyl, and alkynyl as defined herein), such as methyltrimethoxysilane ($CH_3Si(OCH_3)_3$), methyltriethoxysilane ($CH_3Si(OC_2H_5)_3$), methyl tri-n-propoxysilane ($CH_3Si(n-OC_3H_7)_3$), phenyltriethoxysilane ($PhSi(OC_2H_5)_3$), and vinyltriethoxysilane ($CH_2=C(H)Si(OC_2H_5)_3$), as well as oligomeric (e.g., dimeric, trimeric, tetrameric, octomeric, etc.) forms thereof.

To inhibit gel formation (i.e., gelation of the silicic acid compounds), the silicic acid solution is sufficiently dilute and sufficiently acidic. The kinetics of gelation depends, in part, on the concentration of the silicic acid compound (and its hydrolyzed forms) and the pH of the solution. At low pH (e.g., less than pH of about 7), gelation is suppressed and occurs on long time scales. In addition, within this low pH regime (e.g., pH of about 3), the charge of orthosilicic acid $Si(OH)_4$ is neutral and, thus, interacts with other molecules by way of hydrogen bonding and other non-covalent interactions. At high pH (e.g., greater than or equal to a pH of 7), the kinetics of polymerization is predominated by maximal silica solubility and dissolution, and the silica components are ionized (i.e., charged).

In some embodiments of the present invention, the reaction conditions are selected to favor silicic acid penetration into cells and tissue structures and/or to favor silica nanolayer formation (rather than gel formation). In some embodiments, the reaction conditions are selected to promote a self-limited reaction (e.g., limited homopolymerization and/or limited gel formation). In other embodiments, the concentration of the silicic acid compound in the solution is of from about 10 mM to 800 mM of silicic acid (e.g., any silicic acid compound herein, such as from 10 mM to 500 mM, 10 mM to 300 mM, 10 mM to 200 mM, 10 mM to 100 mM, 10 mM to 50 mM, 25 mM to 800 mM, 25 mM to 500 mM, 25 mM to 300 mM, 25 mM to 200 mM, 25 mM to 100 mM, 25 mM to 50 mM, 50 mM to 800 mM, 50 mM to 500 mM, 50 mM to 300 mM, 50 mM to 200 mM, 50 mM to 100 mM, 75 mM to 800 mM, 75 mM to 500 mM, 75 mM to 300 mM, 75 mM to 200 mM, 75 mM to 100 mM, 100 mM to 800 mM, 100 mM to 500 mM, 100 mM to 300 mM, and 100 mM to 200 mM). In yet other embodiments, the pH of the silicic acid solution is of from about 0.5 to about 7 (e.g., from 0.5 to 6, 0.5 to 5, 0.5 to 4, 0.5 to 3, 0.5 to 2, 0.5 to 1, 1 to 7, 1 to 6, 1 to 5, 1 to 4, 1 to 3, 1 to 2, 2 to 7, 2 to 6, 2 to 5, 2 to 4, 2 to 3, 3 to 7, 3 to 6, 3 to 5, and 3 to 4).

The solution can be formed with any useful solvent, such as an aqueous solvent including water (e.g., deionized water), a buffer (e.g., a phosphate buffer, a citric acid-$Na_2HPO_4$ buffer, a citric acid-sodium citrate buffer, a sodium acetate-acetic acid buffer, etc.), or a saline (e.g., phosphate buffered saline, Ringer's saline, Tris-buffered saline, borate-buffered saline, Hank's balanced salt solution, standard saline citrate, etc.) at any useful pH, such as any described herein. The pH of the solvent can be obtained by employing any useful acid or base. In certain embodiments, the aqueous solution includes an acid, such as one or more of hydrogen chloride, acetic acid, nitric acid, trifluoroacetic acid, etc.

In some instances, the solution is an isotonic solution (e.g., about 300 mOsm/L). Isotonicity can be maintained with any useful ion (e.g., sodium, potassium, calcium, chloride, lactate, etc.) or salt, such as sodium chloride, calcium chloride, potassium chloride, sodium lactate (e.g., 0.90% w/v of NaCl). In yet other instances, the solution is an acidic isotonic solution including any useful ion, solvent, and/or acid (e.g., any described herein).

Biological Samples, Including Tissue and/or Cells

Constructs can be formed from any useful biological sample, such as a cell sample, a tissue sample, or a population of cells. Exemplary samples include an organism (e.g., a non-viral organism, a mammalian organism, a vertebrate organism, a unicellular organism, a multicellular organism, a prokaryote, or a eukaryote), an embryo (e.g., a non-human embryo), an organ (e.g., brain, cochlea, eye, heart, intestines, kidney, liver, lung, ovary, pancreas, skin, spleen, stomach, and testis), a graft (e.g., an autograft, an allograft, an isograft, or a xenograft), a tissue culture, a tissue biopsy, a tissue section from any useful source (e.g., a mammalian source, such as a non-human mammalian source, a plant source, a fungal source, a microorganism source, a bacterial source, a viral source, etc.), chondral tissue, cartilage, tendon(s), ligament(s), vertebral disc(s), soft tissue (e.g., tendon, ligament, blood vessel, skin, articular cartilage, etc.), osteochondral tissue, islet tissue, osteogenic tissue, neural tissue, skin, bone tissue, bone marrow, adipose tissue, fibroblast(s), muscle tissue, blood, blood cells (e.g., a red blood cell, a white blood cell (e.g., a neutrophil, an eosinophil, a basophil, a lymphocyte, or a monocyte), a hematopoietic stem cell, a platelet, a peripheral blood stem cell, etc.), corneal tissue, ocular lens, meniscus, hair, striated muscle, smooth muscle, cardiac muscle, connective tissue, and stem cells. The sample can be obtained from any useful subject or source (e.g., a human subject, a non-human subject, a mammalian subject, an animal subject, etc.).

In yet other embodiments, the constructs further includes any cellular component. Exemplary cellular components include a virus, a protein, a nucleic acid (e.g., DNA, RNA, as well as hybrids and duplexed forms thereof), a lipid particle, a biomolecule, a lipid, a lipid vesicle, a polysaccharide, an organelle, and a cytoskeletal filament.

In particular embodiments, the methods and constructs herein employ one or more cells, as defined herein. Surprisingly, the methods herein can accurately preserve the shape of cells obtained from soft tissue sources. In one instance, the soft tissue source has an ultimate strength (i.e., the breaking strength of a material under different modes of loading, such as tensile, compressive, torsional, or bending modes) less than that of bone (e.g., where the soft tissue source has an ultimate tensile strength less than about 135 MPa and/or an ultimate compressive strength less than about 200 MPa). In other instance, the soft tissue source has an ultimate tensile strength of from about 0.1 MPa to about 110 MPa. Exemplary ultimate tensile strength values include those for urinary bladder (about 0.1 to 0.4 MPa), artery (about 0.1 to 0.9 MPa), aorta (about 0.3 to 2.5 MPa), skin (about 1 to 20 MPa), liver (about 1.8 to 3 MPa), spinal or cranial dura (about 2 to 5 MPa), cartilage (about 3 to 40 MPa), ligament (about 50 to 100 MPa), and tendon (about 50 to 100 MPa). Methods for evaluating ultimate strength, as well as other exemplary values, are provided in Brunon A et al., "Mechanical characterization of liver capsule through uniaxial quasi-static tensile tests until failure," *J. Biomech.* 2010; 43:2221-7; Holzapfel G A et al., "Biomechanics of soft tissue," *Biomech Preprint Series*, paper no. 7, Graz University of Technology, Austria, November 2000 (15 pp.); and Pal S, "Mechanical properties of biological materials," in *Design of Artificial Human Joints & Organs*, Springer Science+Business Media, New York, N.Y., 2014, pp. 23-40, each of which is incorporated herein by reference in its entirety.

Fixative Reagents

The biological sample can be treated with one or more fixative reagents. The fixative reagent can include any useful agent or compound configured to form a bond (e.g., a covalent bond) between two reactive groups (e.g., a carboxyl group and an amino group or a phospho group and an amino group). Exemplary fixative reagents include a chemical fixative (e.g., formaldehyde, paraformaldehyde, glutaraldehyde, formalin, acetone, isopropanol, ethanol, and/or methanol) or a cross-linker, as well as combinations thereof. Exemplary cross-linkers include those for forming a covalent bond between a carboxyl group (e.g., —$CO_2H$) and an amino group (e.g., —$NH_2$) or between a phospho group (e.g., —$P(O)(OH)_2$) and an amino group (e.g., —$NH_2$), such as 1-ethyl-3-(3-dimethylaminopropyl)carbodiimide (EDC) and dicyclohexylcarbodiimide (DCC), optionally used with N-hydroxysuccinimide (NHS) and/or N-hydroxysulfosuccinimide (sulfo-NHS). Other cross-linkers include those for forming a covalent bond between an amino group (e.g., —$NH_2$) and a thymine moiety, such as succinimidyl-[4-(psoralen-8-yloxy)]-butyrate (SPB); a hydroxyl group (e.g., —OH) and a sulfhydryl group (e.g., for a cysteine moiety), such as p-maleimidophenyl isocyanate (PMPI); between an amino group (e.g., —$NH_2$) and a sulfhydryl group (e.g., for a cysteine moiety), such as succinimidyl 4-(p-maleimidophenyl)butyrate (SMPB) and/or succinimidyl 4-(N-maleimidomethyl)cyclohexane-1-carboxylate (SMCC); and between a sulfhydryl group (e.g., for a cysteine moiety) and a carbonyl group (e.g., an aldehyde group, such as for an oxidized glycoprotein carbohydrate), such as N-beta-maleimidopropionic acid hydrazide-trifluoroacetic acid salt (BMPH) and/or 3-(2-pyridyldithio)propionyl hydrazide (PDPH). Treatment with a fixative reagent can be followed by a rinse step (e.g., with any useful solvent, such as any aqueous solvent described herein).

Permeabilization Reagents

The biological sample can be treated with one or more permeabilization reagents. The permeabilization reagents can include any useful agent or compound configured to permeabilize cell membranes, or portions thereof. Exemplary permeabilization reagents include a surfactant, such as Triton™ X-100 (e.g., polyethylene glycol p-(1,1,3,3-tetramethylbutyl)-phenyl ether), sodium dodecyl sulfate (SDS), Tergitol-type NP-40 (nonyl phenoxypolyethoxylethanol), and polysorbate 20 (Tween 20); an alcohol, such as methanol; a solvent (e.g., acetone or acetic acid); a glycoside, such as saponin or digitonin; a protease, such as proteinase K; or an exotoxin, such as streptolysin 0.

Chemical or Biological Agents

The biological sample can be treated with one or more agents. Exemplary agents (e.g., chemical or biological reagents) include a therapeutic agent, e.g., a drug, a prodrug, a vitamin, an antibody, a protein, a hormone, a growth factor, a cytokine, a steroid, an inhibitor (e.g., a kinase inhibitor), an anti-cancer agent, a fungicide, an anti-microbial, an antibiotic, etc.; a morphogen; an enzyme; a nucleic acid or a polynucleotide, including double stranded, single stranded, multiplexed, RNA, DNA, siRNA, chimeric, etc., forms thereof; a toxin, e.g., a bacterial protein toxin; a peptide, e.g., an antimicrobial peptide, a fibronectin motif (e.g., represented by the amino acid sequence RGD), or a collagen motif (e.g., represented by the amino acid sequence DGEA, SEQ ID NO:1); an antigen; an antibody; a detection agent (e.g., a particle, such as a conductive particle, a microparticle, a nanoparticle, a quantum dot, a latex bead, a colloidal particle, a magnetic particle, a fluorescent particle, etc.; or a dye, such as a fluorescent dye, a luminescent dye, a chemiluminescent dye, a colorimetric dye, a radioactive agent, an electroactive detection agent, etc.); a label (e.g., a quantum dot, a nanoparticle, a microparticle, a barcode, a fluorescent label, a colorimetric label, a radio label (e.g., an RF label or barcode), avidin, biotin, a tag, a dye, a marker, an electroactive label, an electrocatalytic label, and/or an enzyme that can optionally include one or more linking agents and/or one or more dyes); a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), and/or an enzyme (e.g., that reacts with one or more markers, such as any described herein)); as well as combinations thereof.

In some embodiments, the biological sample is treated with an agent to alter its geometry or morphology. For instance, the sample can be treated with an agent that forms pores within a lipid layer, e.g., an antibiotic, a bacterial protein toxin, a cell permeabilizing agent, or an antimicrobial peptide that forms pores within lipid layers of cells, such as a bacterial cell. In another instance, the sample is treated with an agent that promotes cross-linking of various receptors present on a cell, such as an antigen that binds to receptors in an immunological cell (e.g., a mast cell). In yet another instance, the sample is treated with an agent that promotes cytoskeletal rearrangement within a cell, such as by employing a GTP-ase inhibitor and/or growth factors that promote actin rearrangement.

In another instance, the sample is treated with an amphipath, which is a chemical compound displaying both hydrophobic and hydrophilic chemical functional groups. In addition, such amphipaths can be positively charged (cationic), negatively charged (anionic), or neutral at a particular pH (e.g., a pH of 7). Without wishing to be limited by mechanism, such amphipaths localize preferentially into different regions of a lipid layer, in which more cationic amphipaths insert into more negatively charged regions of the lipid layer and more anionic amphipaths insert into more positively charged regions of the lipid layer. This molecular interaction results in a geometric change on a cellular level, such that the amphipath-treated lipid layers will preferentially form cup-shaped cells, crenated cells, spherical cells, etc. based on the cationic or anionic nature of the amphipath agent. Thus, amphipaths can be employed to provide shape-encoded cells, composites, and replicas.

Exemplary amphipaths include cationic amphipaths (e.g., a phenothiazine (e.g., chlorpromazine, methochlorpromazine, promazine, promethazine, thioridazine, trifluoperazine, triflupromazine, and salts thereof), an antihistamine (e.g., pheniramine, brompheniramine, or bamipine), a local anesthetic (e.g., procaine, lidocaine, dibucaine, stadacaine, tetracaine, and salts thereof), N,N-dimethylaminoethyl benzoate, N,N-diethylaminoethyl benzoate, N,N-diethyl-3-(4-nitrophenyl)propan-1-amine (HK-27), N,N,N-triethyl-4-nitrobenzenepropanaminium (HK-25), lidocaine N-methyl hydrochloride (QX-222), chloroquine, reserpine, prenylamine, verapamil, or salts thereof); anionic amphipaths (e.g., free fatty acids, barbiturates, benzoates (e.g., gentisate or salicylate), bile acids, alkyl sulfonates, alkylpyridinium chlorides, ethacrynic acid, 2,3-dinitrophenol, trinitrophenol, dipyridamole, or salts thereof); neutral amphipaths (e.g., lysolechitin, saponine, etc.); detergents; surfactants (e.g., Triton-X 100 or octylammonium chloride); lipids (e.g., a phospholipid such as phosphatidylcholine or a lysophospholipid such as lysophosphatidylcholine); fatty acids (e.g., a polyunsaturated fatty acid such as arachidonic acid); as well as surface active agents and surface active drugs (e.g., those described in Schreier S et al., "Surface active drugs: self-association and interaction with membranes and surfactants. Physicochemical and biological aspects," *Biochim. Biophys. Acta* 2000 November; 1508(1-2):210-34 and Wong P, "A basis of echinocytosis and stomatocytosis in the disc-sphere transformations of the erythrocyte," *J. Theon. Biol.* 1999 Feb. 7; 196(3):343-61, each of which is incorporated herein by reference in its entirety).

Other alterations to the intracellular or extracellular environment can induce a change in shape or geometry. For instance, such alterations can include a change in salt concentration, change in pH, change in cholesterol concentration within the membrane, and change in ATP concentration. Cup-shaped red blood cells can be induced by employing low salt, low pH, and/or cholesterol depletion conditions. In contrast, crenate red blood cells can be induced by employing high salt, high pH, cholesterol enrichment, and/or ATP depletion conditions. Such conditions and environments can be provided to the sample with any useful agent. Exemplary agents include an acid, a base, or a buffer (e.g., to change pH conditions); exogenous salts or ions, such as monovalent or divalent salts including cobalt, nickel, calcium, magnesium, or manganese ions with an optional ionophore (e.g., to change intracellular or extracellular salt conditions); exogenous cholesterol (e.g., to increase cholesterol concentration within the lipid membrane); and/or a cholesterol binding agent (e.g., to bind and remove cholesterol from membranes, such as by employing a cyclodextrin derivative, e.g., methyl-β-cyclodextrin).

Chemical and biological agents can also be employed with a composite or a replica (i.e., after the biological sample has been silicified and then either calcined, carbonized, etched, transformed, converted, functionalized, etc.). Such agents can be used to introduce new functional groups to the composite or replica. Functional groups can impart any useful property, such as binding specificity, hydrophobicity, hydrophilicity, biocompatibility, non-immunogenicity, detectability, etc.

In one instance, the composite or replica can be functionalized with one or more silanizing agents to modify surface characteristics. For instance, if the silanizing agent has a hydrophobic moiety, then the composite or replica can be rendered hydrophobic upon functionalizing with that agent. Exemplary silanizing agents include silazane (e.g., hexamethyldisilazane (HMDS)), haloalkylsilane (e.g., methyltrichlorosilane, trichlorocyclohexylsilane, dichlorodimethylsilane, dichloroethylsilane, bromotrimethylsilane, or chlorotrimethylsilane), haloarylsilane (e.g., fluorotriphenylsilane), trialkylsilylsilane (e.g., chlorotris(trimethylsilyl)silane), and silanol (e.g., 2-(trimethylsilyl)ethanol). Other silanizing agents include an agent having the structure of $(R^L)_3SiR^M$ or $R^LSi(R^M)_3$ or $R^LSi(SiR^M)_3$ or $(R^L)_2R^MSi$-L-$SiR^M(R^L)_2$, where each of $R^L$ is, independently, H, optionally substituted alkyl, hydroxyl, hydroxyalkyl, halo, haloalkyl, alkoxy, or aryl; each of $R^M$ is, independently, a functional moiety, such as optionally substituted alkyl, haloalkyl, hydroxyalkyl, alkenyl, alkoxy, aryl, alkaryl, heterocyclyl, heteroaryl, cycloalkyl, alkcycloalkyl, amino, aminoalkyl, or amido, as defined herein; L is a linker, such as optionally substituted alkylene, alkyleneoxy, arylene, heteroalkylene, heteroalkyleneoxy, or —N($R^{N1}$)—, where $R^{N1}$ is H, optionally substituted alkyl, alkaryl, or aryl; and where one of $R^L$ and X can optionally combine to form an optionally substituted heterocyclyl.

In one instance, the composite or replica can be functionalized with one or more particles. Such particles may be useful for detection, drug delivery, etc. Exemplary particles include any described herein, including a nanoparticle (e.g., a nanotube), a microparticle, a quantum dot, a lipid particle, or a liposome, where each of these particles can optionally further include a label, a tag, a peptide, an antibody, a coating, a linker, and/or a drug, such as any described herein.

In another instance, the composite or replica can be functionalized with one or more coatings. Such coatings may be useful for biocompatibility and/or biodistribution profiles. Exemplary coatings include a hydrogel, a polyether (e.g., a polyethylene glycol or a polypropylene glycol), a polymer (e.g., an epoxy, a polyaniline), a dendrimer, a metal (e.g., a noble metal, such as gold, platinum, silver, etc.), an oxide coating (e.g., a zirconium oxide, a tin oxide, a zinc oxide, or a titanium oxide coating, including other dopants such as silicon, barium, manganese, iron, etc., such those coatings obtained by atomic layer deposition, hydrothermal conversion, sol-gel conversion, thermal annealing, and/or thermal evaporation), a ceramic (e.g., boron nitride), etc. In yet another instance, the composite or replica can be functionalized within a matrix, such as a polymeric matrix, a protein matrix, etc.

Composites and replicas can be readily converted to other types of materials. For instance, the silicon and oxygen atoms within the underlying silica structure can be displaced and/or replaced with other types of atoms (e.g., metallic atoms). In addition, the underlying organic matter provided by the biological sample can be removed or transformed (e.g., into conductive carbon). Such silica displacement reactions can be performed to obtain vast types of replicas, such as those including titanium oxide (e.g., titania (e.g., $TiO_2$) and titanate (e.g., $TiO_3$), including doped or complex forms thereof, such as $M_2TiO_4$ or $MTiO_3$, where M is a metal, such as a divalent metal (e.g., Ba, Sr, or Mg), magnesium oxide (e.g., MgO, as well as doped and complex forms thereof, such as $MgO/MTiO_3$). These displacement reactions are generally conducted in the presence of a reactant (a halide gas or an elemental gas), which results in oxidation/reduction or metathesis reactions to effectively displace or replace a silica or oxygen atom (of the composite or replica) with an atom from the reactant. After the displacement reaction, further reactions can be conducted to etch certain elements, coat the composite/replica, etc. to obtain further functionality.

EXAMPLES

Example 1: Silica Replicas by Synthetic Fossilization of Soft Biological Tissues Numerous methodologies are currently employed to preserve physical structures in biological specimens. Electron microscopy (EM) allows for increasingly better resolution and imaging in both scanning electron (SEM) and transmission electron microscopy (TEM) modes. Yet, despite consistent advancements in instrumentation, techniques for the preparation of biological materials for EM remain largely unchanged since first put into practice in the early $20^{th}$ century. Other methods, such as cryofixation (vitrification), currently come closest to capturing the most 'accurate' native state of a biomolecular structure but requires specialized equipment, subsequent processing (for example, replication, fracture and/or cryo-focused ion beam (cryo-FIB)), and considerable expertise. Freeze fracture is a complex, highly specialized technique. Chemical fixation can degrade sample architectures, and other secondary and tertiary fixation can employ toxic chemicals. Specimens can also be embedded in resins to enable thin sectioning, but this process destroys the 3D structure as a whole. Finally, for observation using SEM, biological specimens generally require coating with metal or carbon films, but resolution can be limited by the grain size and uniformity of the coating, which can render only exposed surfaces conductive.

To overcome limitations of existing methods of tissue/organism stabilization and imaging, we developed a sample preparation procedure requiring few steps and minimal expertise or specialized equipment. This procedure resulted in conformal, structural stabilization from subcellular to organism scales that avoided embedding in polymer and that rendered an intrinsically conductive specimen that was resistant to high intensity energy and long-term degradation. We postulated that this process would provide new opportunities for biological analysis (for example, internal imaging with elemental contrast) and establish a new preparation method that complements the substantial recent developments in EM instrumentation.

As a starting point, we considered natural mineralization processes that produce fossilized materials. Structural preservation of biological materials through fossilization requires an intricate alignment of optimum conditions that are achieved over long time scales by complex geological processes. Even if these are satisfied, preservation of soft tissue in natural fossils is extremely rare.

'Synthetic fossilization' has been widely explored using stiff templates. For example, wood, leaves, butterfly wings, pollen grains, viruses, and diatoms as templates for material deposition and subsequent conversion (see, e.g., Miyako E et al., "Self-assembled carbon nanotube honeycomb networks using a butterfly wing template as a multifunctional nanobiohybrid," *ACS Nano* 2013; 7:8736-42; Goodwin W B et al., "Conversion of pollen particles into three-dimensional ceramic replicas tailored for multimodal adhesion," *Chem. Mater.* 2013; 25(22):4529-36; Zimmerman A B et al., "Titania and silica materials derived from chemically dehydrated porous botanical templates," *Chem. Mater.* 2012; 24(22): 4301-10; Van Opdenbosch D et al., "Silica replication of the hierarchical structure of wood with nanometer precision," *J. Mater. Res.* 2011 May; 26(10):1193-202; Paris O et al. "Biomimetics and biotemplating of natural materials," *MRS Bull.* 2010 March; 35(3):219-25; Shenton W et al., "Inorganic-organic nanotube composites from templated mineralization of tobacco mosaic virus," *Adv. Mater.* 1999; 11(3): 253-6; Rong J et al., "Tobacco mosaic virus templated synthesis of one dimensional inorganic-polymer hybrid fibres," *J. Mater. Chem.* 2009; 19:2841-5; and Losic D et al., "Diatomaceous lessons in nanotechnology and advanced materials," *Adv. Mater.* 2009; 21(29):2947-58).

However, these templates are already mechanically stable, comprising stiff polysaccharides (wood, butterfly wings) or bioinorganic composites (diatoms). Thus, in contrast to soft tissues, they are intrinsically resistant to structural deformation upon drying and subsequent chemical processing. The extension of 'synthetic fossilization' to soft biomaterials under shape-preserving conditions would provide a new foundational approach for specimen preservation, create opportunities for conversion into more durable and EM-compatible materials, and serve as a facile approach to create new classes of biomimetic composite materials.

Thus, structural preservation of complex biological systems from the subcellular to whole organism level in robust forms, enabling dissection and imaging while preserving 3D context, represents an enduring grand challenge in biology. Here, we show a simple immersion method for structurally preserving intact organisms via conformal stabilization within silica. Soft, biological tissues are replicated from the subcellular to the organismal scale in silica, a process we term silica bioreplication (SBR).

This self-limiting SBR process occurs by condensation of water-soluble silicic acid proximally to biomolecular interfaces throughout the organism. We show shape- and feature-preserving SBR of intact multicellular specimens (tissues derived from chicken embryos), inclusive of cells, extracellular matrices, tissues, and organs. Conformal nanoscopic silicification of all biomolecular features imparted structural rigidity enabling the preservation of shape and nano-to-macroscale dimensional features upon drying to form a biocomposite (i.e., a silica composite having an underlying biological sample), which can be treated with high temperature oxidative calcination (e.g., 500° C. to 600° C.) to form silica replicas or with reductive pyrolysis (e.g., 800° C. to 1,000° C.) to form electrically conductive carbon replicas of complete organisms (see, e.g., Examples 2 and 3 herein). The simplicity and generalizability of this approach should facilitate efforts in biological preservation and analysis and could enable the development of new classes of biomimetic composite materials.

Methods

Chicken embryo incubation and preparation: Ex ovo chicken embryo experiments were conducted with all embryos used between day 3 and 17 (and as indicated in each experiment). All embryos were handled and euthanized following approved procedures. Fertilized chicken eggs were obtained from the East Mountain Hatchery (Edgewood, N. Mex.) and placed in an automated incubator (GQF 1500 professional, Savannah, Ga.) for 72-96 hours, humidified (70% relative humidity, RH), and heated (37° C.). Following incubation, egg shells were sterilized by brief immersion in ethanol and physically cleaned with a paper towel. The egg shells were then scored using a rotary tool and cracked into a medium sterilized weigh boat (VWR Int'l LLC, Radnor, Pa.). Weigh boats were covered with a square plastic petri dish (VWR) and returned to the incubator until they were killed or until time of injection. For particle injections, 0.1 ml of AuNPs (0.25 OD at $\lambda$=600 nm) was injected via a pulled glass capillary needle into the vein of the chorioallantoic membrane and allowed to circulate for 90 minutes. Upon removal of embryos from the ex ovo egg, tissue was immersed in 3.7% paraformaldehyde in PBS for at least 24 hours before silicification. For embryos at day 17 of development, individual organs were dissected from the chicken and fixed individually.

Silicification of specimens: Following fixation, tissues or whole embryos were silicified by brief rinsing with PBS followed by subsequent immersion in silicification solution in a sealed container at 37° C. for 7-21 days. The silicification solution contained 0.1 M silicic acid derived from hydrolysis of tetramethyl orthosilicate (TMOS) at pH 3 containing 0.154 M NaCl (0.9% saline solution). For example, to make a 100 ml solution, 0.1 ml of 1 N HCl was added to ~98.5 ml of the saline solution. Then, 1.5 ml of TMOS was added to this solution and stirred vigorously (this can be accomplished by shaking in a sealed container) to hydrolyze the TMOS (it will appear dissolved upon hydrolysis) forming principally monosilicic acid $Si(OH)_4$. The approximate volume ratio of specimen to solution was kept at or below 1:20 as ratios exceeding 1:10 (specimen: silica solution; v/v) often were observed to induce gelation of the solution (likely due to an increase in solution pH).

No obvious difference in gross phenotype was apparent over the course of three weeks, and gelation of solution (due to silica self-condensation) occurred only if the solution was not refreshed for over 3 weeks. Silica deposition upon specimens was apparent after a few days of immersion in the silicic acid solution by a change in color of the specimen from pink/brown to white. Following silicification, SBR tissues were rinsed in $H_2O$ (pH 3) and 1:1 water/methanol, and finally dried in air from 100% methanol. Details of this method are provided in FIG. 17. In brief, the method 1700 includes a providing step 1701, a sample preparation step 1702-A, a treatment step 1710 with nanoparticles, a sample preparation step 1702-B including fixation, a silification step 1703, a washing step 1704, a drying step 1705, a calcination step 1706, a carbonization step 1707, and an analysis/storage step 1711.

Dehydration of non-silicified tissue: The non-silicified heart tissue shown in FIG. 4*d* was fixed overnight in 3.7 vol. % formaldehyde in PBS solution; dehydrated by using sequential washes, each having a duration of 20 minutes (33% ethanol (EtOH) in $H_2O$; 50% EtOH; 66% EtOH; 2×100% EtOH; 50% EtOH in HMDS; 100% HMDS); and allowed to dry in air for 16 hours.

Calcination of samples: Silicified samples were calcined by placing them in a covered (but not air tight) Pyrex® dish and treating for 12-16 hours in an oven (Fisher Scientific, Model #495A) at 500° C. under ambient atmospheric conditions. Ramp temperature was controlled at 1° C. per minute; however, cooling rate was uncontrolled.

Scanning electron microscopy/energy-dispersive spectroscopy: SEM images were recorded using an FEI Quanta series SEM. This instrument was equipped with an energy-dispersive X-ray spectroscopy from EDAX, which was used in single pixel mode for elemental identification. For SEM images shown in FIG. 5, samples were sputter-coated with Au/Pd. In addition, FIB milling shown in FIG. 10 was performed on this instrument.

Silica Bioreplication of Chicken Embryos

Recently, we observed that silicification of cultured mammalian cells derived from a range of tissues preserves cellular structure from the nano (DNA, organelles and so on) to whole cell (micrometer) level (see, e.g., Kaehr B et al., "Cellular complexity captured in durable silica biocomposites," *Proc. Natl. Acad. Sci. USA* 2012 October; 109(43): 17336-41, which is incorporated herein by reference in its entirety). This ability to preserve intact cells with nanoscale fidelity laid the groundwork to examine SBR of complex multicellular systems in which cells organize to form diverse tissue types with distinct 3D architectures. To explore these possibilities, we used chicken embryos (*Gallus gallus domesticus*), which have been commonly used as exemplary in vivo models in the study of developmental biology, nanomedicine, and other organism-scale processes (see, e.g., Le Douarin N M, "The avian embryo as a model to study the development of the neural crest: A long and still ongoing story," *Mech. Dev.* 2004 September; 121(9):1089-102; and Leong H S et al., "Intravital imaging of embryonic and tumor neovasculature using viral nanoparticles," *Nat. Protoc.* 2010 August; 5(8):1406-17).

As chicken embryos are primarily composed of soft tissue during the first 10 days of development and have well-formed internal organs by day 17, their use over 3-17 days of development allows us to demonstrate the efficacy of SBR for structural preservation of a wide spectrum of soft tissues and organs. First, embryos were removed from fertilized eggs at day 3 of development by cutting the egg shell and removing the intact embryo and membranes (see Leong H S et al., *Nat. Protoc.* 2010 August; 5(8):1406-17). Following sufficient development (0-14 days of incubation at 37° C. and >65% relative humidity), embryos were euthanized and dissected or fixed whole in 3.7% formaldehyde in phosphate-buffered saline (PBS) for a minimum of 24 hours. After fixation, embryos or individual organs were rinsed in PBS and then incubated for 7 days or more in acidic saline media (pH 3, 0.9% NaCl) containing silicic acid ($Si(OH)_4$, 0.1 M) in a sealed container at 37° C.

Under these isotonic conditions, $Si(OH)_4$ self-condensation into bulk silica ($SiO_2$), which would obscure all structural detail, is minimized (formation of bulk gels would occur only after approximately three weeks of aging); instead, as we have observed using individual proteins and matrices (Khripin C Y et al., "Protein-directed assembly of arbitrary three-dimensional nanoporous silica architectures.," *ACS Nano* 2011 January; 5(2):1401-9), as well as single cells (Kaehr B et al., *Proc. Natl. Acad. Sci. USA* 2012 October; 109(43):17336-41), condensation only occurred when catalyzed by proximal biomolecular components—first mediated via hydrogen-bonded interactions with silica precursors—and subsequently catalyzed amphoterically from the spectrum of acid and base moieties presented at the biomolecular surface. This enabled the self-limiting formation of a nanoscopic (4 nm to 10 nm thick) silica replica of all cellular-to-organism level features. Following incubation in the silicic acid solution, embryos were washed in $H_2O$ (pH 3), incubated in 1:1 $H_2O$/methanol (20 minutes) and 100% methanol (20 minutes), and air dried.

This procedure applied to an avian heart is shown schematically in FIG. 4*a*. FIG. 4*b* shows an optical image of the resultant composite specimen. In order to assess the extent and fidelity of silica deposition upon the template, the organic template was removed via calcination at 500° C. producing an inorganic silica replica (FIG. 4*b*, right). As seen in FIG. 4*d*, an avian heart was processed without silicic acid (i.e., did not undergo the SBR procedure), and dehydrating of the non-processed heart displayed marked reduction in size, as compared to an SBR-processed heart (FIG. 4*e*, which compares the size of an SBR-processed heart in FIG. 4*c* with a non-processed heart in FIG. 4*d*).

The SBR procedure applied to an intact chicken embryo is shown schematically in FIG. 5*a*. FIG. 5*b,c* shows optical images of the resultant biocomposite specimen of a 9-day-old embryo, where both hydrated (that is, after silicification but before solvent washing and air drying) and dehydrated (following solvent washing and air drying) forms are shown. To assess the extent and fidelity of silica deposition upon the template, the organic template was removed via calcination at 500° C., thereby producing an inorganic silica replica (FIG. 5*d*). Magnified SEM images of surface and subsurface tissues (FIG. 5*e-g* and corresponding magnifications FIG. 5*h-k*) detailed SBR over the entirety of the organism.

Figure 6:
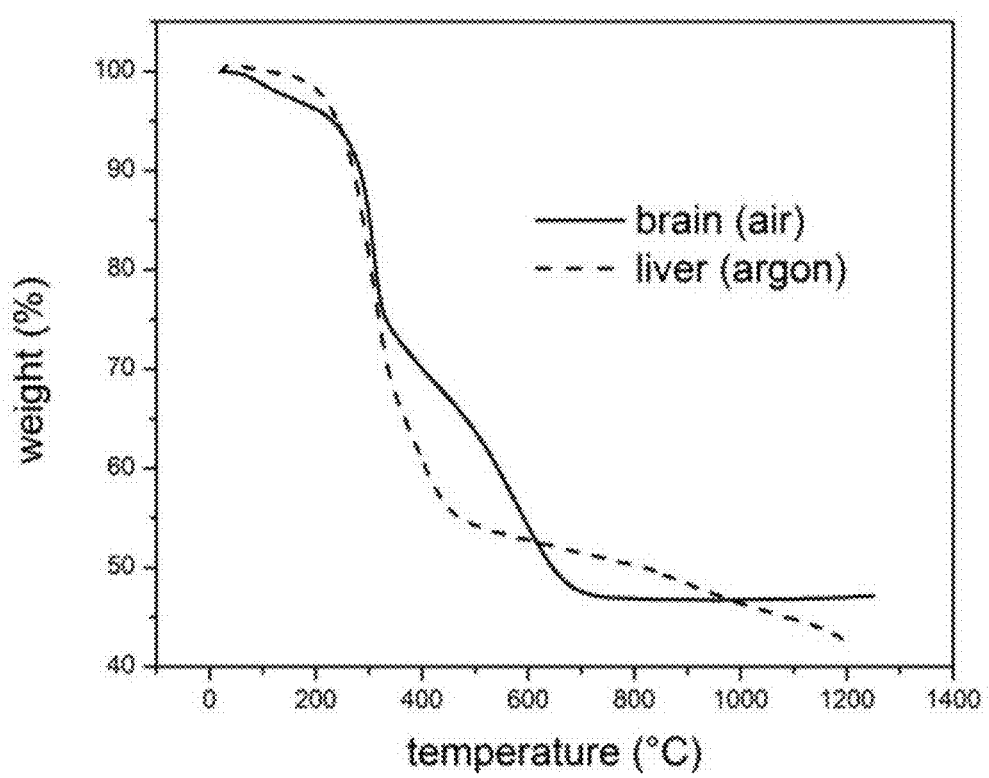
FIG. 6 is a graph showing a thermogravimetric analysis (TGA) curve of a silicified embryo tissue produced by the SBR process and recorded under flowing air or argon (50 ml min$^{-1}$).

Overall, the images in FIG. 5 revealed the high fidelity replication afforded by SBR; over 6 orders of magnification from the subcellular to organismal level and across diverse tissues types. As can be seen, the embryo showed minimal shrinkage (FIG. 5d). In addition, we observed no substantial change in the overall dimensions of this embryo following high temperature treatment (500° C.) for 12 hours, despite substantial weight loss (>50%) due to volatilization of the organic bulk biomolecular structure accompanied by continued condensation of silica, as indicated by thermogravimetric analysis (TGA) of SBR chicken embryo tissue under air (FIG. 6). Furthermore, heterogeneous, microscopic details were preserved, such as subsurface ocular tissue (FIG. 5j) and surface cells on tongue tissue (FIG. 5k), by employing the same SBR preservation technique.

Organism-Scale High Fidelity Silica Replicas

Following verification of exterior surface structural preservation post silicification and calcination, we next examined the extent of silicification of internal organs and tissues. FIG. 7a shows a calcined silica replica of a 4-day-old complete chicken embryo.

Indeed, in addition to the detailed surface features including vertebrae, developing brain, eyes and skin folds preserved in the silica embryo replica, FIG. 7a shows SEM images of the calcined silica replica of an embryo in which the interior of the embryo, inclusive of a lobe of the liver, has been exposed by fracture of the specimen along the midline. Closer examination at the fracture point (FIG. 7b) reveals preservation of complex structures from various tissue types, indicating silicification of tissues deep within the organism.

As apparent in FIG. 7a-c, successive magnification of the indicated fracture point shows diverse cell types and extracellular matrix, including red blood cells and hepatocytes on the surface of the developing liver. FIG. 7d shows a single white blood cell replica nestled among red blood cells located deep within a blood vessel of a calcined and fractured liver. SEM of the surface of large blood vessels on the silica heart replica showed intact chicken red blood cell structures attached to replicated elastin and collagenous fibers (~10-150 nm) and fiber bundles (~400-1,000 nm) (FIG. 7e-g).

The ready facile extension to a soft tissue—inclusive of all internal and external hierarchical structures—is remarkable given the fragility of unsupported tissues and organs in the absence of hydration. Organism-scale shape preservation combined with high fidelity nanoscale resolution of all extracellular and subcellular features within entire organs and throughout complete organisms indicated that SBR is macroscopically extensive, providing structural stability to soft tissue, yet nanoscopically thin. This is attributed to self-limiting silicic acid condensation at all biomolecular interfaces catalyzed amphoterically by proximal membrane-associated proteins, carbohydrates, as well as other components. Occlusion of the catalytic biomolecular surface by silica naturally limits silica deposition to <10 nm, and the resultant SBR composite appeared virtually indistinct from the biological specimen. Remarkably, the thin but extensive nanoscopic silica layer stabilized the organism-scale features on drying and calcination to 500° C. to 600° C. despite substantial weight loss due to combustion of the organic template and further silica condensation.

Example 2: Conductive, Carbonized Replicas by Shape-Preserving Transformation of Silica Replicas The stability of the SBR structure, as discussed above in Example 1, suggested opportunities for further material transformations. Thus, we wondered whether subjecting SBR tissues to pyrolysis under inert atmosphere would yield a dimensionally preserved, conductive replica via carbonization of the organic biological template. We reasoned that this transformation would produce a highly EM-compatible specimen (as all specimen surfaces should be intrinsically conductive), provided that the structure was preserved following high temperature treatment. Thus, following SBR, specimens can be subjected to high temperature pyrolysis (800° C. to 1,000° C.) under reducing conditions to convert the organic constituents into conductive carbon.

For pyrolysis, silicified and non-silicified samples were placed uncovered in a ceramic combustion boat (~20×75 mm W×L alumina or porcelain) and heated to either 800° C. or 1,000° C. in a quartz tube (25 mm OD; 20 mm ID) inserted in a tube furnace (Lindberg/Blue Model #TF55035A) under constant gas flow ($N_2$, Ar, or 5% $H_2$ in $N_2$); the heating rate was 5° C. per min and final temperature was held for 12 hours. We found that an 800° C. holding temperature was sufficient for carbonization of samples and higher temperatures were not required.

This carbonization (or pyrolysis) procedure resulted in remarkable preservation of structure and enabled whole, intact specimens. These specimens, in turn, could be imaged and sectioned ad infinitum and arbitrarily across the macro- to nano-scale without loss of resolution due to charging-induced specimen damage or imaging artifacts (as all internal and external features are carbonized and equally conductive). Images of cellular structure could be attained deep within tissue cavities of mechanically sectioned or FIB'ed organs.

To investigate shape-preserving transformation of specimens into conductive replicas, we pyrolyzed silicified chicken embryo tissues in a tube furnace under both inert ($N_2$ or Ar) and reducing environments (5% $H_2$ in $N_2$) as shown schematically in FIG. 9a. FIG. 9b-h shows images obtained from a carbonized, silica bioreplicated (c-SBR) chicken heart (1,000° C., 12 hours, in Ar), where preservation of the structure was maintained across scales, qualitatively similar to our observations of calcined, silicified tissue (FIGS. 5 and 7). Even more impressive, natural voids and chambers in the heart were maintained (FIG. 9k); and free-standing fibers were observed (FIG. 9h). Such structural details were preserved in various organs, such as in the carbonized heart (FIG. 9b-m) and also in a carbonized liver (FIG. 9n-q), where dense vasculature could be observed.

To investigate gross structural changes that may occur from reductive pyrolysis, we subjected two chicken hearts to a side-by-side comparison with or without silicic acid treatment. For the silicified heart, the relative size changes from the hydrated to dehydrated and dehydrated to pyrolyzed were minor, with the structure maintaining ~94% of its dehydrated size following pyrolysis (FIG. 4c). For the untreated heart (that is, no SBR), the size changes were substantial (FIG. 4d). For any sample, some shrinkage is expected following dehydration. For the untreated heart, we performed a careful sequential dehydration (typically five to seven steps) and subsequent air drying from hexamethyldisilazane (HMDS), which is a common biological specimen dehydration procedure for EM. The overall structure and features of the non-silicified tissue are maintained and shrinkage (in this case ~28%) is expected upon dehydration.

In contrast, the silicified heart displayed much less shrinkage (~7%) and dehydration can be achieved in a single step (air dried from methanol) (FIG. 4c). Further, the differences in size changes between the silicified and untreated heart from the dehydrated state to the pyrolyzed state (~6% and ~57%, respectively) were much more substantial (FIG. 4e).

Figure 8:
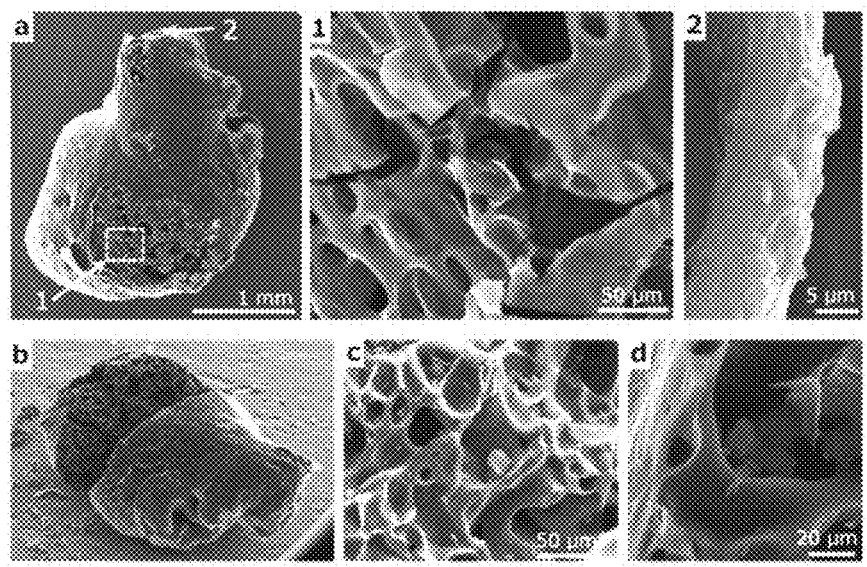
FIG. 8 shows structural loss in a non-silicified, pyrolyzed heart. Provided are SEM images of (a) external features, which are magnified in panels 1 and 2; and (b-d) internal features. As can be seen, panel 1 shows total loss of cellular and extracellular features; and panel 2 shows what appear to be RBC-like shapes. All interior features of the non-silicified, pyrolyzed heart in (b-d) show no discernable biological structures.
Figure 9:
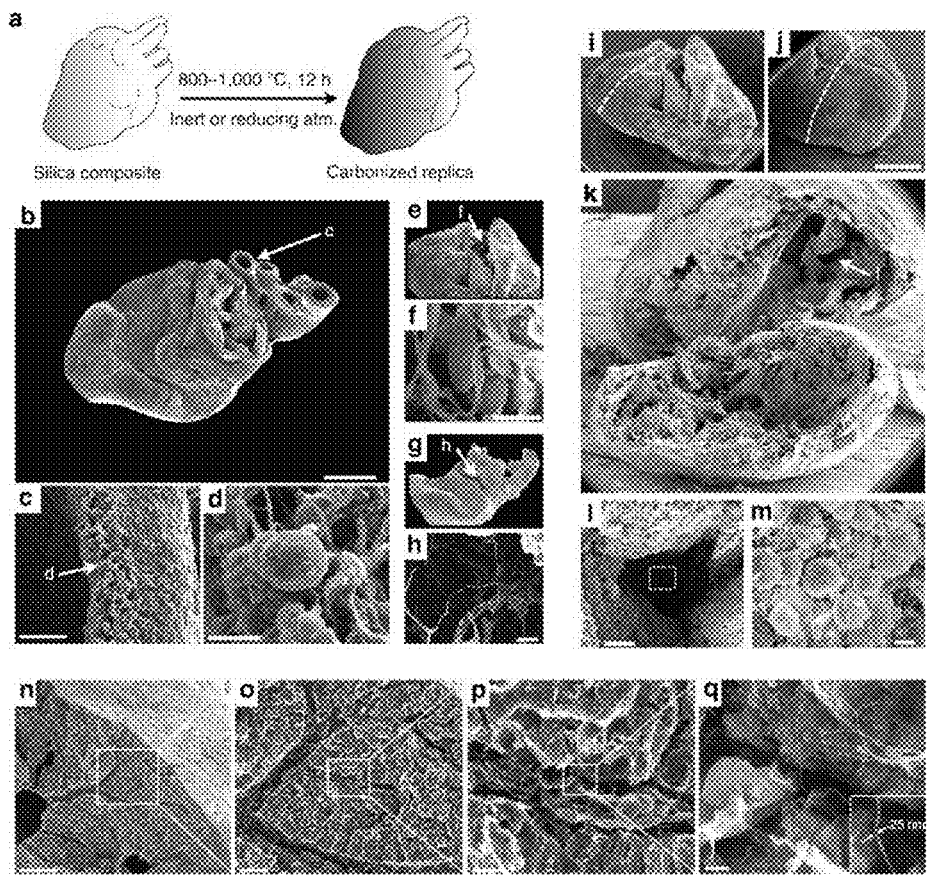
FIG. 9 shows shape-preserving conversion of SBR tissues into conductive constructs. Provided is (a) a schematic showing pyrolysis of a silicified heart into a carbonized silica replica. Also provide are SEM images of (b) a silicified heart that was carbonized at 1,000° C. and without conductive metal coating, where the background is subtracted for clarity; (c,d) increasing magnification of an arterial wall; (e) a crack in the top surface (indicated by arrow) revealing cellular and micro-(~1 µm) to nanoscale (~70 nm) extracellular fibers (shown in f); and (g) a small opening in the side of the heart (indicated by arrow) revealing free-standing fibers and an interior chamber (shown in h). Also provided are SEM images of (i,j) manual sectioning of a carbonized heart revealing the internal chambers (shown in k); (1) deep imaging into the area denoted by the arrow in (k); (m) a further magnified image (of area in dashed rectangle in (1)) revealing surface bound cells ~1.5 mm within the tissue section; and (n-q) increasing magnification of a sectioned carbonized liver showing internal vascularization and resolution of fibrous features (see inset in (q)). Scale bars include (b,j) 1 mm; (c) 30 µm; (d,f,m) 5 µm; (h) 10 µm; (1) 50 µm; and (n-q) 250 µm, 50 µm, 10 µm, and 1 µm, respectively.
Figure 10:
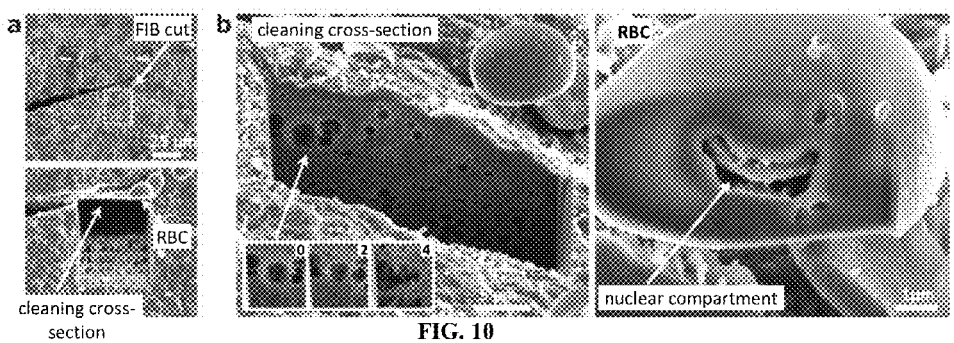
FIG. 10 shows focused ion beam (FIB) milling of a silica bioreplicated and carbonized (c-SBR) chicken liver. Provided are SEM images of (a) the cleaning cross-section of the surface of the liver (top) and a red blood cell (bottom) using 15 nA (~8 minutes milling time); (b, left panel) the face of the cleaning cross-section showing a sinusoidal space that is milled approximately 4 microns further (inset, numbers indicate distance of milling in microns); and (b, right panel) a milled chick red blood cell (RBC) revealing the nuclear compartment (compared to mammalian RBCs, chick RBCs are nucleated).

Most importantly, cellular structure was completely lost in the untreated heart (FIG. 8) versus the silicified tissues and organs (see, FIGS. 7 and 8).

Next, we investigated whether electrical conductivity was maintained throughout the tissue by mechanically sectioning a pyrolyzed embryo heart. As shown in FIG. 9*i-m*, the internal structures of the heart—including the large internal spaces of the heart chambers—remained intact (that is, had not collapsed), and high resolution images of individual cells and surfaces could be acquired deep within the heart chamber (~1-2 mm). Importantly, direct imaging of surfaces deep within tissues using EM presents many challenges. Environmental SEM allows internal imaging of biological structures but is currently only amenable to very thin samples of the order of single cells (see, e.g., de Jonge N et al., "Electron microscopy of specimens in liquid," *Nat. Nanotechnol.* 2011; 6:695-704). Otherwise, internal imaging generally requires serial sectioning of an embedded specimen followed by virtual reconstruction or, alternatively, careful dissection, preparation (fixation/dehydration) and metallization of a specimen. With the latter, any further sectioning would necessitate additional surface metallization.

Here, the intrinsically conductive internal surfaces combined with the dynamic depth of field of an SEM enables imaging deep within internal cavities and allows biomolecular structures to be directly resolved within their 3D context and, if required, subsequent sectioning of the stabilized structure can be achieved manually, mechanically, or by FIB without the need for sputter coating or heavy metal staining. FIB/SEM may prove particularly suitable for c-SBR specimens (FIG. 10) as a means to shorten FIB processing time, which can take days due to the complexities of sample preparation, milling and image processing. To illustrate simple manual dissection of a c-SBR specimen, FIG. 9*n-q* shows a sectioned liver with preservation of features down to ~20-30 nm (FIG. 9*q*, inset). Here, the dense specimen appears to have been sectioned along intrinsic fracture planes (for example, intercellular spaces) revealing a snapshot of internal surface topography, vascular hierarchy, and cellular organization that otherwise would be flattened using mechanical methods of sectioning such as microtome or FIB.

Figure 11:
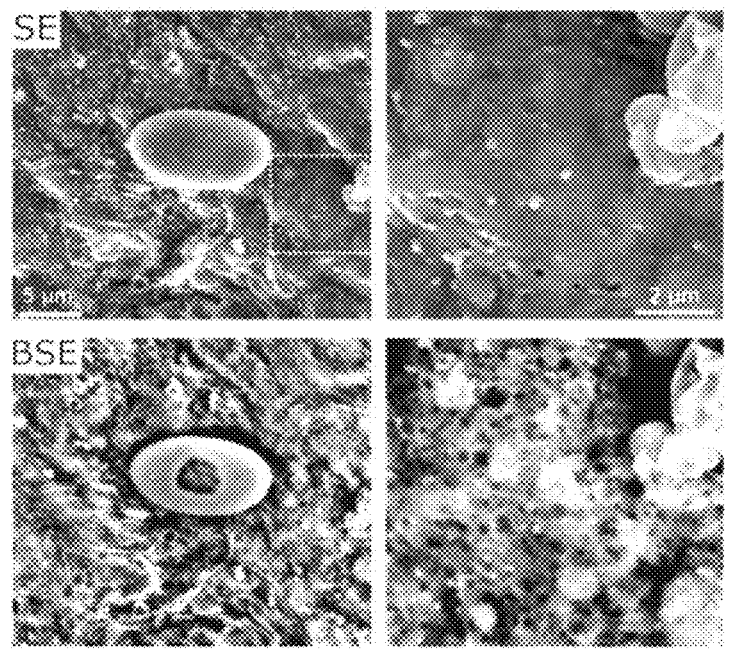
FIG. 11 shows scanning electron (SE) and back-scattered electron (BSE) imaging of c-SBR chicken liver tissue, which revealed sub-surface intracellular and extracellular architecture. The dotted rectangle (top left) was magnified in the right panels. The RBC nuclear region showed void spaces (dark regions) in the BSE image (bottom left), which indicated compacted nuclear material as verified using FIB (see, e.g., FIG. 10).
Figure 12:
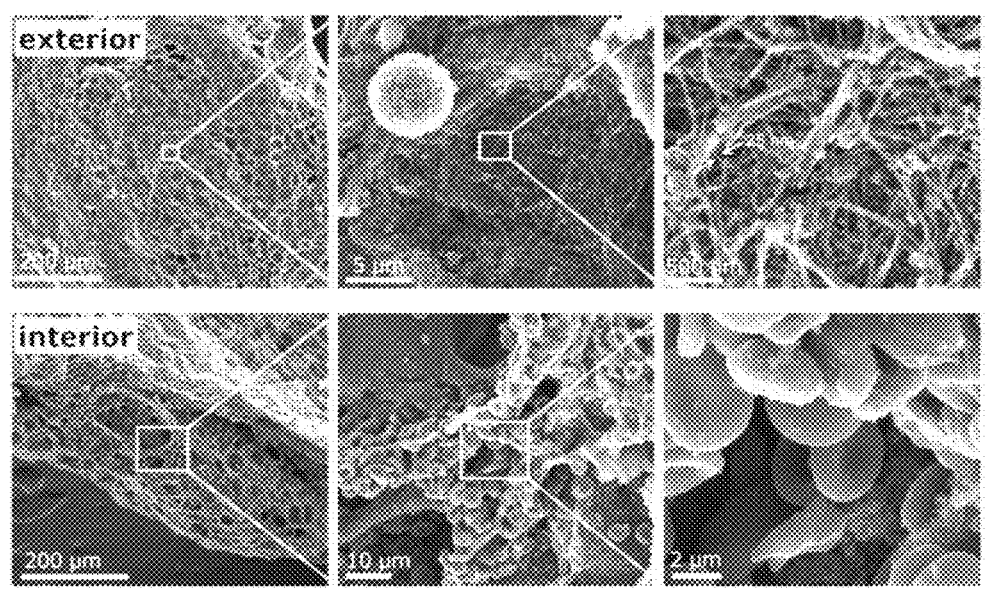
FIG. 12 shows SE imaging of c-SBR mouse spleen tissue, showing the generalizability of the SBR process to different model organisms. Provided are SEM images of (top) the fibrous surface of the exterior capsule and (bottom) the red blood cell-rich internal sinusoids of the red pulp with increasing magnification (from left to right).

The simplicity of the technique, specimen stability, intrinsic conductivity post-carbonization, and level of resolution spanning six orders of magnitude of magnification (that is, whole embryo to subcellular) distinguishes SBR from all previous bio-preservation methods and should facilitate the examination of soft tissues in their native 3D conformation that were previously difficult or impossible to achieve. As an example, as BSEs are scarcer and emanate from a deeper interaction volume (~1-2 microns, see, e.g., Brott L L et al., "Ultrafast holographic nanopatterning of biocatalytically formed silica," *Nature* 2001 September; 413(6853):291-3) in comparison with SE, the sample subsurface could be resolved non-destructively, revealing the architecture underlying a tissue surface (FIG. 11). In addition, the SBR process is generalizable to various model organisms (for example, chicken in FIG. 7 and mouse in FIG. 12) and different organs and tissues, including an entire embryo (FIG. 7), heart (FIG. 9*a-m*), liver (FIGS. 9*n-q* and 11), and spleen (FIG. 12).

Example 3: Nanoparticle Detection in the Interior of an Organ

The resistance to damage of these specimens under high accelerating voltage and beam current provides excellent signal-to-noise ratios using back-scattered electron (BSE) detection allowing, for example, single particle chemical imaging of injected gold nanoparticles (AuNPs) in a fracture plane of a chicken embryo liver.

Gold nanoparticles (AuNPs) were synthesized according to literature, see, e.g., Frens G, "Controlled nucleation for the regulation of the particle size in monodisperse gold suspensions," *Nature* 1973; 241:20-2. Briefly, 20 ml of $HAuCl_4$ (0.1 mg $ml^{-1}$) was titrated against trisodium citrate (10 mg $ml^{-1}$) at 90° C. Two hundred nanometer particles were obtained with ~0.35 ml of trisodium citrate. After heating, the mixture was rapidly quenched in an ice bath, and the particles were washed with centrifugation (500 r.c.f., 5 minutes). After resuspension in DI water, citrate capping was immediately exchanged by drop-wise addition of PEG-thiol in ethanol (MW 5000, 2 mg $ml^{-1}$). The mixture was stirred for 24 hours, and particles were purified again by two cycles of centrifugation. The final product was dispersed in PBS at ~0.25 OD ($\lambda$=600 nm).

The electrical conductivity of these specimens allowed SEM interrogation using high currents (10 s of nA) and accelerating voltages (10-30 kV) that could otherwise damage even metal-coated samples (where metal coatings are typically ~10-20 nm thick). This may allow for chemical/elemental analysis using BSE imaging, which requires high current/kV for sufficient contrast. Considering the increasingly widespread interest in metal and other nanoparticle materials for medicine and derivative studies (for example, nanoparticle toxicology, biodistribution, tissue/particle interactions, see, e.g., Zhang L et al., "Nanoparticles in medicine: Therapeutic applications and developments," *Clin. Pharmacol. Ther.* 2008 May; 83(5):761-9; and Oberdörster G et al., "Toxicology of nanoparticles: A historical perspective," *Nanotoxicology* 2007; 1(1):2-25), the ability to detect nanoparticles in deep tissue, particularly at low densities with single particle resolution and within the intact 3D architecture of the tissue microenvironment, remains a challenge.

Though BSE detection has been occasionally applied to biological materials, examples have required specialized instrumentation (variable pressure/beam deceleration, see, e.g., Ohta K et al., "Beam deceleration for block-face scanning electron microscopy of embedded biological tissue," *Micron* 2012 April; 43(5):612-20; and Ushiki T et al., "Low-voltage backscattered electron imaging of non-coated biological samples in a low-vacuum environment using a variable-pressure scanning electron microscope with a YAG-detector," *J. Electron Microsc. (Tokyo)* 1998; 47(4): 351-4) or sample preparations (for example, single cells grown on conductive substrates, see, e.g., Pluk H et al., "Advantages of indium-tin oxide-coated glass slides in correlative scanning electron microscopy applications of uncoated cultured cells," *J. Microsc.* 2009 March; 233(3): 353-63) that are incompatible with normal tissue development.

Figure 13:
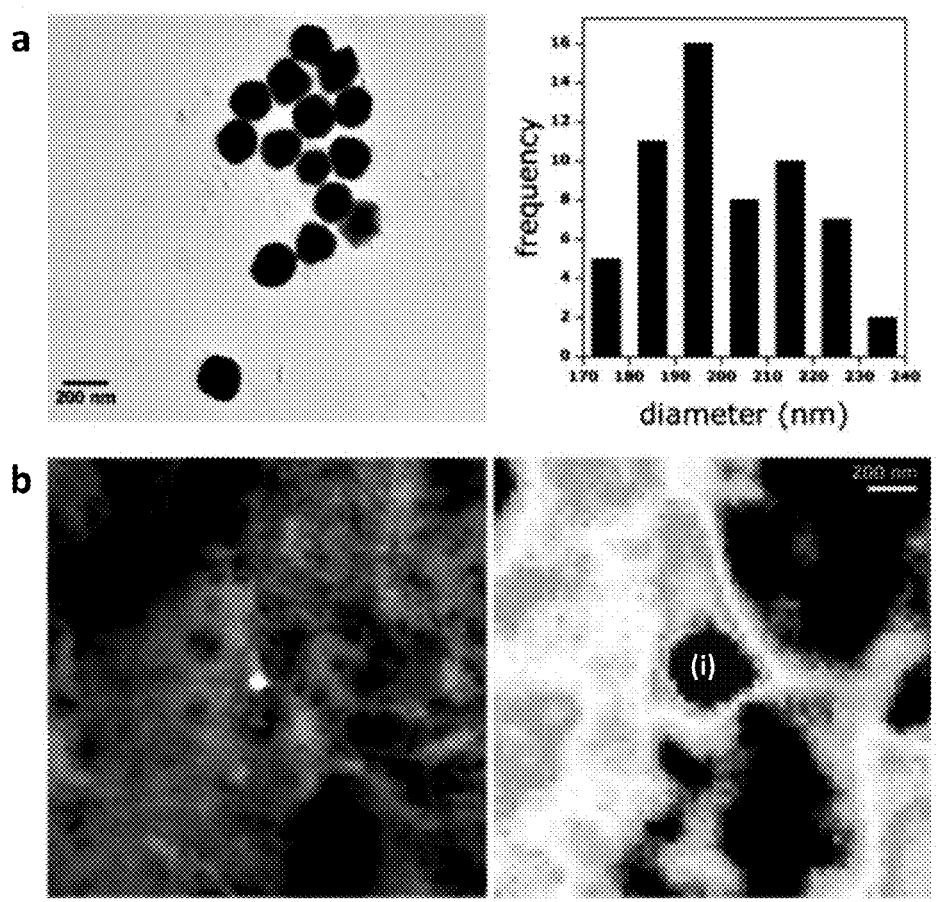
FIG. 13 shows characterization studies conducted on gold nanoparticles (AuNPs). Provided are (a) TEM images and a particle size histogram of AuNPs prior to injection; and (b) a SEM-BSE image of a single particle (left) and an intensity map (right) to determine size. The dark region (annotated as "i") indicates the area of detector saturation and is ~325 nm in diameter indicating detection of a single, overexposed AuNP corresponding to the size of the injected particles.

Thus, we investigated whether SBR carbonization (c-SBR), combined with mechanical sectioning and BSE could detect intravenously injected nanoparticles within tissues. For this experiment, we synthesized 200 nm gold nanoparticles (AuNPs—stabilized with thiolated polyethylene glycol, FIG. 13) and injected them into a 16-day-old chicken embryo. NPs were introduced by direct injection into a vein of the chorioallantoic membrane and were allowed to circulate for 1.5 hours.

Figure 14:
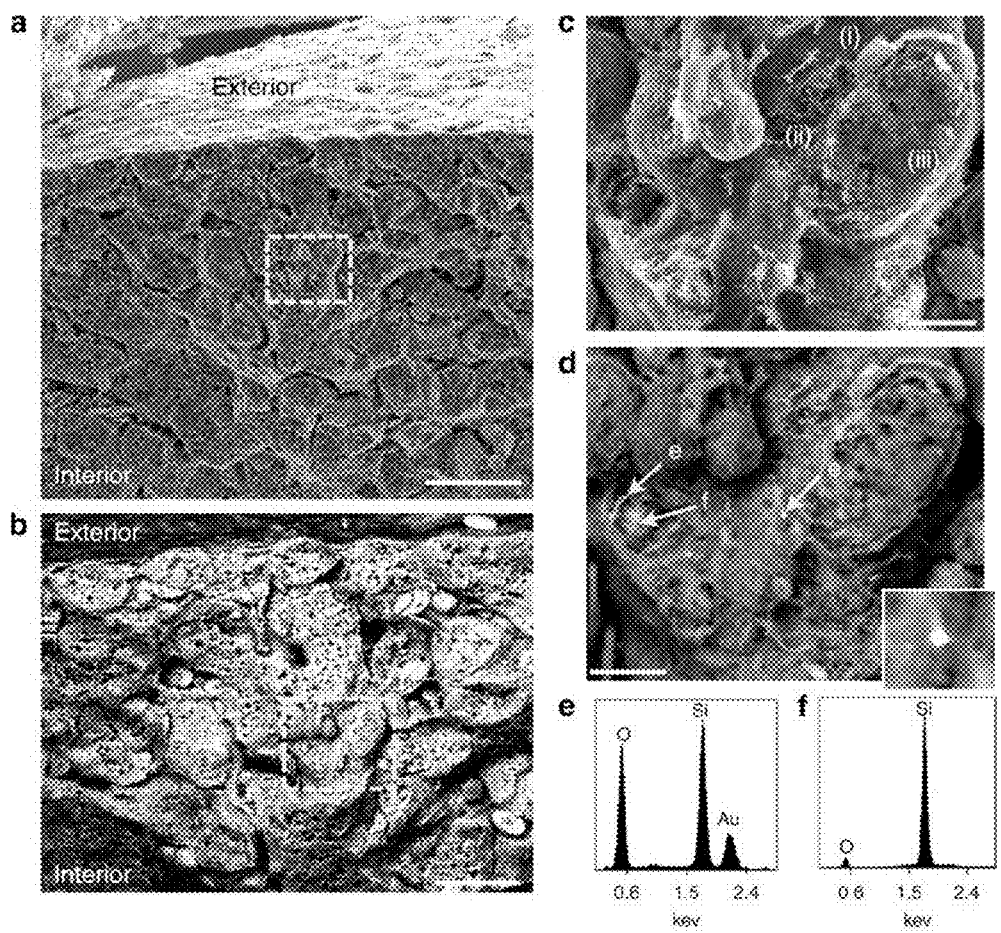
FIG. 14 shows chemical fingerprinting of gold nanoparticles in the interior of a c-SBR chicken liver. Provided are (a) an SEM image of the mechanically fractured chicken liver; and (b) a BSE image of the same region in (a), revealing gross morphology of the internal liver. Also provided are (c) an SEM image of the area within the dashed rectangle in (a), revealing (i) a fenestrated sinusoid, (ii) the space of disse, and (iii) a hepatocyte; (d) a BSE image of the area within the dashed rectangle in (b), revealing single 200 nm diameter AuNPs (inset is a magnification of the center bright spot); (e) a spectrum acquired from the center particle (and representative of spectra obtained from other points denoted as 'e'); and (f) a spectrum acquired from the region 'f' denoted in (d), where these spectra showed relative intensities from single pixel acquisitions of >1,000 counts. Scale bars include (a,b) 50 µm; and (c,d) 5 µm.
Figure 15:
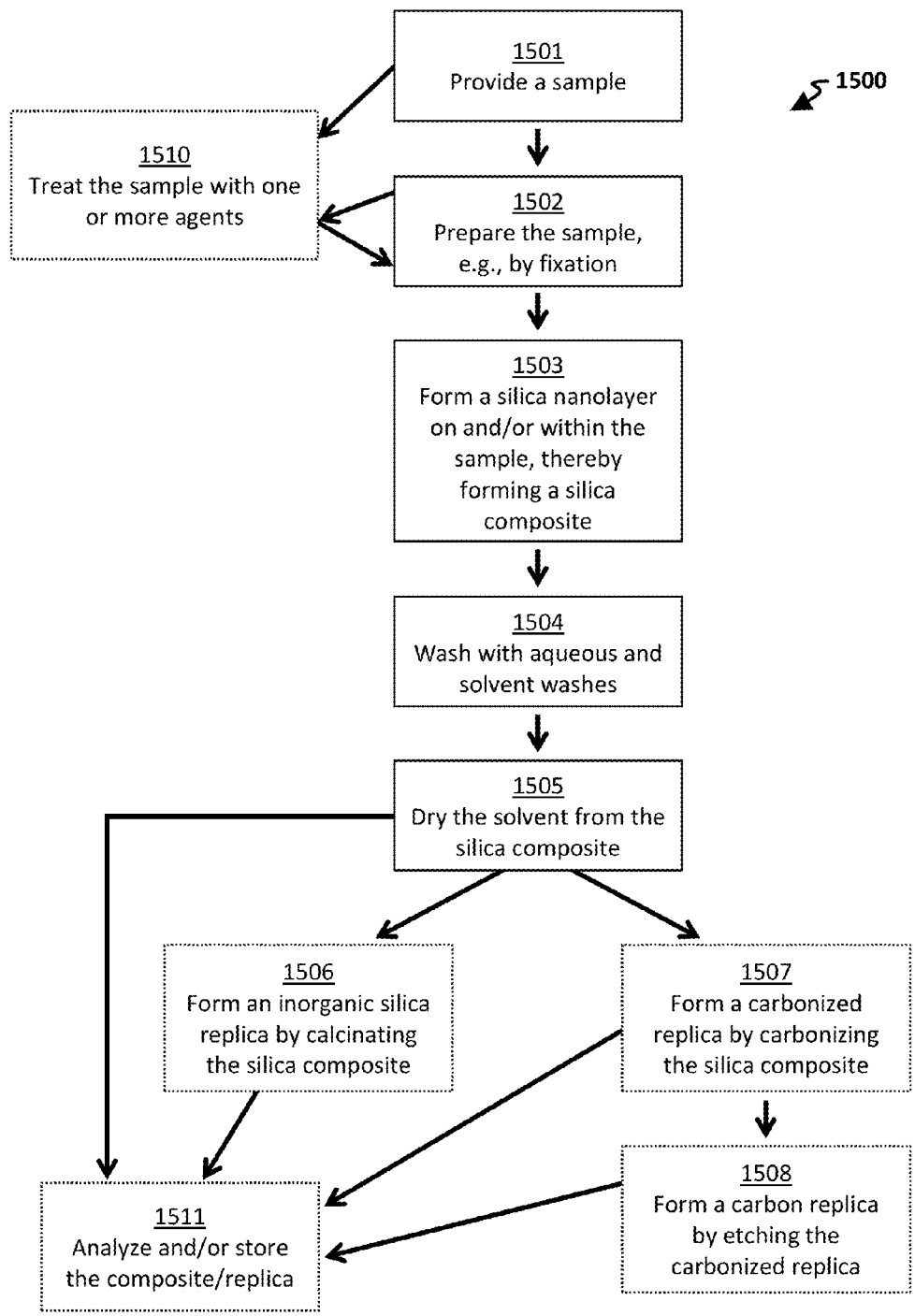
FIG. 15 is a flow chart of an exemplary method 1500 of the invention.

Here, it was expected that AuNPs would deposit preferentially within the liver tissue soon after injection due to their relatively large size (see, e.g., Lipka J et al., "Biodistribution of PEG-modified gold nanoparticles following intratracheal instillation and intravenous injection," *Biomaterials* 2010 September; 31(25):6574-81). After harvesting and preparing the liver (using c-SBR), the tissue was mechanically sectioned across a large lobe to reveal the internal structure (FIG. 14). FIG. 14a,b shows lower magnification secondary electron (SE) and BSE images of the sectioned tissue that provide complementary views. Features such as microvilli and fenestrations were readily identified in SE mode, while subsurface structures including cell nuclei were apparent using BSE detection.

Focusing in and using a driving current of ~20 nA at 10 kV, BSE revealed highly contrasted, individual AuNPs arrested on the walls of the sinusoid endothelium (FIG. 14d). These particles could be chemically fingerprinted in situ from the surrounding background using energy-dispersive X-ray spectroscopy as shown in FIG. 14e,f. BSE detection is essential as the particles were indiscernible from the surrounding tissue using secondary electron (SE) detection (FIG. 14c). This indicated that c-SBR procedures do not appear to detrimentally alter the physical properties of AuNPs, and exemplified the type of problem that is particularly well suited to be addressed using this approach. Depending on instrumentation, imaging conditions, and sufficient Z-contrast with the carbonized specimen, particles that span the size ranges currently investigated for diagnostic and therapeutic applications (10 s of nm to microns) should be detectable.

Our ability to discover and image nano-objects within a biological tissue/organism—finding essentially 'a needle in a haystack'—while maintaining 3D context is a new capability. While complete tissues and organs have been preserved, immunostained, and optically imaged after stabilization within hydrogels and refractive index matching (see, e.g., Chung K et al., "Structural and molecular interrogation of intact biological systems," *Nature* 2013 May; 497(7449): 332-7), further EM characterization of such hydrogel-stabilized samples required multiple steps of solvent exchange, epoxy impregnation to provide stability, staining to provide contrast and ultra-microtoming to achieve thin sections.

Here, stabilization of complete organisms by ultra-thin conformal silica layers formed a mechanically robust, refractory replica allowing transformation to carbon, dissection and EM imaging ad infinitum at different scales of magnification. This procedure has apparent generalizability to other soft tissues derived from model organisms (for example, chicken in FIG. 7, mouse in FIG. 12). Although intracellular structures can be imaged, resolution of such features currently does not approach methods that use sectioning (for example, serial block-face); however, the size of samples that can be used is only limited by the instrumentation implemented for material processing and imaging (for example, size of pyrolysis furnace, chamber volume of SEM and so on). Our procedure to impart shape-preserving, intrinsic conductivity across all specimen planes could inform further design in instrumentation to optimize the resolution of buried features, which may require higher energy fluxes and more sophisticated aberration correction and deconvolution methods.

Example 4: Cellular Complexity Captured in Durable Silica Biocomposites

We hypothesized that naturally crowded molecular environments, such as cells, would also direct silica condensation under similar conditions. To address this question, we incubated chemically fixed mammalian cells in dilute, silicic acid solutions as illustrated schematically in FIG. 18a.

In a typical experiment, cells were maintained in media containing 10% FBS at 37° C. and 5% $CO_2$. Cells were passaged at approximately 80% confluency and then plated onto glass substrates. For fixation, cells in media were rinsed in PBS (pH 7.4) and incubated in 2-4% of a fixative reagent (formaldehyde and glutaraldehyde in PBS produced qualitatively similar results) for a minimum of 10 minutes, followed by rinsing in PBS. Cells were rinsed and immersed overnight (approximately 16-18 hours) in a closed container of 100 mM TMOS in 1 mM HCl at pH 3 and approximately 40° C., resulting in a composite comprising primarily silicon, oxygen, and carbon (cell/silica composites (CSCs) or silica composites, which are used interchangeably herein).

Cell/silica composites (CSCs) were dehydrated by sequential soaking in deionized (DI) water, 1:1 DI water: methanol, and 100% methanol (2×) for 10 minutes in each solution. CSC particles were derived similarly by incubating cell suspensions in TMOS on a shaker. For rinsing and drying, cells were pelleted and redispersed sequentially in rinse solutions (described above) and finally air-dried overnight from 100% methanol. Calcination was performed in air at 550° C. to 600° C. for 3-4 hours, which eliminated the majority of organics. Pyrolysis was carried out at 900° C. in a tube furnace under flowing nitrogen for 4 hours, and silica was etched in 6 M KOH for four days.

Figure 18:
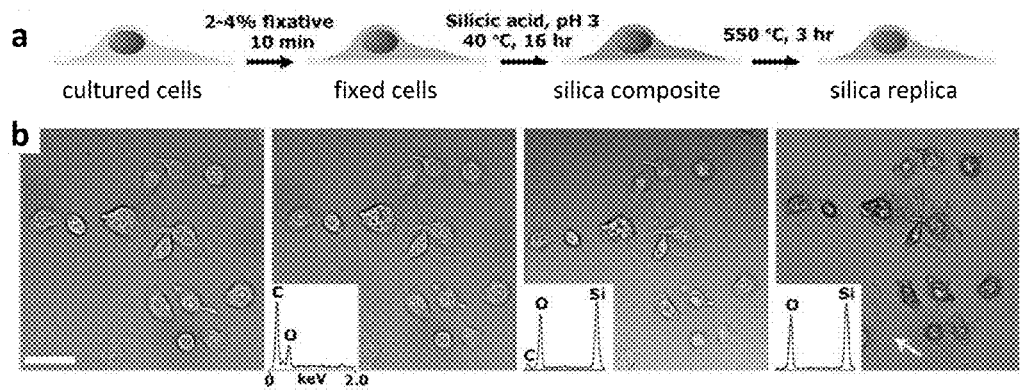
FIG. 18 shows silicification of mammalian cells cultured on flat substrates. Provided are (a) a schematic describing an exemplary SBR process for the mammalian cells to provide a silica replica; and (b) brightfield images of AsPC-1 cells (human adenocarcinoma pancreatic cells) throughout the steps (noted in (a)), including (from left to right) images of hydrated cells, hydrated fixed cells, dehydrated silica composites, and silica replicas. In (b), insets show representative EDS spectra of cells at the various stages.

FIG. 18b shows brightfield images of the identical grouping of differentiated AsPC-1 pancreatic carcinoma cells including the following (from left to right): live cells; cells after fixation; cells after silicification and drying; and cells after calcination at 550° C. We observed structural features and dimensions at each stage of the process to be nearly identical to those of the parent (cell) templates albeit with some minor cracking observed, from SEM images of substrate bound, calcined CSCs. Additionally, features of hydrated living cells that were virtually transparent under brightfield microscopy appeared sharply resolved in calcined CSCs (e.g., the calcined sample imaged in FIG. 18b) due to the increase in refractive index contrast.

Cellular and subcellular morphology is dependent on genetic and environmental factors and therefore can be highly malleable and responsive to, for instance, physical interactions with a substrate. Initial experiments showed that the morphology of cells differentiated on a substrate can be faithfully captured in silica (FIG. 18b). We wished to further explore the procedure under conditions that give rise to more physically homogenous CSCs with high throughput.

Figure 19:
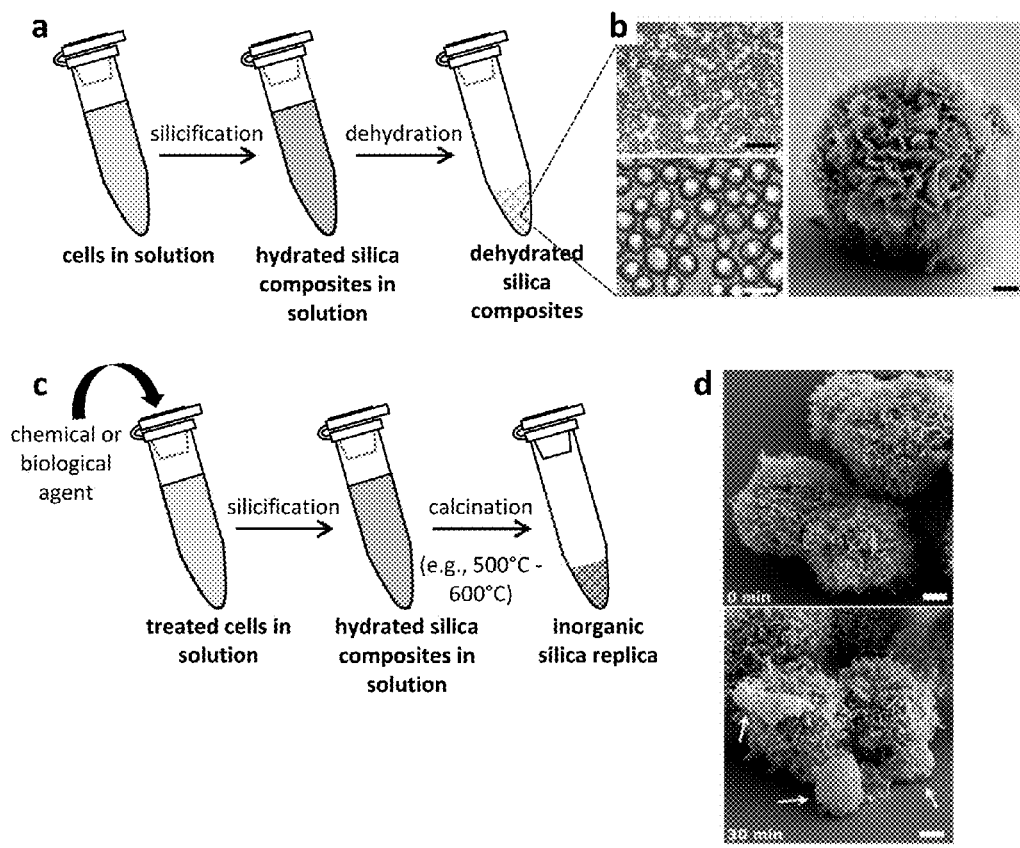
FIG. 19 shows silica composites and silica replicas derived from cell suspensions. Provided are (a) a schematic representing the formation of silica composite particles, including the steps of silification and dehydration to a dry powder including monodisperse, dehydrated silica composites; and (b) an SEM image of a silica composite templated from 4T1 cells (mouse breast cancer mammary cells), displaying a ruffled external surface. Also provided are (b) a schematic representing the formation of inorganic silica replica particles, including the step of treating the cells with a chemical/biological agent, silification, and calcination; and (d) SEM images of clusters of calcined (500° C., 3 hours) silica replicas templated from 4T1 cells that were incubated in 5 µM doxorubicin to induce apoptosis. Arrows denote apoptotic blebs, and scale bars are 2 µm.

Therefore, we fixed and silicified cells under suspension conditions that resulted in a population of essentially monodisperse composite microparticles (e.g., average diameter of 4T1-derived CSCs in FIG. 19b=8.9 μm±1.4) with complex surface features (FIG. 19a,b). Membrane ruffles, filaments, blebs, clusters, and smooth surfaces—common features of cell membrane dynamics—were captured in CSCs and calcined CSCs with high fidelity. Importantly, surface features of silica replicas could be directly modified by inducing cell behaviors, such as apoptosis by treating the cell with a chemical/biological agent (FIG. 19c,d) and surface ruffling prior to silicification. In FIG. 19d, the chemical/biological agent was an anti-cancer drug, doxorubicin, which promoted apoptosis in the 4T1 mouse breast cancer mammary cells.

For fast growing CHO cells (doubling time approximately 12 hours), a standard 225 $cm^2$ flask of adherent cells at 80% confluency (approximately $2.0 \times 10^7$ cells) yielded approximately 10-20 mgs dry weight of CSCs. Use of such fast growing cells indicates a means to rapidly produce gram scale quantities from cell lines, such as CHO, using large capacity bioreactors.

The results from the above series of experiments indicated that the silica deposition process occurred throughout the complete volume of the cell to produce a faithful replica of the exterior and interior cellular structures. Based on the featurelessness of silica deposits in select areas, we concluded that deposition at pH 3 involves weakly charged monomeric or small oligomeric silicic acid species that interact non-covalently with the crowded biomolecular components comprising the cell. The high fidelity replication and self-limiting characteristics suggested a mechanism in which silicic acid is distributed uniformly over and throughout the cell scaffold, where it undergoes acid- or base-catalyzed condensation promoted by the spectrum of proximal functional groups, such as protein surface residues. In this manner, the process is inherently self-limiting to form a continuous silica replica throughout the cell.

Remarkable is that the silicified cell, although nanostructured, withstands drying and sintering to 550° C. with minimal shrinkage. Generally, drying (capillary) and sintering stresses would result in enormous volumetric changes for an untreated cell. The absence of appreciable shrinkage speaks to the mechanical integrity of the cell-catalyzed silica replica. The absence of primary particles and microporosity reduces greatly both drying and sintering stresses, which scale roughly inversely with particle or pore size. Without wishing to be limited by mechanism, one hypothesis consistent with these observations is that at pH 3, where silicic acid monomers and oligomers are uncharged, silicic acid incorporates within the continuous hydrogen bonded water network encompassing cellular surfaces where it becomes locally concentrated and subsequently condensed amphoterically via surface moieties (e.g., acidic and basic protein residues).

In essence, the structural complexity of cells was captured via self-limiting nanoscale replication in a hard material, providing a platform in which to preserve and reconstitute cellular functions. For example, amphiphilic lipid bilayers introduced as liposomes localize (selectively as compared to on the adjoining substrate) on the outer surfaces of CSCs demonstrating that the membrane lipid component could, in principle, be reconstituted. Subsequent, incubation with a lipid diffusible fluorogenic stain used to assess cellular viability indicated retention of some level of enzyme activity. Sequestration of the dye (based on esterase cleavage to form a lipid insoluble fluorophore) was observed in CSCs supporting lipid membranes versus calcined CSCs. These results provide an avenue to begin to explore CSCs as an alternative route to biocatalyst stabilization, where the current state-of-the-art employs prefabricated (mesoporous) silicas for subsequent enzyme loading. By using this general approach as a starting point, more complex and specific biocatalyst stabilization can be targeted, by stabilizing enzymes and enzyme complexes in their optimized, crowded in vivo configurations.

Finally, the ability to replicate both surface and intracellular molecular architectures with silica provided opportunities to investigate shape-preserving chemical transformations of CSCs to other materials. To begin to explore these properties, we investigated the ability of CSCs to render porous carbon structures, a class of materials with substantial utility in fuel cell, decontamination, and sensor technologies. We subjected CSC particles to high-temperature pyrolysis conditions (900° C., 4 hours, under $N_2$ atmosphere), which resulted in an opaque powder (FIG. 20a,b) with individual particles, i.e., carbonized-cell/silica composites (c-CSCs). The c-CSCs displayed similar morphologies to that of the starting material (FIG. 20c).

Figure 20:
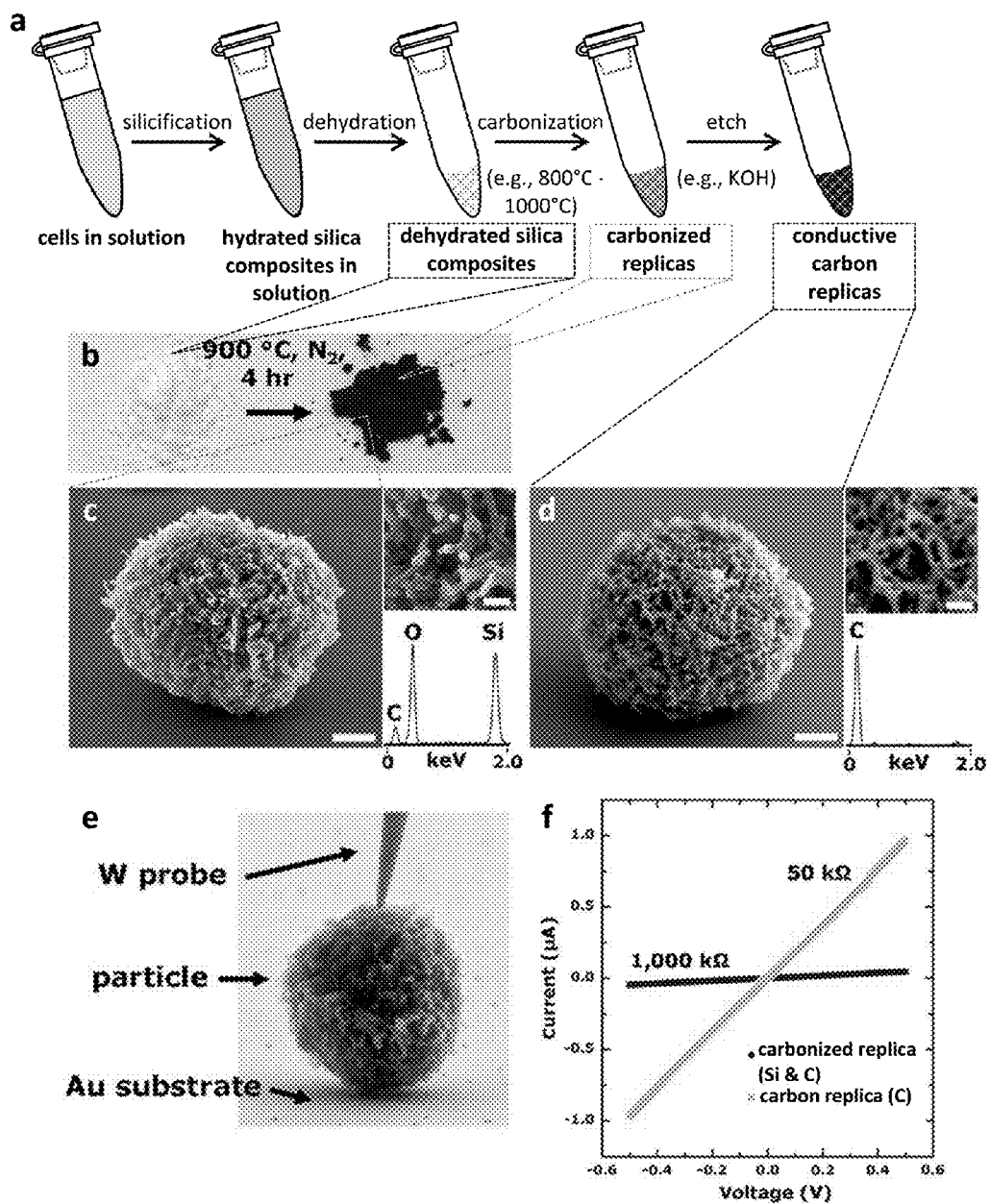
FIG. 20 shows shape-preserved, c-SBR processed 4T1 cells resulting in carbonized replicas and carbon replicas. Provided (a) a schematic representing the formation of silica composite particles, including the steps of silification and dehydration to a dry powder, carbonization (pyrolysis) to provide a carbonized replica, and etching to provide a carbon replica; (b) a photograph of silica composite particles (left, white powder) and the resultant carbonized replicas (right, black powder) after pyrolysis; and (c) SEM images of a carbonized replica having retained cellular structure and an EDS spectra. Etching of the silica (in the carbonized particle) produced a carbon-rich replica, as shown in (d) an SEM image and EDS spectra of the carbon replica; (e) an SEM image during in situ electrical characterization of a replica; and (f) a graph showing a 20-fold decrease in electrical resistance across a replica following silica etching. Scale bars include (b,c) 2 µm; and (insets) 500 nm.

Subsequent dissolution of the silica support (using 6 M potassium hydroxide (KOH), 4 days) resulted in free-standing carbon particles retaining cellular morphologies (FIG. 20d). Electrical measurements were conducted on the carbon particles, which were placed onto gold coated coverslips. IV curves were performed using a one-probe nano-manipulator retro-fit inside of a JEOL 6701F scanning electron microscope. Current and voltage were measured and controlled between the probe and substrate using an Agilent B1500A semiconductor device analyzer. Probe tips were polycrystalline tungsten wire electrochemically etched to an end radius of curvature of less than 250 nm.

In situ SEM electrical characterization (FIG. 20e) showed ohmic conductivity through the particles. Representative current-voltage (IV) curves for c-CSCs and carbon replicas are shown in FIG. 20f. Note that removal of the insulative silica support decreased particle resistance approximately 20-fold. These results indicated that the wide heterogeneity of in vitro soft cellular architectures can now be considered for use as a feedstock for most materials processing procedures, including those requiring high temperature and pressure.

We have described a simple approach to derive functional biomorphic composites, silica frustules, and carbon replicas from mammalian cells, which should allow straightforward customization of structure and function via chemical and genetic engineering. This procedure does not require prein-filtration of templating molecules (e.g., cationic polymers) or multistep layer by layer assembly and is distinct from other inorganic biotemplating strategies that simply coat external surfaces to produce hollow shells or low fidelity inverse structures following calcination.

In contrast to the majority of studies describing cell encapsulation in silica where the primary goal of maintaining cell viability necessitates reaction conditions near neutral pH and cells become physically entrapped within (non-conformal) gels, here the charge of silicic acid is essentially neutral (pH 3) and thus hydrogen bonding and other non-covalent silica/molecular interactions govern deposition. To date, individual cellular/biomolecular components, peptides, proteins, lipid vesicles, polysaccharides, cytoskeletal filaments, etc. have all been shown to interact with, and often template silica in vitro but with no control over 3D structure. Presented on and within a cell, these collective silica/molecular interactions are exploited here under molecularly crowded environments using stable sols (e.g., limited homopolymerization, no gel formation, etc.), such that deposition is targeted to cell structures, resulting in a process that is inherently conformal and self-limiting due to slow solution silica polymerization kinetics. The apparent generalizability of this process should allow for the synthetic production of complex and durable composites and minerals with structural diversity approaching that of natural biomineralizing microorganisms.

Example 5: Mechanically Encoded Cellular Shapes for Synthesis of Anisotropic Mesoporous Particles The asymmetry that pervades molecular mechanisms of living systems increasingly informs the aims of synthetic chemistry, particularly in the development of catalysts, particles, nanomaterials, and their assemblies. For particle synthesis, overcoming viscous forces to produce complex, non-spherical shapes is particularly challenging; a problem that is continuously solved in nature when observing dynamic biological entities such as cells. Here, we bridged these dynamics to synthetic chemistry and show that the intrinsic asymmetric shapes of erythrocytes can be directed, captured, and translated into composites and inorganic particles using a process of nanoscale silica-bioreplication. In this example, we show that crucial aspects in particle design such as particle-particle interactions, pore size, and macromolecular accessibility can be tuned using cellular responses. The ability to use cellular responses as "structure directing agents" offers an unprecedented toolset to design colloidal-scale materials.

The success of living systems rests upon a mastery of molecular to microscale assemblies and materials. Multi-scale processes such as metabolism, cell communication, and development rely on evolutionarily optimized structures to dictate function where the common thread of asymmetry pervades key aspects of these systems—from ligand receptor interactions to construction of hierarchical tissues. These principles increasingly inform synthetic chemistry and materials science; this is reflected, for instance, in recent aims of colloid chemistry where the development of asymmetric, anisotropic, patchy, Janus, and other non-spherical particles has gained substantial momentum and use across technological applications, materials engineering, and fundamental studies of self-assembly and recognition (see, e.g., Walther A et al., "Janus particles: synthesis, self-assembly, physical properties, and applications," *Chem. Rev.* 2013 Jul. 10; 113(7):5194-261; Lee K J et al., "Recent advances with anisotropic particles," *Curr. Opin. Colloid Interface Sci.* 2011 June; 16(3):195-202; Glotzer S C et al., "Anisotropy of building blocks and their assembly into complex structures," *Nat. Mater.* 2007 August; 6(8):557-62; and Helgeson M E et al., "Hydrogel microparticles from lithographic processes: novel materials for fundamental and applied colloid science," *Curr. Opin. Colloid Interface Sci.* 2011 Apr. 1; 16(2):106-117).

However, the development of non-spherical particles with prescribed shapes presents particular challenges given that bulk syntheses (e.g., solution or aerosol phase) of colloidal-scale materials tend to produce spherical particles due to the dominance of viscous and capillary forces (i.e., surface tension). This challenge, in part, has been overcome using a variety of strategies (see, e.g., Shum H C et al., "Droplet microfluidics for fabrication of non-spherical particles," *Macromol. Rapid Commun.* 2010 January; 31(12):108-18; Yin Y et al., "Template-assisted self-assembly: a practical route to complex aggregates of monodispersed colloids with well-defined sizes, shapes, and structures," *J. Am. Chem. Soc.* 2001 September; 123(36):8718-29; Roh K H et al., "Biphasic Janus particles with nanoscale anisotropy," *Nat. Mater.* 2005 October; 4(10):759-63; Dendukuri D et al., "Continuous-flow lithography for high-throughput microparticle synthesis," *Nat. Mater.* 2006 May; 5(5):365-9; and Merkel T J et al., "Scalable, shape-specific, top-down fabrication methods for the synthesis of engineered colloidal particles," *Langmuir* 20010 August; 26(16):13086-96).

Despite these achievements, we still cannot synthetically mirror the complexity and precise control over shape observed in cells and microorganisms. This does not deter efforts but provides an inspirational pathway to achieve ever-higher complexity by developing foundational strategies from mimicking less elaborated shapes.

As an example, consider a mammalian erythrocyte (red blood cell, RBC). The characteristic biconcave discoid shape (termed a discocyte) provides excess surface area (40% compared to a sphere of the same volume), which ultimately gives rise to the majority of the mechanical and transport properties of RBCs by enabling extreme shape deformations (see, e.g., Mohandas N et al., "Red cell membrane: past, present, and future," *Blood* 2008 November; 112(10):3939-48). These morphological and mechanical properties offer an explicit challenge for materials design and, as such, have been a target for efforts to synthesize particles that mimic RBC shapes and functions (see, e.g., Haghgooie R et al., "Squishy non-spherical hydrogel microparticles," *Macromol. Rapid Commun.* 2010 January; 31(2):128-34; Doshi N et al., "Red blood cell-mimicking synthetic biomaterial particles," *Proc. Natl. Acad. Sci. USA* 2009 December; 106(51):21495-9; and Merkel T J et al., "Using mechanobiological mimicry of red blood cells to extend circulation times of hydrogel microparticles," *Proc. Natl. Acad. Sci. USA* 2011 January; 108(2):586-91).

Given their lack of immune recognition and long circulation times, natural RBCs and their membrane components have been extensively investigated as therapeutic agents, but it is their extreme sensitivity to chemical and environmental changes—both of which are required for functionalization and/or drug loading—that has motivated efforts to improve durability by developing synthetic mimics and membrane/synthetic hybrid materials (see, e.g., Hu C M et al., "Erythrocyte-inspired delivery systems," *Adv. Healthcare Mater.* 2012 September; 1(5):537-47). However, it is the concerted shape changes that RBCs undergo in response to chemical perturbation (FIG. 21*a*)—a response encoded mechanically in the membrane dynamics (FIG. 21*b*) (see, e.g., Sheetz M P et al., "Biological membranes as bilayer couples: A molecular mechanism of drug-erythrocyte interactions," *Proc. Natl. Acad. Sci. USA* 1974 November; 71(11):4457-61)—which is intriguing to consider in the context of developing colloidal-scale non-spherical particles, that is, provided an ability to translate these shapes into more durable materials.

Figure 21:
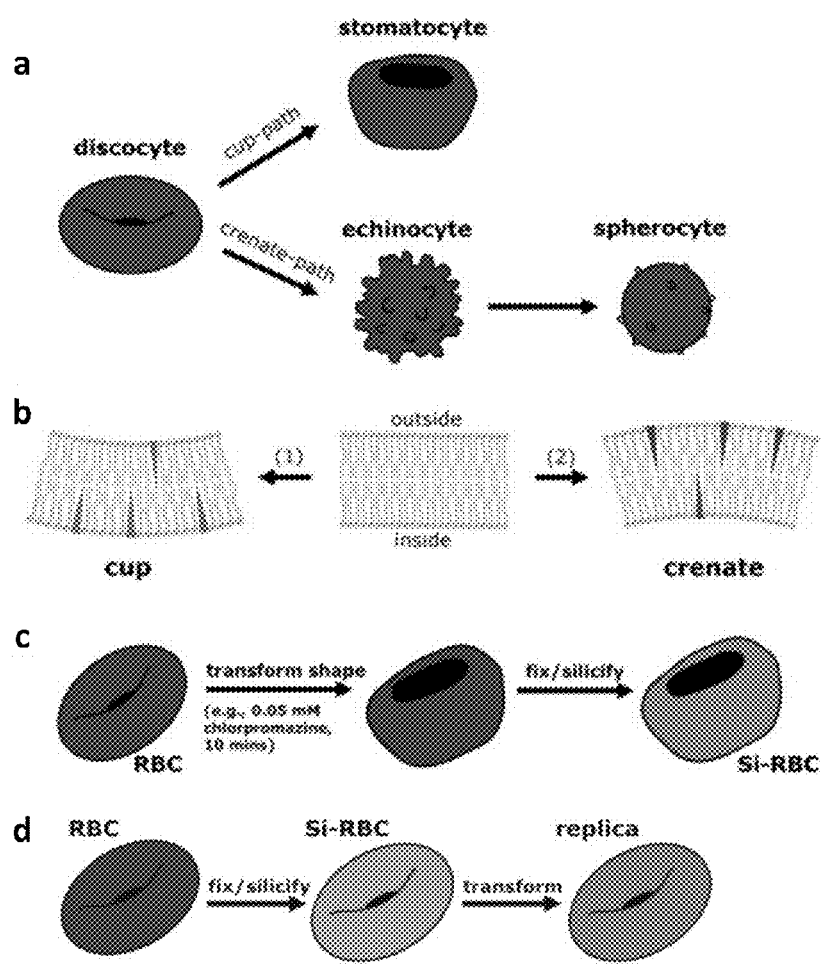
FIG. 21 shows composite and replica particles derived from red blood cells (RBCs) and shape-encoded RBCs. Provided are (a) a schematic of the sequence of shapes displayed by RBCs; (b) a schematic showing how shape changes can be driven by chemical agents preferentially inserting into (1) the inner leaflet or (2) the outer leaflet of the lipid bilayer to form cup or crenate shapes, respectively; (c) a schematic showing generation of a cup-shaped constructs via silica bioreplication (SBR) to provide a silica composite of the RBC (or Si—RBC); and (d) a schematic showing generation of particles via SBR to provide either a silica composite (Si—RBC) or a replica.

Here, we systematically derived the RBC shape continuum (FIG. 21*a*) via perturbation of the RBC bilayer using crenating and cup-forming agents (FIG. 21*b*) and translated these forms into composite and inorganic colloidal scale porous materials using a process of silica bioreplication (SBR; FIG. 21*c,d*). Exemplary crenating and cup-forming agents, as well as their expected perturbations of the RBC bilayer, are described in, e.g., Wong P, "A basis of echinocytosis and stomatocytosis in the disc-sphere transformations of the erythrocyte," *J. Theor. Biol.* 1999 Feb. 7; 196(3):343-61, which is incorporated herein by reference in its entirety.

Shape-encoded composites and replicas were obtained by employing RBCs as the sample source. In brief, RBCs were acquired from healthy donors with their informed consent by purification of whole blood using the Ficoll® density gradient centrifugation procedure. Then, RBCs were incubated in treatment solutions to form the particle libraries (excluding discocytes, which were used immediately to generate Si—RBCs). To generate stomatocytes, cells were incubated in 50 µM chlorpromazine for 10 minutes. For echinocytes, cells were incubated in 0.6 mM 2,4-dinitrophenol for 2 minutes; alternatively, cells were incubated in a hypertonic solution for up to 1 hour. We observed that incubation in 0.3 to 1.0 M NaCl generally resulted in the same final shape composition of echinocyte Si—RBCs (1:1 echinocyte I:II). Spherocytes were generated by incubating cells in 10 mM Tris HCl, 146 mM NaCl for 24 hours. We note that each of these procedures required optimization depending on various factors (time following donation, individual donor, etc.). Observed shape yields for each library included the following: stomatocytes, ~90%; discocytes ~90%; echinocytes, ~50% echinocyte I and ~50% echinocyte II, III; and spherocytes, 98% of total particles.

Si—RBCs were generated by performing the SBR process on native RBCs or shape-encoded RBCs. In brief, RBCs were fixed in 4% formaldehyde in phosphate buffered saline (PBS) at room temperature for 16-24 hours. Cells were rinsed in PBS followed by rinsing in 0.154 M NaCl dissolved in deionized water (0.9% saline). Fixed RBCs were immersed in a solution containing 0.1 M TMOS hydrolyzed in 0.9% saline containing 1.0 mM HCl (pH 3) and incubated in closed containers for 16-24 hours at 37° C. Si—RBCs were dried by rinsing in deionized water (dH$_2$O), followed by 1:1 dH$_2$O:methanol, and 100% methanol (2×) for 10 minutes in each solution and allowed to dry in air. To generate particles miscible in organic solvents, following methanol rinsing, particles were rinsed in 1:1 methanol: HMDS (hexamethyldisilazane) then 100% HMDS (2×) for 10 minutes in each solution and subsequently dried in air.

To generate discocyte-shaped particles, purified RBCs were fixed prior to silicification. Cells were subsequently silicified in a saline solution at 40° C. containing 0.1 M silicic acid (derived from hydrolyzed tetramethyl orthosilicate, TMOS) adjusted to pH 3 for 12-18 hours. Under these conditions (pH and silicic acid concentration), the solutions are highly stable and displayed no gelation (self-condensation) over the course of weeks. Thus, silica deposition was limited to cellular surfaces—both internal and external—via a self-limiting mechanism that restricted silica layers to <10 nm. To achieve a large proportion of discocytes, cells were used immediately in the above-described method. After the silica solution was rinsed, particles were dried in air from high vapor pressure solvents such as methanol and hexamethyldisilazane (HMDS).

Figure 22:
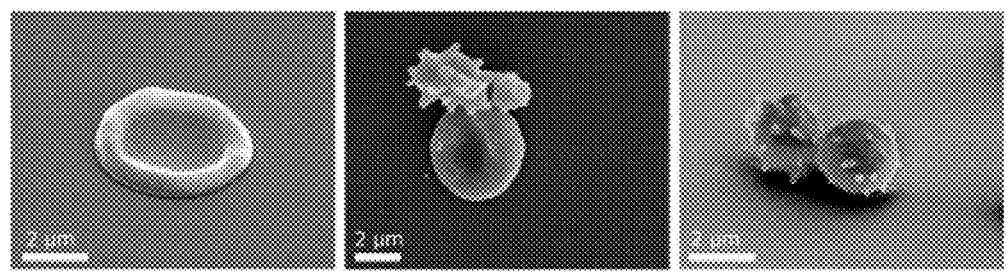
FIG. 22 shows SEM images of Si—RBCs from commercial blood sources having various morphologies.
Figure 23:
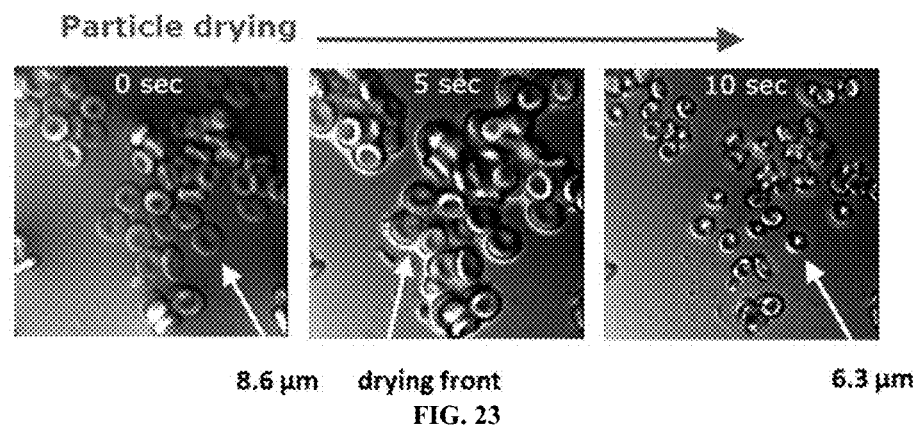
FIG. 23 shows optical microscope images of Si—RBC particle shrinkage following initial drying from a solution of methanol.

As can be seen in FIG. 22, various morphologies can be observed in silica composites obtained from RBCs (Si—RBCs), including crenated morphologies. Upon drying, we observed a uniform shrinkage of discocyte composite particles. FIG. 23 shows a single, flat-lying cell undergoing a change in diameter from 8.6 μm to 6.3 μm during drying. Assuming a normal cell volume of 90 fL, this decrease in diameter reduced the volume by ~55% (~40 fL, assuming minimal change in discocyte height of ~1.5 μm). RBCs can display a wide range of cell volumes (20-200 fL) but cytoplasmic viscosity is tightly controlled by regulating hemoglobin concentration within a narrow range, and even minor (3-4%) changes in surface area can result in cell lysis. This volume loss appeared to be largely accommodated in composite discocytes by a compaction of the shape, resulting in a relatively pudgier morphology compared to normal, hydrated cells. SBR appeared to impart mechanical stability to the cellular architecture during drying-induced stress; no cracking, lysing, or other morphological changes were observed.

Employing this general approach, we generated a range of silica composite particle libraries templated from the RBC shape sequence (Si—RBCs). The results are summarized in FIG. 24a-24d. Stomatocyte formation can be induced using cationic amphipaths, such as the antipsychotic drug chlorpromazine. Echinocyte formation can be induced with anionic amphipaths, high salt, and/or ATP depletion, which ultimately produces spherocytes, the most dense/compacted RBC shape. Both stomatocyte and echinocyte formation involved relatively short treatments (≤10 minutes) prior to fixation; spherocyte particles were developed over longer treatment times (~24 hours) using ATP depletion.

Figure 24:
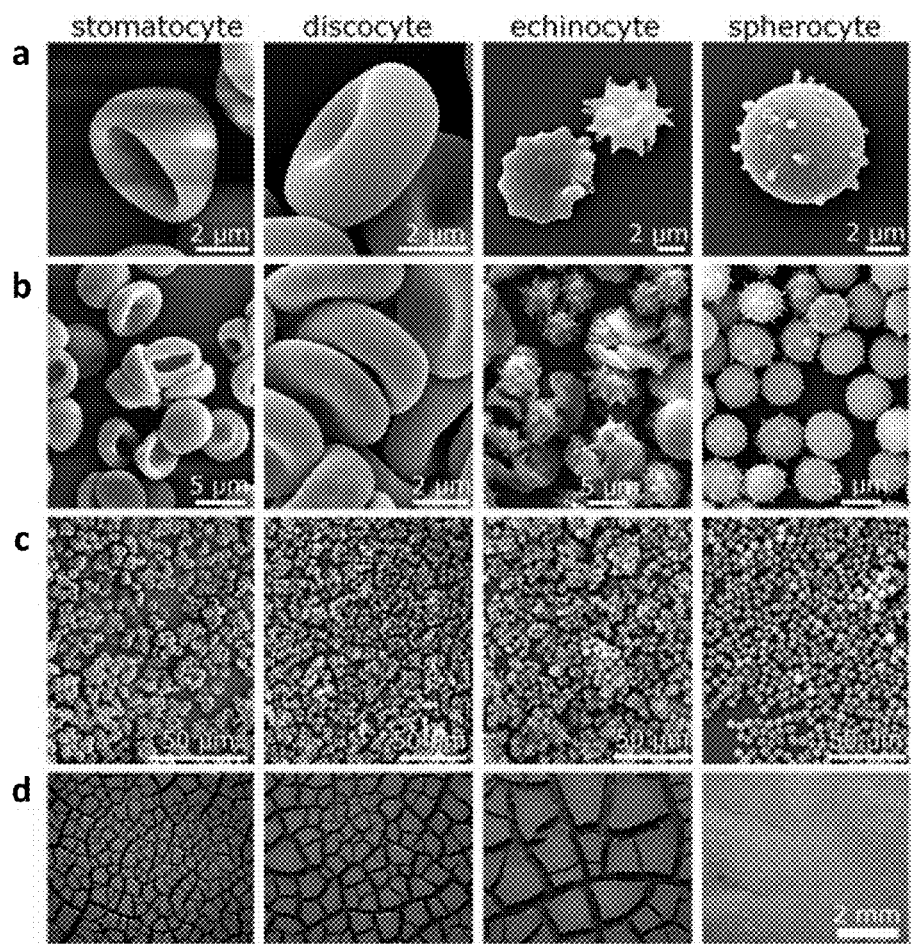
FIG. 24 shows generation of four distinct libraries of Si—RBC particles templated from RBCs. These four libraries include stomatocytes (first column), discocytes (second column), echinocytes (third column), and spherocytes (fourth column). Provided are (a-c) SEM images showing decreasing magnification; and (d) panels show cracking patterns observed following drying in air from methanol.

Libraries with high yield of the target shapes were achieved for stomatocyte, discocyte, and spherocyte particles. However, synthesis of echinocytes using a range of chemical treatments consistently yielded a mixed population of both flattened (echinocyte I) and spikey (echinocyte II and III) crenated morphologies following drying (FIG. 24a-24c). The energy difference between these two forms is small (see, e.g., Lim H W G et al., "Stomatocyte-discocyte-echinocyte sequence of the human red blood cell: evidence for the bilayer-couple hypothesis from membrane mechanics," Proc. Natl. Acad. Sci. USA 2002 December; 99(26): 16766-9). Increasing the concentration of crenating agents still yielded a significant fraction of the flattened echinocyte I shape. Enrichment of echinocyte I and II populations potentially can be achieved using separations designed for non-spherical bioparticles (see, e.g., Zeming K K et al., "Rotational separation of non-spherical bioparticles using I-shaped pillar arrays in a microfluidic device," Nat. Commun. 2013; 4:1625).

Figure 25:
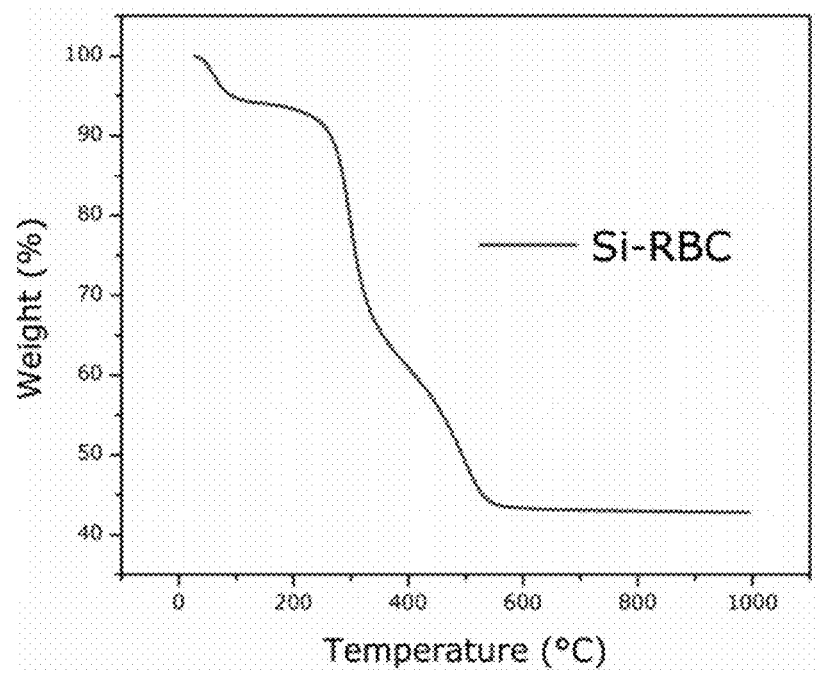
FIG. 25 is a graph showing a TGA curve of Si—RBCs produced by the SBR process and recorded in air.
Figure 26:
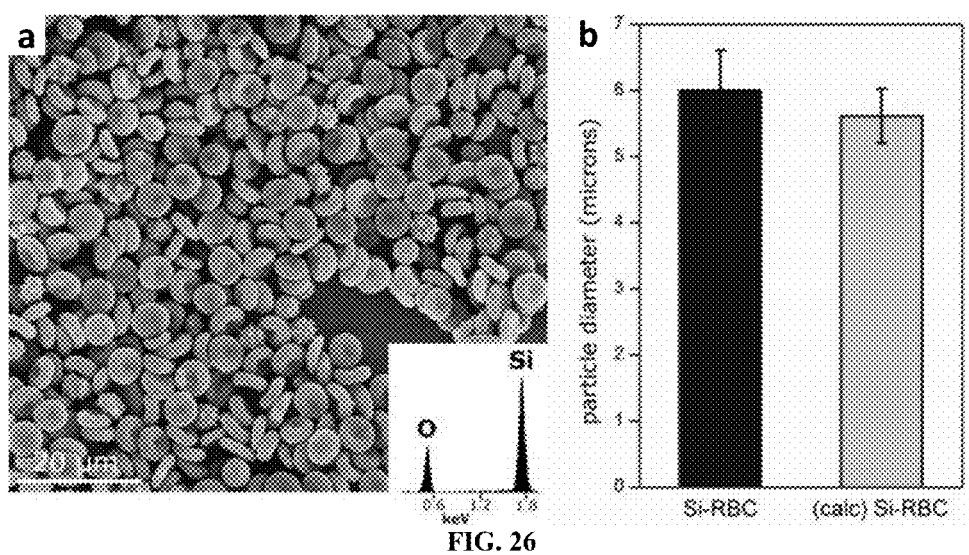
FIG. 26 shows that calcination of Si—RBCs (500° C., 4 hours) did not significantly alter size and shape. Provided are (a) SEM images (left) and an EDS spectrum (right) of the Si—RBC replica particles; and (b) a graph of measured diameters of Si—RBC composites (left) and Si—RBC replicas (i.e., Si—RBC composites that have been calcined, labeled as "(calc) Si—RBC") (right) (n=50).

These libraries of distinctly shaped particles could be synthesized in scalable quantities. We found that approximately 4.5-5 mL of whole blood consistently yielded 1 g of dry dispersed particles (~1,010 particles per gram). Silica replicas of Si—RBC shapes were obtained following calcination (550° C., 4 hours). Thermogravimetric analysis (TGA) showed that calcination to ~550° C. resulted in ~53% weight loss (FIG. 25) from volatilization of the organic template and was accompanied by only minor shrinkage (~6% in diameter) and no discernible fracturing or change in shape compared to the starting material (FIG. 26).

Figure 27:
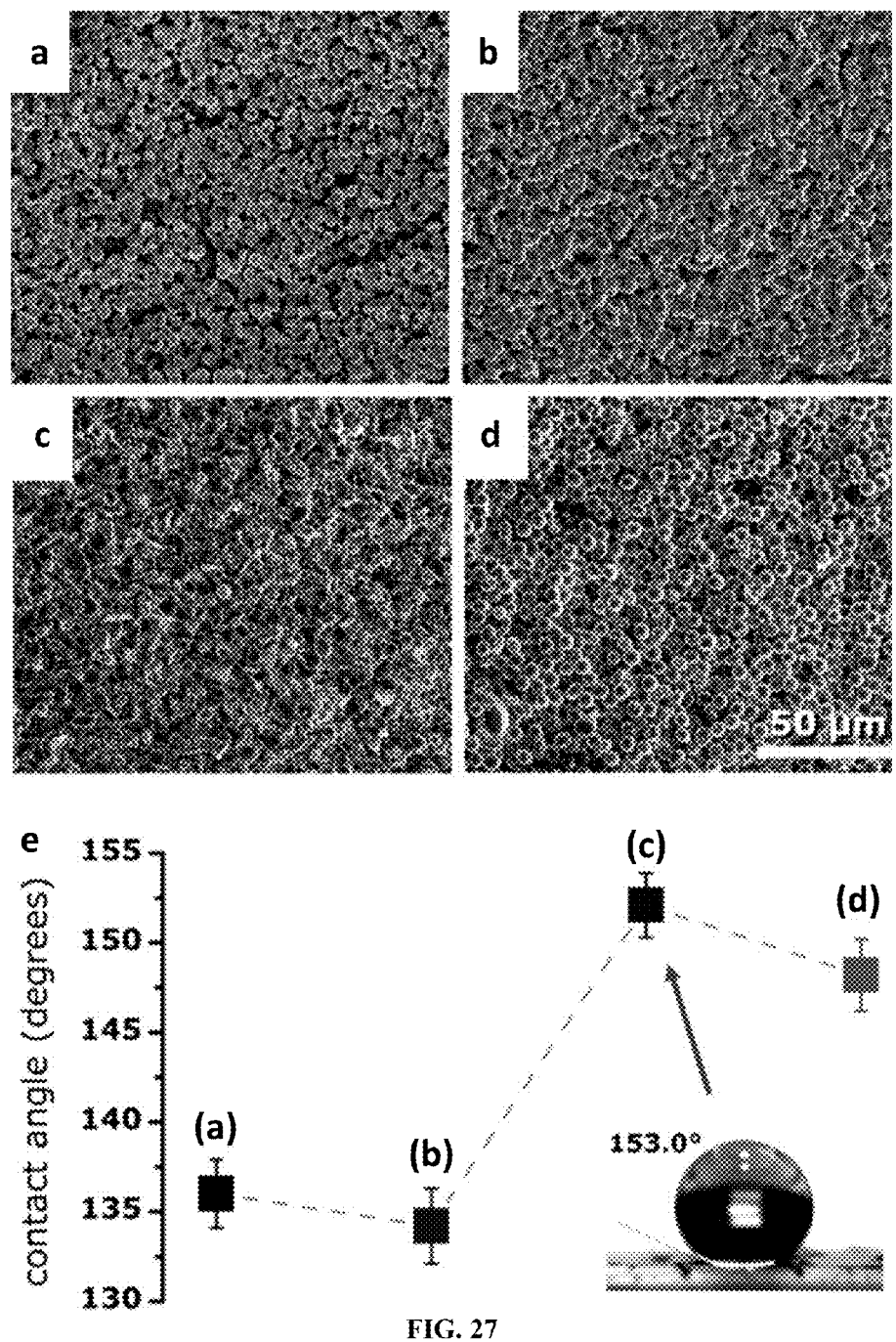
FIG. 27 shows films composed of silanized Si—RBC particles. Provided are SEM images (top down view) of film surfaces having (a) hexamethyldisilazane (HMDS)-dried discocytes; (b) HMDS-dried stomatocytes; (c) HMDS-dried echinocytes; and (d) HMDS-dried spherocytes. Also provided is (e) a graph showing corresponding contact angle measurements (error bars represent standard deviation calculated from independent triplicates), in which control measurements from a flat glass surface functionalized with HMDS yielded a contact angle θ of 56°.

Next, we casted solutions comprising HMDS-dried particles (HMDS reacts with exposed silanols on the Si—RBCs to form terminal trimethylsilyl groups that increase the hydrophobicity of individual particles) dispersed in methanol and observed their properties as they assembled into films. Contact angle (A) measurements of the resultant hydrophobic films showed increasing surface hydrophobicity as particle composition of the films progressed from stomatocyte/discocyte morphology to echinocytes and spherocytes. Films comprising the latter two presented a coarser, more hierarchical surface compared to stomatocyte/discocyte films and displayed superhydrophobicity ($\theta \approx 150°$; FIG. 27).

Indeed, depending on their differing shapes, single to few layers of particles were observed to combine into clusters (FIG. 24b,c). As layers deposited and ultimately dried, we observed characteristic cracking patterns for each shape following rapid drying (FIG. 24d). The formation of these patterns was controlled by a wide range of parameters, including drying rate as well as interparticle, capillary, and hydrodynamic forces. The salient differences among these structures can be explained by considering the variation in interparticle attraction/cohesion across particle libraries (evident, for instance, when comparing FIG. 24b with FIG. 24c).

Figure 28A:
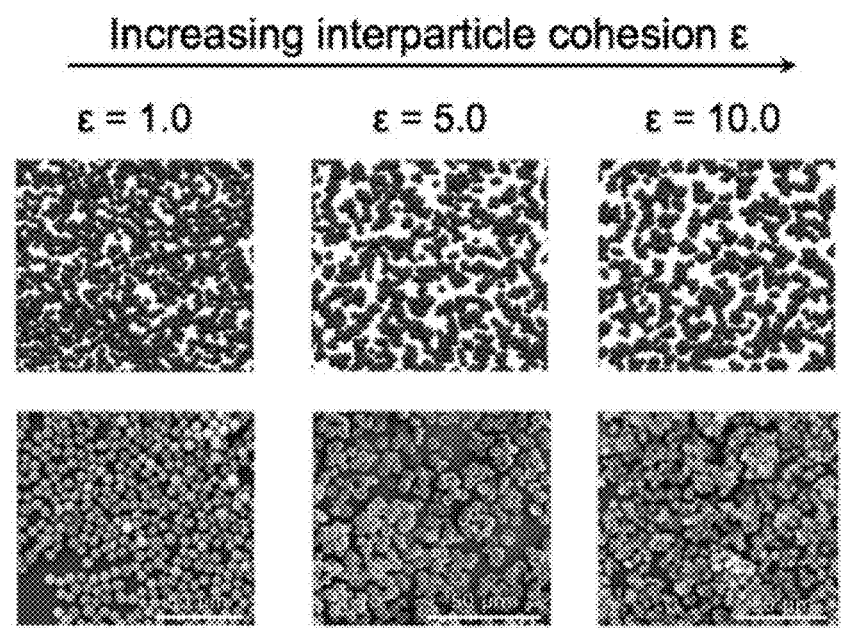
FIG. 28A-28B shows Brownian dynamics-like simulations of interparticle cohesion using a simple model accounting for hydrodynamic drag, as well as buoyancy effects related to the position of the drying front. Provided are (A) results of the simulation (top panels) and representative SEM images (left to right) of spherocytes, stomatocytes, and echinocytes (lower panels); and (B) a graph showing the Lennard-Jones inter-particle potential for drying simulations. The potential E has the form $$E = 4\varepsilon\left[\left(\frac{\sigma}{r-r_0}\right)^{12} - \left(\frac{\sigma}{r-r_0}\right)^{6}\right],$$
Figure 28B:
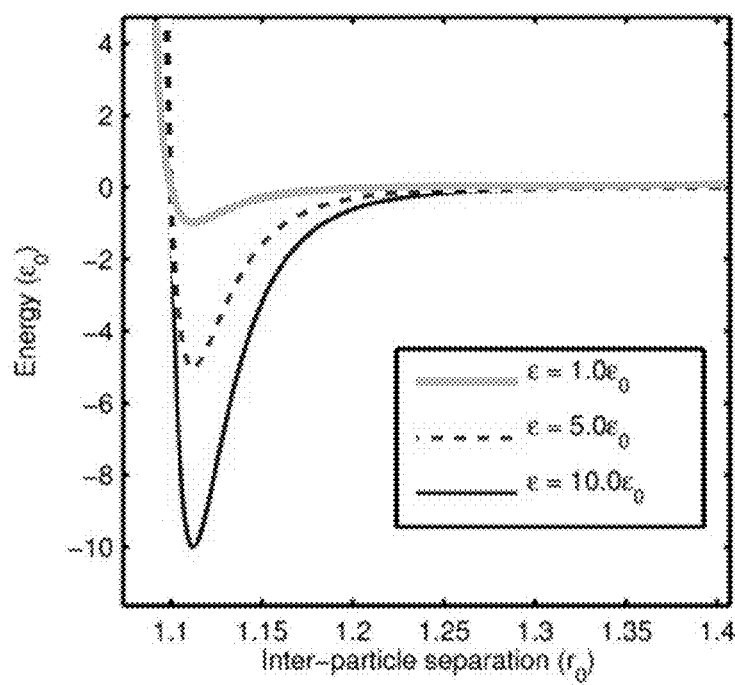

To further understand these particle interactions, we conducted Brownian dynamics-like simulations of particle drying on the scale of several particle layers, where the interparticle forces were modeled by varying the strength of a shifted Lennard-Jones potential (FIG. 28A-28B). The simulations also accounted approximately for hydrodynamic drag (see, e.g., Kumar A et al., "Origins of the anomalous stress behavior in charged colloidal suspensions under shear," Phys. Rev. E 2010 November; 82(5 Pt 1):051401), as well as buoyancy effects related to the position of the drying front. In the case of spherocytes, where particles were essentially spheres that present small protrusions, the attraction was relatively low. As a result, individual particles could rearrange freely with respect to one another to accommodate drying stresses, resulting in a surface free of cracks.

At the opposite end were echinocytes, which interlocked into mechanically stable 3D clusters, ultimately forming the largest domains (FIG. 24*d*). We modeled this with a larger interparticle attraction force, which resulted in the formation of larger clusters in the simulations. Despite the simple spherically symmetric interaction model, the simulations qualitatively reproduced the resulting particle microstructures (FIG. 28A). This indicated that particle aggregation on the scale of several particle layers may play a key role in the resulting cracking patterns.

These interesting properties provide opportunities to better understand and ultimately tune bulk systems based on jammed packing of hard, non-spherical particles, an area lacking well-defined experimental systems despite considerable theoretical work (see, e.g., Torquato S et al., "Jammed hard-particle packings: From Kepler to Bernal and beyond," *Rev. Mod. Phys.* 2010 September; 82(3):2633-72). These packing characteristics could prove favorable over existing technologies for applications such as separations, filtration, and decontamination, and would be further enabled if Si—RBCs display suitable internal particle features such as well-defined porosity and high surface area. Previously, we observed that calcined silica replicas of Chinese hamster ovarian (CHO) cells exhibited a wide range of meso- to macroscale pores (Kaehr B et al., *Proc. Natl. Acad. Sci. USA* 2012 October; 109(43):17336-41). This was expected given the complex interior of tissue-derived, nucleated cells. However, mammalian RBCs are anucleate, devoid of organelles, and consisting of a relatively homogeneous cytoplasm composed primarily of hemoglobin.

Thus, we examined the internal properties of individual particle libraries using physisorption. $N_2$ sorption isotherms obtained from calcined (500° C., 4 hours) particles are shown in FIG. 29. Analysis of the sorption isotherms using nonlocal density functional theory (NLDFT) indicated a high surface area that is relatively consistent (~640-680 $m^2/g$) across the particle libraries. Surface areas were determined using the NLDFT over the range $P/P_0=0.05-0.3$ and values ($m^2/g$) for each library were stomatocyte=643.4; discocyte=640.8; echinocyte=661.0; and spherocyte=681.0. The equivalent Brunauer-Emmett-Teller (BET) nitrogen surface area values (which can often overestimate surface area, see, e.g., Sing K S W et al., *J. Pure Appl. Chem.* 1985; 57(4):603-19) are stomatocyte=919.1; discocyte=863.5; echinocyte=916.0; and spherocyte=873.0. Pore size distributions were calculated using NLDFT assuming cylindrical pores in an oxide material.

The isotherms obtained from discocyte and stomatocyte-templated silica particles showed a similar sorption response (FIG. 29*a*), indicating little change in mesopore composition as RBC-templated particles transition from native (discocyte) to cup (stomatocyte) morphology. However, as particles transform along the discocyte-echinocyte-spherocyte pathway, a comparison of the isotherms (FIG. 29*b*) showed striking differences at higher partial pressures, with distinct hysteresis loops. These are indicative of differences in pore structure and connectivity but are difficult to precisely interpret (see, e.g., Sing K S W et al., "Reporting physisorption date for gas/solid systems with special reference to the determination of surface area and porosity (Recommendations 1984)," *J. Pure Appl. Chem.* 1985; 57(4):603-19).

NLDFT analysis of pore dimensions showed peak values of 4-6 nm across all samples (FIG. 29*c*), which roughly corresponded to the average diameter of native hemoglobin (see, e.g., Perutz M F, "Submicroscopic structure of the red cell," *Nature* 1948 February; 161(4084):204). However, an increase in larger mesopores was evident as particles progress from discocytes along the crenate pathway, eventually forming spherocytes. This indicated that changes in internal structure/organization following the addition of crenating agents are ultimately conferred to the silica replica. As cytoplasmic components aggregate or otherwise condense during crenation, their extraction via calcination resulted in larger pores, as evidenced by the largest pore sizes obtained from spherocyte replicas, templated from the RBCs with highest internal density.

We speculated that these apparent differences in porosity conferred differences in macromolecular accessibility. To address this question, we incubated calcined discocytes and spherocytes in a solution of myoglobin (a ~3.5 nm diameter protein) and measured protein uptake using the 409 nm absorption peak of myoglobin. In contrast to discocytes, the protein visibly loaded into spherocyte silica particles (FIG. 29*d*), indicating a more accessible pore network for the stomatocyte particles despite no apparent differences in pore structure as seen in TEM images of crushed silica particles (FIG. 30). We estimated loading of ~$10^8$ myoglobin per spherocyte particle that, to put into perspective, was roughly an order of magnitude less heme content than a normal red blood cell (~$10^9$).

Given the accumulated wealth of information regarding how cells receive and respond to signals and coordinate behavior, this knowledge can now be reexamined as a starting point for the design of particles and materials. We have demonstrated this approach by exploiting the well-known morphological response of RBCs to chemical agents and have uncovered the potential to tune internal structure/porosity in a mesoporous material using a biological response. Similar internal templating can be considered in other soft cell templates, for instance, using GTP-activation to induce cytoskeletal rearrangements toward creation of hierarchical or unbranched networks (see, e.g., Hall A, "Rho GTPases and the actin cytoskeleton," *Science* 1998 January; 279(5350):509-14). Large internal pores could be developed using vacuole inducing agents (see, e.g., Geng Y et al., "Chloroquine-induced autophagic vacuole accumulation and cell death in glioma cells is p53 independent," *Neuro Oncol.* 2010 May; 12(5):473-81). Accordingly, described herein are constructs formed from shape-encoded biological samples and methods for forming shape-encoded constructs. For instance, chemical and biological agents can be employed to induce a desired, complex geometry; and the silification processes described herein stabilizes these complex structures to form useful constructs.

Example 6: Shape-Encoded Cells Providing Further Functionalized or Converted Constructs Constructs from other non-silica materials are useful for numerous purposes. Thus, we investigated the use of shape-encoded cells to provide non-silica based constructs. In particular, as shown in this example, the durability of the silica composites provided opportunities for shape-preserving transformations into metallic, semiconductive, and ferromagnetic particles and assemblies.

Locking induced cellular dynamics into a "Si-cell" provided a starting point for further shape-preserved conversions into other functional materials, such as noble metals (e.g., Pt; FIG. 31), semiconductors (e.g., Si; FIG. 32), and magnetically-responsive particles (FIG. 33*a*-33*b*). Such converted or functionalized constructs can be prepared in any useful manner (e.g., as described herein).

Nanoparticle-functionalized constructs can be employed to deliver therapeutic agents or to provide a detectable label. For the Pt construct shown in FIG. 31, Si—RBCs were incubated overnight in a solution of 20 mM potassium tetrachloroplatinate ($K_2PtCl_4$) dissolved in $dH_2O$, centrifuged, and rinsed in $dH_2O$ (2×). L-ascorbic acid was added to a final concentration of 80 mM and allowed to react for 2 hours. In the obtained Si—RBC constructs, we observed high nanoparticle density on regions of positive curvature (white arrows in FIG. 31a). Dissolution of the underlying silica composite template provided a unique geometry, in which the particle included a void (FIG. 31b).

Silicon surfaces provide a useful handle for further chemical modifications, as derivatization chemistry with silicon-based substrates are well established. Thus, we also generated silicon constructs, as seen in FIG. 32. In brief, silicon RBCs were generated from calcined Si—RBCs using a published procedure (see, e.g., Bao Z et al., "Chemical reduction of three-dimensional silica micro-assemblies into microporous silicon replicas," *Nature* 2007 Mar. 8; 446 (7132):172-5). Si—RBC particles (formed of silica $SiO_2$) were placed in a sealed stainless steel mini-reactor containing magnesium powder (3:1 wt/wt ratio of Mg:$SiO_2$), heated to 650° C. for 4 hours, and allowed to cool to room temperature. Particles were rinsed in 1.0 N HCl for 2 hours to dissolve the magnesia (MgO) phase, leaving behind the silicon RBCs (containing Si).

Magnetic materials can be interrogated by a magnetic field, which can be attractive for detection and imaging platforms, genetic assays, chemical reactors, as well as for data storage. Furthermore, magnetic forces can be employed to promote self-assembly of magnetic particles into useful supramolecular structures. As can be seen, Si—RBCs were pyrolyzed following iron ion infusion to generate weakly ferromagnetic particles (FIG. 33a,b). These ferromagnetic particles assembled into linear (FIG. 33c) or kinked (FIG. 33d) structures depending on the symmetry of the constituent particles. The magnetic RBCs contained iron carbide ($Fe_3C$), as indicated by XRD analysis (FIG. 34) and micro-Raman spectroscopy (FIG. 35). In brief, magnetic RBCs were generated by adapting a published procedure (see, e.g., Schnepp Z et al., "Biotemplating of metal carbide microstructures: the magnetic leaf," *Angew. Chem. Int. Ed. Engl.* 2010 Sep. 3; 49(37):6564-6). First, Si—RBCs were incubated overnight in a 10% solution (wt/vol) of iron acetate, $Fe(CH_3CO_2)_2$. Following extensive rinsing in $dH_2O$ and air-drying from methanol, cells were heated to 700° C. (2° C./min) under a flow of 5% hydrogen (in nitrogen) and cooled to room temperature.

Finally, the replication of cellular structure in silica provides a chemical handle to silane chemistry, allowing nearly limitless opportunities for surface functionalization, for instance, to dictate selective dispersibility in organic and aqueous phases (FIG. 36). This will prove enabling particularly if bioactivity can be maintained. Indeed, silicification does not appear to inhibit, for example, the peroxidase activity of RBCs (FIG. 37). Maintenance of more delicate (e.g., $O_2$ and CO binding) and more complex (e.g., glycolysis) functions in Si—RBCs presents opportunities for future work that could enable development of general strategies to address challenges for biocatalyst stabilization (see, e.g., Stepankova V et al., "Strategies for stabilization of enzymes in organic solvents," *ACS Catal.* 2013; 3(12):2823-36; and Hanefeld U et al., "Understanding enzyme immobilisation," *Chem. Soc. Rev.* 2009 February; 38(2):453-68).

Accordingly, described herein are constructs having further functionalized or converted structures. Any useful material functionalization and conversions can be employed using the silica composites herein as a template (see, e.g., material transformations in Losic D et al., "Diatomaceous lessons in nanotechnology and advanced materials," *Adv. Mater.* 2009 August; 21(29):2947-58, which is incorporated herein by reference in its entirety).

Applying the RBC shape continuum described herein provides a new element of structural control that can enable studies examining effects of, for example, geometric curvature (see, e.g., Walker D A et al., "Geometric curvature controls the chemical patchiness and self-assembly of nanoparticles," *Nat. Nanotechnol.* 2013 September; 8(9):676-81) and magnetic symmetry (see, e.g., Yan J et al., "Linking synchronization to self-assembly using magnetic Janus colloids," *Nature* 2012 November; 491(7425):578-81) for materials development and self-assembly.

Further functionalization, for example, with natural (see, e.g., Hu C M et al., "Erythrocyte membrane-camouflaged polymeric nanoparticles as a biomimetic delivery platform," *Proc. Natl. Acad. Sci. USA* 2011 Jul. 5; 108(27):10980-5) or synthetic membranes (see, e.g., Liu J et al., "Porous nanoparticle supported lipid bilayers (protocells) as delivery vehicles," *J. Am. Chem. Soc.* 2009 Feb. 4; 131(4):1354-5) should facilitate in vivo applications. Overall, the addition of "cell diversity" and "differentiation" to the material synthesis toolkit offers an unprecedented pathway for further exploration.

Other Embodiments

All publications, patents, and patent applications, including U.S. Provisional Application No. 61/638,315, filed Apr. 25, 2012, mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:
1. A method comprising:
providing a biological sample comprising one or more cells;
treating the biological sample with one or more chemical or biological agents to alter shape of the biological sample; and
introducing a silicic acid compound having the structure $Si(OR)_4$ or $R'Si(OR'')_3$ to the biological sample, thereby forming one or more conformal silica nanolayers on and within the one or more cells by condensing a silicic acid selected from the group consisting of orthosilicic acid, metasilicic acid, disilic acid, and pyrosilicic acid, and thereby forming a silica composite,
wherein each R is, independently, an optionally substituted alkyl, wherein each of R' and R" is, independently, an optionally substituted alkyl, aryl, alkaryl, alkenyl, and alkynyl, wherein hydrolysis of the silicic acid compound provides an alcohol and the silicic acid.

2. The method of claim 1, wherein the biological sample is an organism, an organ, a tissue biopsy, a tissue section, a cell, a multicellular sample, a soft tissue sample, a population of cells, a sample from an animal source, or a sample from a mammalian source.

3. The method of claim 1, wherein the forming step comprises the formation of a hydrolyzed silicic acid and the alcohol that both enter the one or more cells, and wherein the hydrolyzed silicic acid interact with a cellular component of the one or more cells.

4. The method of claim 1, wherein the forming step comprises immersing the biological sample in an acidic isotonic solution, and wherein the solution comprises or provides the silicic acid capable of forming the one or more conformal silica nanolayers.

5. The method of claim 4, wherein the solution has a pH of from about 2 to about 4.

6. The method of claim 5, wherein the concentration of silicic acid results in a self-limiting reaction between the silicic acid with an internal surface and with an external surface present on or within the biological sample.

7. The method of claim 4, wherein the forming step further comprises replacing the solution with a second acidic isotonic solution, and wherein the second solution comprises a silicic acid capable of forming the one or more conformal silica nanolayers.

8. The method of claim 1, further comprising:
further treating the biological sample with one or more fixative reagents.

9. The method of claim 1, further comprising:
washing the silica composite with one or more aqueous or solvent washes; and
drying the washed silica composite, thereby forming a dehydrated silica composite.

10. The method of claim 1, further comprising:
forming an inorganic silica composite by heating the silica composite to a temperature sufficient to remove organic material of the biological sample.

11. The method of claim 1, further comprising:
forming a carbonized replica by heating the silica composite to a temperature sufficient to carbonize organic material of the biological sample.

12. The method of claim 11, wherein the carbonized replica is formed in an inert atmosphere or a reducing atmosphere.

13. The method of claim 11, further comprising:
forming a carbon replica by etching the underlying silica nanolayers(s) from the carbonized replica, thereby forming a conductive carbon replica.

14. The method of claim 1, wherein the one or more chemical or biological agents induce an intercellular or an extracellular change to the biological sample.

15. The method of claim 14, further comprising:
forming a carbonized replica by heating the silica composite to a temperature sufficient to carbonize organic material of the biological sample.

16. The method of claim 1, further comprising:
forming a converted replica by reacting the silica composite by way of a displacement reaction, an oxidation reaction, a magnesiothermic reduction reaction, a carbothermal reduction reaction, a hydrothermal reaction, or a reactive metal reaction.

17. The method of claim 16, wherein the converted replica comprises magnesium oxide, iron, iron carbide, or titanium oxide.

18. The method of claim 14, further comprising:
forming a converted replica by reacting the silica composite by way of a displacement reaction, an oxidation reaction, a magnesiothermic reduction reaction, a carbothermal reduction reaction, a hydrothermal reaction, or a reactive metal reaction.

19. The method of claim 18, wherein the converted replica comprises silicon, magnesium oxide, iron, iron carbide, or titanium oxide.

20. The method of claim 14, further comprising:
forming an inorganic silica composite by heating the silica composite to a temperature sufficient to remove organic material of the biological sample.

21. The method of claim 1, further comprising:
functionalizing the silica composite by use of a silanizing agent, a particle, or a coating.

22. The method of claim 1, wherein the one or more chemical or biological agents is selected from the group consisting of an antibiotic, a bacterial protein toxin, a cell permeabilizing agent, an antimicrobial peptide, an antigen, an inhibitor, a growth factor, a drug, and an amphipath.

23. The method of claim 2, wherein the cell is a mammalian cell.

* * * * *